US008178751B2

(12) United States Patent
Frank et al.

(10) Patent No.: US 8,178,751 B2
(45) Date of Patent: May 15, 2012

(54) USE OF STOMATIN (STM1) POLYNUCLEOTIDES FOR ACHIEVING A PATHOGEN RESISTANCE IN PLANTS

(75) Inventors: Markus Frank, Neustadt (DE); Patrick Schweizer, Ballenstedt (DE); Dimitar Douchkov, Gaterslebene (DE)

(73) Assignee: BASF Plant Science GmbH, Ludwigshafen (DE)

( * ) Notice: Subject to any disclaimer, the term of this patent is extended or adjusted under 35 U.S.C. 154(b) by 824 days.

(21) Appl. No.: 12/160,287

(22) PCT Filed: Jan. 4, 2007

(86) PCT No.: PCT/EP2007/050062
§ 371 (c)(1),
(2), (4) Date: Jul. 8, 2008

(87) PCT Pub. No.: WO2007/080143
PCT Pub. Date: Jul. 19, 2007

(65) Prior Publication Data
US 2009/0222944 A1    Sep. 3, 2009

(30) Foreign Application Priority Data

Jan. 12, 2006 (EP) ..................................... 06100304

(51) Int. Cl.
*C12N 15/09* (2006.01)
*C12N 15/29* (2006.01)
*C12N 15/82* (2006.01)
*A01H 5/00* (2006.01)

(52) U.S. Cl. ........ 800/279; 800/278; 800/298; 800/287; 800/320; 435/320.1; 435/468; 435/419; 536/23.6; 536/24.5

(58) Field of Classification Search ........................ None
See application file for complete search history.

(56) References Cited

U.S. PATENT DOCUMENTS 6,506,559 B1 * 1/2003 Driver et al. ...................... 435/6
2005/0132439 A1   6/2005 Kogel et al.

FOREIGN PATENT DOCUMENTS

WO    WO-00/15817 A2    3/2000
WO    WO-03/020939 A1   3/2003

OTHER PUBLICATIONS

Fourgoux-Nicol et al (1999), Plant Molecular Biology 40: 857-872.*
Guo et al. PNAS, 101 : 9205-9210, 2004.*
Keskin et al. Protein Science, 13:1043-1055, 2004.*
Wesley et al. Plant Journal (2001) 27(6), 581-590.*
Nadimpalli, R., et al., "Prohibitins, Stomatins, and Plant Disease Response Genes Compose a Protein Superfamily That Controls Cell Proliferation, Ion Channel Regulation, and Death", The Journal of Biological Chemistry, 2000, vol. 275, No. 38, pp. 29579-29586.
Opalski, K. S., et al., "The Receptor-Like MLO Protein and the RAC/ROP Family G-Protein RACB Modulate Actin Reorganization in Barley Attacked by the Biotrophic Powdery Mildew Fungus *Blumeria graminis* f.sp. *hordei*", The Plant Journal, 2005, vol. 41, pp. 291-303.
Bhat, R. A., et al., "Recruitment and Interaction Dynamics of Plant Penetration Resistance Components in a Plasma Membrane Microdomain", PNAS, 2005, vol. 102, No. 8, pp. 3135-3140.
Hückelhoven, R., et al., "Overexpression of Barley BAX Inhibitor 1 Induces Breakdown of *mlo*-Mediated Penetration Resistance to *Blumeria graminis*", PNAS, 2003, vol. 100, No. 9, pp. 5555-5560.
Hammond-Kosack, K. E., et al., "Resistance Gene-Dependent Plant Defense Responses", The Plant Cell, 1996, vol. 8, pp. 1773-1791.
Stewart, G. W., et al., "Stomatin: A Putative Cation Transport Regulator in the Red Cell Membrane", Biochimica et Biophysica Acta, 1993, vol. 1225, pp. 15-25.
Stewart, G. W., et al., "Isolation of cDNA Coding for an Ubiquitous Membrane Protein Deficient in High $Na^+$, Low $K^+$ Stomatocytic Erthrocytes", Blood, 1992, vol. 79, No. 6, pp. 1593-1601.
Petersen, M., et al., "*Arabidopsis* MAP Kinase 4 Negatively Regulates Systemic Acquired Resistance", Cell, 2000, vol. 103, pp. 1111-1120.
Brodersen, P., et al., "Knockout of *Arabidopsis* Accelerated-Cell-Death11 Encoding a Sphingosine Transfer Protein Causes Activation of Programmed Cell Death and Defense", Genes & Development, 2002, vol. 16, pp. 490-502.
"Putative Band 7 Protein [*Oryza sativa* (Japonica Cultivar-Group)]", NCBI Database Accession No. XP_480193, Nov. 9, 2004.
"Stomatin-Like Protein [*Zea mays*]", NCBI Database Accession No. AAF68388, Sep. 11, 2002.
"Putative Protein [*Arabidopsis thaliana*]", NCBI Database Accession No. CAB81408, Nov. 14, 2006.
"Band 7 Family Protein [*Arabidopsis thaliana*]", NCBI Database Accession No. NP_567778, Apr. 20, 2007.
"Band 7 Family Protein [*Arabidopsis thaliana*]", NCBI Database Accession No. NP_200221, Apr. 20, 2007.
"Stomatin-Like Protein [*Arabidopsis thaliana*]", NCBI Database Accession No. AAM63205, Jan. 27, 2006.
Jacobs, A. K., et al., "An *Arabidopsis* Callose Synthase, GSL5, Is Required for Wound and Papillary Callose Formation", The Plant Cell, 2003, vol. 15, pp. 2503-2513.

* cited by examiner

*Primary Examiner* — Medina A Ibrahim
(74) *Attorney, Agent, or Firm* — Connolly Bove Lodge & Hutz, LLP

(57) ABSTRACT

The invention relates to a method of generating or increasing a pathogen resistance in plants by reducing the expression of at least one stomatin polypeptide or a functional equivalent thereof. The invention relates to novel nucleic acid sequences coding for a *Hordeum vulgare* stomatin (HvSTM1) polynucleotide and describes homologous sequences (STM1) thereof, and to their use in methods for obtaining a pathogen resistance in plants, and to nucleic acid constructs, expression cassettes and vectors which comprise these sequences and which are suitable for mediating a fungal resistance in plants. The invention furthermore relates to transgenic organisms, in particular plants, which are transformed with these expression cassettes or vectors, and to cultures, parts or transgenic propagation material derived therefrom.

37 Claims, 4 Drawing Sheets

Figure 1:

HAU formation relative to empty-vector control (%):

| | | Exp.1 | Exp.2 | Exp.3 | Exp.4 | Exp.5 | Mean | SD | SDM | t Quantile against 100 | p (t-test against 100) |
|---|---|---|---|---|---|---|---|---|---|---|---|
| HW03O11 | Stomatin | 36.50 | | 48.64 | 72.58 | 49.21 | 49.21 | 16.43 | 8.22 | 6.18 | 0.005 |
| HO12F09 | SNAP34 | 138.91 | 192.9 | 193.83 | 199.36 | 179.85 | 179.85 | 24.77 | 11.08 | 7.20 | 0.0025 |
| TA30 (Mean) | Empty vector | 100.00 | 100.00 | 100.00 | 100.00 | 100.00 | 100.00 | 0.00 | 0.00 | | |

Figure 2 (page 1 of 3):

```
                          1                                                                        80
BlastX_1_STM_Os        (1) ------------------------------------------------HAASSTRFSRYYSRDDVSRYFA--
BlastX_2_STM_Zm        (1) -MATLRRSVGPARQLLRPRPLPLP------------------------SAPALSRSFSRFNPRDDSSMFDP--
BlastX_3_STM_Ath       (1) -MASLRRSAVPARQLLLPRHFAAAG-----------------------TSPPPIFSAAASTVRQFTSAGYPS-
BlastX_4_STM_Ath       (1) -MNHLVRKSSVGYSALRSVSYLRQSAV---------------------TSPPPIFSAAASTVRQFTSAGYPS-
BlastX_5_STM_Ath       (1) -MNHLVRKSSVGYSALRSVSYLRQSAV---------------------TSPPPIFSAAASTVRQFTSAGYPS-
BlastX_6_STM_Ath       (1) -MNQLALSRSGYTAAVRFPLPMLSAAVPKILSSLAAASTVRNFSSTGSPLTSYQINKPSPSKSETSRLLHQSSAGTPPQ
Translation of HvSTM1 cDNA (1) -MNQLALSRSGYTAAVRFPLPMLSAAVPKILSSLAAASTVRNFSSTGSPLTSYQINKPSPSKSETSRLLHQSSAGTPPQ
                          (1) MAVSTATRMLRRAVPGHLLRNANPAAA---------------------TAALLQRRXYRGGADPXPSLYHPP--
Consensus                     MN LLRKSS     AALR LP L  AA                      TAPSPSRSFSA  LRQ SSAG P 81                                                                       160
BlastX_1_STM_Os       (49) ------------LSTPVNMGVSIVPEKKAFVVERFGYVKTLGSGIHVLNPLVDRIAYVHSLKEEAIPIPDQS
BlastX_2_STM_Zm       (50) ------------PEPPVNMGVSIVPEKKAWVERFGKVLKTLGSGFHLLRPAVDRIAYVHSLKEETIPIPHQN
BlastX_3_STM_Ath      (51) -----------NSFQLTPDNWGIRIVPERKAFVIERFGKVATTLPSGIHFLIPFVDRIAYVHSLKEEAIPIPNQT
BlastX_4_STM_Ath      (51) -----------NSFQLTPPTNWGIRIVPERARVIERFGKYATTLPSGIHFLIPFVDRIAYVHSLKEEAIPIPNQT
BlastX_5_STM_Ath      (79) QLFGARSFSSPSSDFNSYHINPPSNWGIRIVPERKACVIERFGKEHTTLPAGIHFLVPFVDRIAYVHSLKEEAIPIGNQT
BlastX_6_STM_Ath      (79) QLFGARSFSSPSSDFNSYHINPPSNWGIRIVPERKACVIERFGKEHTTLPAGIHF VPFVDRIAYVHSLKEEAIPIGNQT
Translation of HvSTM1 cDNA (53) ------------PTPANLGLSIVPERKARVWERFGKYLKTLPSGIHLMPGVDRTAYVHSLKEEAIPIPDNS
                         (81) NSF L PPSNWGIRIVPERKAFVIERFGKY TTLPSGIHFLIPFVDRIAYVHSLKEEAIPIPNQT
Consensus 161                                                                      240
BlastX_1_STM_Os      (110) AITKDNVSIQIDGVLYVKIVDPYLASYGVENPIEAVIQLAQTMRSELGKITLDKTFEERDTLNEQIVRSINEAATDWGL
BlastX_2_STM_Zm      (111) AITKDNVTIQIDSVIIVKIMDPVIASYGVENPIYAVEQLAQTMRSELGKITLDKTFEERDALNEKIVSAINEAATDWGL
BlastX_3_STM_Ath     (116) AITKDNVSIHIDGVLIVKIVDPKLASYGVESPIYAVVQLAQTMRSHIGKITLDKTFEERDILNEKIVERINVAAKDWGL
BlastX_4_STM_Ath     (116) AITKDNVSIHIDGVLIVKIVDPKLASYGVESPIYAVVQLAQTMRSELGKITLDKTFEERDILNEKIVERINVAAKDWGL
BlastX_5_STM_Ath     (159) AITKDNVSIHIDGVLIVKIVDPRLASYGVENPIYAVMQLAQTMRSELGKITLDKTFEERDTLNEKIVRAINVAAKDWGL
BlastX_6_STM_Ath     (159) AITKDNVSIHIDGFLIVKIVDPRLASYGVENPIYAVMQLAQTMRSELGKITLDKTFEERDTLNEKIVRAINVAAKDWGL
Translation of HvSTM1 cDNA (113) AITKDNVSIQIGGWIVKIVDPYVASYGVANPIYAVIQLAQTMRSELGKITLDKTFEERDTLNLNIVSSINEAETWGL
Consensus               (161) AITKDNVSIHIDGVLIVKIVDPKLASYGVENPIYAVIQLAQTMRSELGKITLDKTFEERDTLNEKIVERINVAAKDWGL 241                                                                      320
BlastX_1_STM_Os      (190) KCLRVEIRDISPPRCVKVAMEMQARERKKRAQILESE-----------GAMDQANRAKGEAEAILAK
BlastX_2_STM_Zm      (191) KCLRVETRDINPPACIRQAAMEMQAEAERKKRAQILESEGMKQAQILESEGKKTAQILESEGAMDLANRAKGAAEAILAK
BlastX_3_STM_Ath     (196) QCLRYEIRDIMPPHGVRAAMEMQAEAERKKRAQILESEGRQSHINIADGKKSSVILASEEAKMDQVNRAQGEAEAITAR
BlastX_4_STM_Ath     (196) QCLRYEIRDIMPPHGVRAAMEMQAEAERKKRAQILESEGERQSHINIADGKKSSVILASEEAKMDQVNRAQGEAEAITAR
BlastX_5_STM_Ath     (239) QCLRYEIRDIMPPNGVRVAMEMQAEAERKKRAQILESEGEROAHINRADGKKSSV LESEAAMMDQVNRAQGEAEAILAR
BlastX_6_STM_Ath     (239) QCLSYEIRDIMPPNGVRVAMEMQAEAERKKRAQILESEGERQAHINRADGKKSSVILESEAAMMDQVNRAQGEAEAILAR
Translation of HvSTM1 cDNA (193) KCLRYEIRDITPPDCVKKAMEMQAEAERKKRAQILESE---------GAMMEKANRAKGEAEAILAR
Consensus              (241) QCLRYEIRDIMPP GVR AMEMQAEAERKKRAQILESEGERQAHIN ADGKKSSVIL SEAAMMDQVNRAQGEAEAILAR
```

Figure 2 (page 2 of 3):

```
                              321                                                                                       400
BlastX_1_STM_Os       (248)   SEATARGIRMVSEAMRTKGSTEAANLRVAEQYMKAFANLAKKSNTILLPSDAGNPSSIAQSIQYKHTCQTNSLKSGKY
BlastX_2_STM_Zm       (271)   SEATARGMRVSDAMTTEGSAKAASLKIAEQYIEAFSNLAQKTNTMLLPGDSASPASIVAQAMKTYEQHSHSQALKSHP
BlastX_3_STM_Ath      (276)   AQATAKGLVILSQSLKETGGVEAASLRVAEQYTTAFGNIAKEGTIMLLPSGASNPASMIAQALTMYKSEVINGPS-KDHQ
BlastX_4_STM_Ath      (276)   AQATAKGIVELSQSIKETGGVEAASLRVAEQYTTAFGNIAKEGTIMLLPSGASNPASMIAQALTMYKSEVINGPS-KDHQ
BlastX_5_STM_Ath      (319)   AQATAKGLAMVSQSLKEAGGEEAASLRVAEQYIQAFGTIAKEGTLMLIPSNVDNPASMIAQALGMYKGLSTKVPTVVSGK
BlastX_6_STM_Ath      (319)   AQATAKGLAMVSQSLKEAGGEEAASLRVAEQYTQAFGTIAKEGTLMLLPSNVDNPASMIAQALGMYKGLSTKVPTVVSGK
Translation of HvSTM1 cDNA (251) SQATAEGIRMVSESFKTEGSTEAASLRIAEQYIRAFSELARTTNTMLLPSDAGNPGTMIAQALQIYNHTYKQKLTLGSPS
Consensus             (321)   AQATAKGL LVSQSLKE GG EAASLRVAEQYI AFGNIAKEGTMLLPS A NPASMIAQAL MYK L      PTL S 401                                                                                       480
BlastX_1_STM_Os       (328)   LSDAEETRPEEEELDSTDLPSLSSGMPSPDMPDDHDK------TFSLQRRNKDKH----------------------
BlastX_2_STM_Zm       (351)   Q-EELKESG----E--TSPAPSSEASKTPPLIEEADSNQ----TFSLQRP-KNKQ----------------------
BlastX_3_STM_Ath      (355)   ETQAIDETDLEBLEDMGEKHHISEGSNNRSGSISFDTEKPA-LPIVSFVFQTNPFNPKTMGACASKPKESDIVEGSVSTEN
BlastX_4_STM_Ath      (355)   ETQAIDETDLEBLEDMGEKHHISEGSNNRSGSISFDTEKPGHTGEPRESLQNRNKDPQ------------------
BlastX_5_STM_Ath      (399)   LLE--------------------------------------------------------------------------
BlastX_6_STM_Ath      (399)   LLE--------------------------------------------------------------------------
Translation of HvSTM1 cDNA (331) PSKQAVAAERADLSLGMPSVSDLGTFPHQK--------------------------------------------
Consensus             (401)   TE L ETD  E          S GS      D                     F        Q 481                                                                                       560
BlastX_1_STM_Os       (378)   --
BlastX_2_STM_Zm       (395)   --
BlastX_3_STM_Ath      (434)   AVVESKNAATETDATLTQEKKEHSIEETKKEGETKEDSSEATKARPTPEAVKAEEKTSSETEPPAQETTPAAKTDEAPLV
BlastX_4_STM_Ath      (412)   --
BlastX_5_STM_Ath      (402)   --
BlastX_6_STM_Ath      (402)   --
Translation of HvSTM1 cDNA (361) --
Consensus             (481)   --

561
BlastX_1_STM_Os       (378)   --
BlastX_2_STM_Zm       (395)   --
BlastX_3_STM_Ath      (514)   IL
BlastX_4_STM_Ath      (412)   --
BlastX_5_STM_Ath      (402)   --
BlastX_6_STM_Ath      (402)   --
Translation of HvSTM1 cDNA (361) --
Consensus             (561)
```

Figure 2 (page 3 of 3):

Data for HvSTM1
Sequence_1 (only yellow matches)

XPXNXGXXIVPEXKAXVXERFGKXXXTLXXGXHXLXPXVDRIAYVHSLKEEXIPIXXXXAITKDNVXIXIXXXXYVKIXDPXXAS
YGVXXPIXAVXQLAQTTMRSELGKITLDKTFEERDXLNXXIVXXINXAAXXWGLXCXXYEIRDIXPPXGXXXAMEMQAXAERKKR
AQILESEXXXXXXXXXXXXXXXXXXXAXXXXXNRAXGXAEAILAXXXATAXGXXXXXSXXXXXXGXXXXAAXLXXAEQYXXAF
XXXAXXXXXLLPXXXXPXXXXAQXX

Sequence_2 (only yellow, blue and green matches)

PPXNWGIRIVPERKAFVIERFGKYXTTLPSGIHFLXPFVDRIAYVHSLKEEAIPIPNQTAITKDNVSIHIDGVLYVKIVDPKLAS
YGVENPIYAVXQLAQTTMRSELGKITLDKTFEERDTLNEKIVEAINVAAKDWGLQCLRYEIRDIMPPXGVRXAMEMQAEAERKKR
AQILESEGERQXHINXADGKKSSVILXSEAAMMDQVNRAQGEAEAILARAQATAKGLXLVSQSLKEXGGXEAASLRVAEQYIXAF
GNIAKEGTTMLLPSXAXNPASMIAQAL

Sequence_3 (yellow, blue and green matches)

PPSNWGIRIVPERKAFVIERFGKYXTTLPSGIHFLIPFVDRIAYVHSLKEEAIPIPNQTAITKDNVSIHIDGVLYVKIVDPKLAS
YGVENPIYAVIQLAQTTMRSELGKITLDKTFEERDTLNEKIVEAINVAAKDWGLQCLRYEIRDIMPPXGVRXAMEMQAEAERKKR
AQILESEGERQAHINXADGKKSSVILXSEAAMMDQVNRAQGEAEAILARAQATAKGLXLVSQSLKEXGGXEAASLRVAEQYIXAF
GNIAKEGTTMLLPSXAXNPASMIAQAL

Alternative bases

Position 3 may also show V, T or A. Position 36 may also show V or M. Position 96 may also show L, V or M. Position 182 may also show S.

SEQUENCE LISTING

<160> NUMBER OF SEQ ID NOS: 20

<210> SEQ ID NO 1
<211> LENGTH: 2738
<212> TYPE: DNA
<213> ORGANISM: Hordeum vulgare
<220> FEATURE:
<221> NAME/KEY: misc_feature
<222> LOCATION: (1)..(2738)
<223> OTHER INFORMATION: cDNA of HvStm1
<220> FEATURE:
<221> NAME/KEY: CDS
<222> LOCATION: (48)..(1127)
<220> FEATURE:
<221> NAME/KEY: misc_feature
<222> LOCATION: (156)..(158)
<223> OTHER INFORMATION: Xaa encoded is Trp or Leu
<220> FEATURE:
<221> NAME/KEY: misc_feature
<222> LOCATION: (180)..(182)
<223> OTHER INFORMATION: Xaa encoded is Ala or Val
<220> FEATURE:
<221> NAME/KEY: misc_feature
<222> LOCATION: (471)..(473)
<223> OTHER INFORMATION: Xaa encoded is Glu or Lys

<400> SEQUENCE: 1

```
ataaaataaa tttcctcttc ctctcgactc ggatcgactc gactccg atg gcg atg         56
                                                  Met Ala Met
                                                   1 tcg acg gcg acc cgg atg ctg gcg cgc cgc gcc gtc ccc ggc cac ctc        104
Ser Thr Ala Thr Arg Met Leu Ala Arg Arg Ala Val Pro Gly His Leu
      5                  10                  15 ctc cgc aac gcc aac ccc gca gcc gcg acg gcg gct ctg ctg caa cgg        152
Leu Arg Asn Ala Asn Pro Ala Ala Ala Thr Ala Ala Leu Leu Gln Arg
 20                  25                  30                  35 cgg tkg tac cgc ggg gga gcg gac cct gyg ccg tcc ttg tac cac ccg        200
Arg Xaa Tyr Arg Gly Gly Ala Asp Pro Xaa Pro Ser Leu Tyr His Pro
                 40                  45                  50 ccg ccg acc ccg gcg aac ctg ggc ctg agc atc gtc ccg gag aag aag        248
Pro Pro Thr Pro Ala Asn Leu Gly Leu Ser Ile Val Pro Glu Lys Lys
             55                  60                  65 gcg ttc gtg gtg gag cgc ttc ggc aag tac ctc aag acg ctg ccg tcg        296
Ala Phe Val Val Glu Arg Phe Gly Lys Tyr Leu Lys Thr Leu Pro Ser
         70                  75                  80 ggg atc cac ctc ctc atg ccc ggc gtc gac cgc atc gcc tac gtc cac        344
Gly Ile His Leu Leu Met Pro Gly Val Asp Arg Ile Ala Tyr Val His
     85                  90                  95 tcg ctc aag gag gag gcc atc cca atc cca gac aac tcg gca atc aca        392
Ser Leu Lys Glu Glu Ala Ile Pro Ile Pro Asp Asn Ser Ala Ile Thr
100                 105                 110                 115 aag gac aac gta tca ata cag atc gga gga gtg cta tac gtc aag atc        440
Lys Asp Asn Val Ser Ile Gln Ile Gly Gly Val Leu Tyr Val Lys Ile
                 120                 125                 130 gtc gac ccc tac atg gcc tcg tac ggc gtc rag aac ccc atc tat gct        488
Val Asp Pro Tyr Met Ala Ser Tyr Gly Val Xaa Asn Pro Ile Tyr Ala
             135                 140                 145 gtc atc cag ctt gcc cag aca aca atg agg agt gag ctt ggc aag atc        536
Val Ile Gln Leu Ala Gln Thr Thr Met Arg Ser Glu Leu Gly Lys Ile
         150                 155                 160 acc ctc gac aag acc ttc gag gag agg gac acg ctc aac tta aac att        584
Thr Leu Asp Lys Thr Phe Glu Glu Arg Asp Thr Leu Asn Leu Asn Ile
    165                 170                 175 gtg aag tca atc aat gag gca gct gaa act tgg ggt ttg aag tgt ctt        632
```

```
Val Lys Ser Ile Asn Glu Ala Ala Glu Thr Trp Gly Leu Lys Cys Leu
180                 185                 190                 195 cgc tac gaa atc agg gac atc act cct cca gat gga gtc aag aag gcc    680
Arg Tyr Glu Ile Arg Asp Ile Thr Pro Pro Asp Gly Val Lys Lys Ala
                200                 205                 210 atg gag atg cag gcc gca gca gag cgc aag aaa cgt gct cag atc ctt    728
Met Glu Met Gln Ala Ala Ala Glu Arg Lys Lys Arg Ala Gln Ile Leu
            215                 220                 225 gag tct gaa ggt gct atg atg gaa aaa gca aac aga gca aag ggt gaa    776
Glu Ser Glu Gly Ala Met Met Glu Lys Ala Asn Arg Ala Lys Gly Glu
        230                 235                 240 gct gaa gcg att ctt gcc agg tca caa gcc act gct gaa ggg atc agg    824
Ala Glu Ala Ile Leu Ala Arg Ser Gln Ala Thr Ala Glu Gly Ile Arg
    245                 250                 255 atg gtc tct gag tcg ttt aaa act gaa ggc agc aca gag gct gcc agc    872
Met Val Ser Glu Ser Phe Lys Thr Glu Gly Ser Thr Glu Ala Ala Ser
260                 265                 270                 275 ttg agg att gct gaa cag tac atc aga gca ttc agt gaa ctg gct aga    920
Leu Arg Ile Ala Glu Gln Tyr Ile Arg Ala Phe Ser Glu Leu Ala Arg
                280                 285                 290 act acg aac acg atg ctc ctc ccc agc gac gca ggc aat ccg ggg aca    968
Thr Thr Asn Thr Met Leu Leu Pro Ser Asp Ala Gly Asn Pro Gly Thr
                295                 300                 305 atg att gct cag gcc ctt cag ata tac aac cac acg tac aag cag aaa   1016
Met Ile Ala Gln Ala Leu Gln Ile Tyr Asn His Thr Tyr Lys Gln Lys
            310                 315                 320 ctg acg ctg gga agc ccc agc ccc agc aag cag gcg gtg gcg gca gaa   1064
Leu Thr Leu Gly Ser Pro Ser Pro Ser Lys Gln Ala Val Ala Ala Glu
        325                 330                 335 gag gct gat ttg tcc ctt ggg atg cca tcc gtg agc gac ctc ggc acc   1112
Glu Ala Asp Leu Ser Leu Gly Met Pro Ser Val Ser Asp Leu Gly Thr
340                 345                 350                 355 ttt ccg cac cag aag taaagcagtt ttttttttt tttactgttt tgttagggag    1167
Phe Pro His Gln Lys
                360 gaatggatag ctagactgga tagatagatt gctagggagg cagtgcaact gggtcacgag   1227 tgaagatttg ctgattaggt aggtcggtcg gttaggagca gcttgagagc aagcttttg    1287 tgtgtctata tgaatgggtg gtgttagatg cagaaccttt gaatatgttg catgagatat   1347 ttgcggtttt ggtctttaaa aaataaaata aatttcctct tcctctcgac tcggatcgac   1407 tcgactccga tggcgatgtc gacggcgacc cggatgctgg cgcgccgcgc cgtcccggc    1467 cacctcctcc gcaacgccaa ccccgcagcc gcgacggcgg ctctgctgca acggcggtkg   1527 taccgcgggg gagcggaccc tgygccgtcc ttgtaccacc cgccgccgac cccggcgaac   1587 ctgggcctga gcatcgtccc ggagaagaag gcgttcgtgg tggagcgctt cggcaagtac   1647 ctcaagacgc tgccgtcggg gatccacctc tcatgcccg gcgtcgaccg catcgcctac   1707 gtccactcgc tcaaggagga ggccatccca atcccagaca actcggcaat acaaaggac    1767 aacgtatcaa tacagatcgg aggagtgcta tacgtcaaga tcgtcgaccc ctacatggcc   1827 tcgtacggcg tcragaaccc catctatgct gtcatccagc ttgcccagac aacaatgagg   1887 agtgagcttg gcaagatcac cctcgacaag accttcgagg agagggacac gctcaactta   1947 aacattgtga agtcaatcaa tgaggcagct gaaacttggg gtttgaagtg tcttcgctac   2007 gaaatcaggg acatcactcc tccagatgga gtcaagaagg ccatggagat gcaggccgca   2067 gcagagcgca agaaacgtgc tcagatcctt gagtctgaag gtgctatgat ggaaaaagca   2127 aacagagcaa agggtgaagc tgaagcgatt cttgccaggt cacaagccac tgctgaaggg   2187
```

-continued

```
atcaggatgg tctctgagtc gtttaaaact gaaggcagca cagaggctgc cagcttgagg    2247
attgctgaac agtacatcag agcattcagt gaactggcta gaactacgaa cacgatgctt    2307
ctccccagcg acgcaggcaa tccgggggaca atgattgctc aggcccttca gatatacaac    2367
cacacgtaca agcagaaact gacgctggga agccccagcc ccagcaagca ggcggtggcg    2427
gcagaagagg ctgatttgtc ccttgggatg ccatccgtga gcgacctcgg cacctttccg    2487
caccagaagt aaagcagttt ttttttttt ttactgtttt gttagggagg aatggatagc    2547
tagactggat agatagattg ctagggaggc agtgcaactg ggtcacgagt gaagatttgc    2607
tgattaggta ggtcggtcgg ttaggagcag cttgagagca agcttttgt gtgtctatat    2667 gaatgggtgg tgttagatgc agaacctttg aatatgttgc atgagatatt tgcggttttg    2727
gtctttaaaa a                                                          2738
```

<210> SEQ ID NO 2
<211> LENGTH: 360
<212> TYPE: PRT
<213> ORGANISM: Hordeum vulgare
<220> FEATURE:
<221> NAME/KEY: misc_feature
<222> LOCATION: (37)..(37)
<223> OTHER INFORMATION: The 'Xaa' at location 37 stands for Trp, or Leu.
<220> FEATURE:
<221> NAME/KEY: misc_feature
<222> LOCATION: (45)..(45)
<223> OTHER INFORMATION: The 'Xaa' at location 45 stands for Ala, or Val.
<220> FEATURE:
<221> NAME/KEY: misc_feature
<222> LOCATION: (142)..(142)
<223> OTHER INFORMATION: The 'Xaa' at location 142 stands for Glu, or Lys.

<400> SEQUENCE: 2

```
Met Ala Met Ser Thr Ala Thr Arg Met Leu Ala Arg Arg Ala Val Pro
1               5                   10                  15

Gly His Leu Leu Arg Asn Ala Asn Pro Ala Ala Ala Thr Ala Ala Leu
            20                  25                  30

Leu Gln Arg Arg Xaa Tyr Arg Gly Gly Ala Asp Pro Xaa Pro Ser Leu
        35                  40                  45

Tyr His Pro Pro Thr Pro Ala Asn Leu Gly Leu Ser Ile Val Pro
    50                  55                  60

Glu Lys Lys Ala Phe Val Val Glu Arg Phe Gly Lys Tyr Leu Lys Thr
65                  70                  75                  80

Leu Pro Ser Gly Ile His Leu Leu Met Pro Gly Val Asp Arg Ile Ala
                85                  90                  95

Tyr Val His Ser Leu Lys Glu Glu Ala Ile Pro Ile Pro Asp Asn Ser
            100                 105                 110

Ala Ile Thr Lys Asp Asn Val Ser Ile Gln Ile Gly Gly Val Leu Tyr
        115                 120                 125

Val Lys Ile Val Asp Pro Tyr Met Ala Ser Tyr Gly Val Xaa Asn Pro
    130                 135                 140

Ile Tyr Ala Val Ile Gln Leu Ala Gln Thr Thr Met Arg Ser Glu Leu
145                 150                 155                 160

Gly Lys Ile Thr Leu Asp Lys Thr Phe Glu Glu Arg Asp Thr Leu Asn
                165                 170                 175

Leu Asn Ile Val Lys Ser Ile Asn Glu Ala Ala Glu Thr Trp Gly Leu
            180                 185                 190
```

```
Lys Cys Leu Arg Tyr Glu Ile Arg Asp Ile Thr Pro Pro Asp Gly Val
            195                 200                 205

Lys Lys Ala Met Glu Met Gln Ala Ala Ala Glu Arg Lys Lys Arg Ala
210                 215                 220

Gln Ile Leu Glu Ser Glu Gly Ala Met Met Glu Lys Ala Asn Arg Ala
225                 230                 235                 240

Lys Gly Glu Ala Glu Ala Ile Leu Ala Arg Ser Gln Ala Thr Ala Glu
            245                 250                 255

Gly Ile Arg Met Val Ser Glu Ser Phe Lys Thr Glu Gly Ser Thr Glu
            260                 265                 270

Ala Ala Ser Leu Arg Ile Ala Glu Gln Tyr Ile Arg Ala Phe Ser Glu
            275                 280                 285

Leu Ala Arg Thr Thr Asn Thr Met Leu Leu Pro Ser Asp Ala Gly Asn
290                 295                 300

Pro Gly Thr Met Ile Ala Gln Ala Leu Gln Ile Tyr Asn His Thr Tyr
305                 310                 315                 320

Lys Gln Lys Leu Thr Leu Gly Ser Pro Ser Pro Ser Lys Gln Ala Val
            325                 330                 335

Ala Ala Glu Glu Ala Asp Leu Ser Leu Gly Met Pro Ser Val Ser Asp
            340                 345                 350

Leu Gly Thr Phe Pro His Gln Lys
            355                 360

<210> SEQ ID NO 3
<211> LENGTH: 1134
<212> TYPE: DNA
<213> ORGANISM: Oryza sativa (japonica cultivar-group)
<220> FEATURE:
<221> NAME/KEY: CDS
<222> LOCATION: (1)..(1134)
<220> FEATURE:
<221> NAME/KEY: misc_feature
<222> LOCATION: (1)..(1134)
<223> OTHER INFORMATION: putative Band 7 protein. ACCESSION   XP_480193.
      VERSION      XP_480193.1  GI:50941331.
      DBSOURCE     REFSEQ: accession XM_480193.1.

<400> SEQUENCE: 3 atg gcg acg ctc ctc cgg cga tcc gtc ggc ccc gcg cgc cag ctc ctc     48
Met Ala Thr Leu Leu Arg Arg Ser Val Gly Pro Ala Arg Gln Leu Leu
1               5                   10                  15 ctc cgc ccg cgc ccg ctc ccg ctc ccc cac gcc gcc tcc tcc acc cgc     96
Leu Arg Pro Arg Pro Leu Pro Leu Pro His Ala Ala Ser Ser Thr Arg
            20                  25                  30 tcc ttc tcc cgc tac tac tcc cgc gac gac gtc tcg agg tac gag gcg    144
Ser Phe Ser Arg Tyr Tyr Ser Arg Asp Asp Val Ser Arg Tyr Glu Ala
        35                  40                  45 ctg agc acg ccg gtg aac tgg ggg gtg agc atc gtg ccg gag aag aag    192
Leu Ser Thr Pro Val Asn Trp Gly Val Ser Ile Val Pro Glu Lys Lys
50                  55                  60 gcg ttc gtg gtg gag cgg ttc ggc aag tac gtc aag acg ctc ggc tcc    240
Ala Phe Val Val Glu Arg Phe Gly Lys Tyr Val Lys Thr Leu Gly Ser
65                  70                  75                  80 ggg atc cac gtg ctc gtc ccc ctc gtc gac cgc atc gcc tac gtc cac    288
Gly Ile His Val Leu Val Pro Leu Val Asp Arg Ile Ala Tyr Val His
                85                  90                  95 tcg ctc aag gag gag gcc atc ccc atc ccc gac cag tcc gcc atc acc    336
Ser Leu Lys Glu Glu Ala Ile Pro Ile Pro Asp Gln Ser Ala Ile Thr
            100                 105                 110 aag gac aac gtc tcc atc cag atc gac ggc gtc ctc tac gtc aag att    384
Lys Asp Asn Val Ser Ile Gln Ile Asp Gly Val Leu Tyr Val Lys Ile
```

```
                115                 120                 125
gtt gat ccc tac ctt gct tcc tat ggt gtg gag aat cca att ttt gca      432
Val Asp Pro Tyr Leu Ala Ser Tyr Gly Val Glu Asn Pro Ile Phe Ala
130                 135                 140 gtc ata cag ctt gcc caa aca act atg aga agt gag ctt gga aag att      480
Val Ile Gln Leu Ala Gln Thr Thr Met Arg Ser Glu Leu Gly Lys Ile
145                 150                 155                 160 acg cta gac aag act ttt gag gag agg gat aca cta aat gag caa att      528
Thr Leu Asp Lys Thr Phe Glu Glu Arg Asp Thr Leu Asn Glu Gln Ile
                165                 170                 175 gtg agg tcc att aat gag gct gca act gat tgg gga ctg aaa tgc ctc      576
Val Arg Ser Ile Asn Glu Ala Ala Thr Asp Trp Gly Leu Lys Cys Leu
            180                 185                 190 cgt tat gag atc agg gat ata tct ccg cca cgt ggt gtt aag gtg gct      624
Arg Tyr Glu Ile Arg Asp Ile Ser Pro Pro Arg Gly Val Lys Val Ala
        195                 200                 205 atg gag atg caa gca gaa gca gaa agg aaa aag cgt gcc caa atc ctt      672
Met Glu Met Gln Ala Glu Ala Glu Arg Lys Lys Arg Ala Gln Ile Leu
210                 215                 220 gaa tca gaa ggt gct atg ttg gat cag gca aat cgc gca aag ggt gag      720
Glu Ser Glu Gly Ala Met Leu Asp Gln Ala Asn Arg Ala Lys Gly Glu
225                 230                 235                 240 gct gaa gca att ctt gca aag tct gaa gca act gct cga gga atc aga      768
Ala Glu Ala Ile Leu Ala Lys Ser Glu Ala Thr Ala Arg Gly Ile Arg
                245                 250                 255 ttg gtc tct gag gcc atg agg acc aag ggc agc act gag gct gcg aac      816
Leu Val Ser Glu Ala Met Arg Thr Lys Gly Ser Thr Glu Ala Ala Asn
            260                 265                 270 ctg aga gtt gct gaa caa tac atg aag gca ttt gct aat ctg gcc aaa      864
Leu Arg Val Ala Glu Gln Tyr Met Lys Ala Phe Ala Asn Leu Ala Lys
        275                 280                 285 aag agc aac acg att ctc ctt cca agt gac gct ggc aac cca tca tcc      912
Lys Ser Asn Thr Ile Leu Leu Pro Ser Asp Ala Gly Asn Pro Ser Ser
290                 295                 300 ctc atc gcc cag tct ctc cag ata tac aag cac atc tgc cag acc aac      960
Leu Ile Ala Gln Ser Leu Gln Ile Tyr Lys His Ile Cys Gln Thr Asn
305                 310                 315                 320 agc ttg aag agt ggg aag tac ctc aca gat gct cta gag gag acg gaa     1008
Ser Leu Lys Ser Gly Lys Tyr Leu Thr Asp Ala Leu Glu Glu Thr Glu
                325                 330                 335 ccg gag gaa gaa gag ttg gac tct act gac cta cct tct ctg agc agc     1056
Pro Glu Glu Glu Glu Leu Asp Ser Thr Asp Leu Pro Ser Leu Ser Ser
            340                 345                 350 ggg atg ccg tcc ccc gac atg cca gat gac cat gac aag act ttc tcc     1104
Gly Met Pro Ser Pro Asp Met Pro Asp Asp His Asp Lys Thr Phe Ser
        355                 360                 365 ctg cag cgc cgc aac aag gac aag cac tga                             1134
Leu Gln Arg Arg Asn Lys Asp Lys His
370                 375

<210> SEQ ID NO 4
<211> LENGTH: 377
<212> TYPE: PRT
<213> ORGANISM: Oryza sativa (japonica cultivar-group)
<220> FEATURE:
<221> NAME/KEY: misc_feature
<222> LOCATION: (1)..(1134)
<223> OTHER INFORMATION: putative Band 7 protein. ACCESSION   XP_480193.
      VERSION    XP_480193.1  GI:50941331.
      DBSOURCE   REFSEQ: accession XM_480193.1.

<400> SEQUENCE: 4
```

```
Met Ala Thr Leu Leu Arg Arg Ser Val Gly Pro Ala Arg Gln Leu Leu
1               5                   10                  15

Leu Arg Pro Arg Pro Leu Pro Leu Pro His Ala Ala Ser Ser Thr Arg
            20                  25                  30

Ser Phe Ser Arg Tyr Tyr Ser Arg Asp Asp Val Ser Arg Tyr Glu Ala
        35                  40                  45

Leu Ser Thr Pro Val Asn Trp Gly Val Ser Ile Val Pro Glu Lys Lys
    50                  55                  60

Ala Phe Val Val Glu Arg Phe Gly Lys Tyr Val Lys Thr Leu Gly Ser
65                  70                  75                  80

Gly Ile His Val Leu Val Pro Leu Val Asp Arg Ile Ala Tyr Val His
                85                  90                  95

Ser Leu Lys Glu Glu Ala Ile Pro Ile Pro Asp Gln Ser Ala Ile Thr
            100                 105                 110

Lys Asp Asn Val Ser Ile Gln Ile Asp Gly Val Leu Tyr Val Lys Ile
        115                 120                 125

Val Asp Pro Tyr Leu Ala Ser Tyr Gly Val Glu Asn Pro Ile Phe Ala
    130                 135                 140

Val Ile Gln Leu Ala Gln Thr Thr Met Arg Ser Glu Leu Gly Lys Ile
145                 150                 155                 160

Thr Leu Asp Lys Thr Phe Glu Glu Arg Asp Thr Leu Asn Glu Gln Ile
                165                 170                 175

Val Arg Ser Ile Asn Glu Ala Ala Thr Asp Trp Gly Leu Lys Cys Leu
            180                 185                 190

Arg Tyr Glu Ile Arg Asp Ile Ser Pro Pro Arg Gly Val Lys Val Ala
        195                 200                 205

Met Glu Met Gln Ala Glu Ala Glu Arg Lys Lys Arg Ala Gln Ile Leu
210                 215                 220

Glu Ser Glu Gly Ala Met Leu Asp Gln Ala Asn Arg Ala Lys Gly Glu
225                 230                 235                 240

Ala Glu Ala Ile Leu Ala Lys Ser Glu Ala Thr Ala Arg Gly Ile Arg
                245                 250                 255

Leu Val Ser Glu Ala Met Arg Thr Lys Gly Ser Thr Glu Ala Ala Asn
            260                 265                 270

Leu Arg Val Ala Glu Gln Tyr Met Lys Ala Phe Ala Asn Leu Ala Lys
        275                 280                 285

Lys Ser Asn Thr Ile Leu Leu Pro Ser Asp Ala Gly Asn Pro Ser Ser
290                 295                 300

Leu Ile Ala Gln Ser Leu Gln Ile Tyr Lys His Ile Cys Gln Thr Asn
305                 310                 315                 320

Ser Leu Lys Ser Gly Lys Tyr Leu Thr Asp Ala Leu Glu Glu Thr Glu
                325                 330                 335

Pro Glu Glu Glu Glu Leu Asp Ser Thr Asp Leu Pro Ser Leu Ser Ser
            340                 345                 350

Gly Met Pro Ser Pro Asp Met Pro Asp Asp His Asp Lys Thr Phe Ser
        355                 360                 365

Leu Gln Arg Arg Asn Lys Asp Lys His
370                 375
```

<210> SEQ ID NO 5
<211> LENGTH: 1185
<212> TYPE: DNA
<213> ORGANISM: Zea mays
<220> FEATURE:
<221> NAME/KEY: CDS
<222> LOCATION: (1)..(1185)

```
<220> FEATURE:
<221> NAME/KEY: misc_feature
<222> LOCATION: (1)..(1185)
<223> OTHER INFORMATION: stomatin-like protein [Zea mays]. ACCESSION
      AAF68388
      VERSION     AAF68388.1  GI:7716464
      DBSOURCE    accession AF236372.1

<400> SEQUENCE: 5
```

| | | | | | | | | | | | | | | | | |
|---|---|---|---|---|---|---|---|---|---|---|---|---|---|---|---|---|
| atg | gca | agc | cta | ctc | cgg | cga | tct | gcc | gta | ccc | gcg | cgc | cag | ctc | ctc | 48 |
| Met | Ala | Ser | Leu | Leu | Arg | Arg | Ser | Ala | Val | Pro | Ala | Arg | Gln | Leu | Leu | |
| 1 | | | | 5 | | | | | 10 | | | | | 15 | | |
| ctc | ctc | ccg | cgc | cat | ttc | gcc | gcc | gcc | ggc | tcc | gcc | ccc | gcc | ttg | tcc | 96 |
| Leu | Leu | Pro | Arg | His | Phe | Ala | Ala | Ala | Gly | Ser | Ala | Pro | Ala | Leu | Ser | |
| | | | 20 | | | | | 25 | | | | | 30 | | | |
| cgc | tcg | ttc | tcc | cgc | ttc | aac | ccc | cga | gac | gac | agc | tct | atg | ttc | gat | 144 |
| Arg | Ser | Phe | Ser | Arg | Phe | Asn | Pro | Arg | Asp | Asp | Ser | Ser | Met | Phe | Asp | |
| | 35 | | | | | 40 | | | | | 45 | | | | | |
| cca | ccg | gag | ccg | ccg | gtg | aac | tgg | ggc | gtg | agc | ata | gtt | ccg | gag | aag | 192 |
| Pro | Pro | Glu | Pro | Pro | Val | Asn | Trp | Gly | Val | Ser | Ile | Val | Pro | Glu | Lys | |
| 50 | | | | | 55 | | | | | 60 | | | | | | |
| aag | gct | tac | gtt | gtg | gag | aga | ttc | ggg | aag | tat | ctc | aag | acc | ctc | ggc | 240 |
| Lys | Ala | Tyr | Val | Val | Glu | Arg | Phe | Gly | Lys | Tyr | Leu | Lys | Thr | Leu | Gly | |
| 65 | | | | | 70 | | | | | 75 | | | | | 80 | |
| tcc | ggg | ttc | cac | ctc | ctg | atc | ccc | gcc | gtc | gac | cgt | att | gcc | tac | gtg | 288 |
| Ser | Gly | Phe | His | Leu | Leu | Ile | Pro | Ala | Val | Asp | Arg | Ile | Ala | Tyr | Val | |
| | | | | 85 | | | | | 90 | | | | | 95 | | |
| cac | tcg | ctc | aag | gaa | gag | acc | atc | cct | atc | cct | cac | cag | aac | gcc | atc | 336 |
| His | Ser | Leu | Lys | Glu | Glu | Thr | Ile | Pro | Ile | Pro | His | Gln | Asn | Ala | Ile | |
| | | | 100 | | | | | 105 | | | | | 110 | | | |
| acc | aag | gac | aac | gtc | acc | ata | cag | att | gac | agc | gtc | atc | tat | gtc | aag | 384 |
| Thr | Lys | Asp | Asn | Val | Thr | Ile | Gln | Ile | Asp | Ser | Val | Ile | Tyr | Val | Lys | |
| | | 115 | | | | | 120 | | | | | 125 | | | | |
| atc | atg | gac | ccc | tac | ctt | gct | tcc | tat | ggt | gtg | gag | aat | cca | atc | tat | 432 |
| Ile | Met | Asp | Pro | Tyr | Leu | Ala | Ser | Tyr | Gly | Val | Glu | Asn | Pro | Ile | Tyr | |
| | 130 | | | | | 135 | | | | | 140 | | | | | |
| gct | gtc | cta | caa | ctt | gca | caa | aca | acc | atg | aga | agt | gaa | ctc | ggg | aag | 480 |
| Ala | Val | Leu | Gln | Leu | Ala | Gln | Thr | Thr | Met | Arg | Ser | Glu | Leu | Gly | Lys | |
| 145 | | | | | 150 | | | | | 155 | | | | | 160 | |
| ata | acc | tta | gat | aag | act | ttt | gag | gag | aga | gat | gca | tta | aat | gag | aaa | 528 |
| Ile | Thr | Leu | Asp | Lys | Thr | Phe | Glu | Glu | Arg | Asp | Ala | Leu | Asn | Glu | Lys | |
| | | | | 165 | | | | | 170 | | | | | 175 | | |
| att | gtg | agt | gcc | atc | aat | gaa | gca | gcc | aca | gat | tgg | ggc | ctg | aag | tgt | 576 |
| Ile | Val | Ser | Ala | Ile | Asn | Glu | Ala | Ala | Thr | Asp | Trp | Gly | Leu | Lys | Cys | |
| | | | 180 | | | | | 185 | | | | | 190 | | | |
| atc | cgc | tat | gag | atc | agg | gac | ata | aat | cct | cca | gca | ggg | att | agg | cag | 624 |
| Ile | Arg | Tyr | Glu | Ile | Arg | Asp | Ile | Asn | Pro | Pro | Ala | Gly | Ile | Arg | Gln | |
| | | 195 | | | | | 200 | | | | | 205 | | | | |
| gct | atg | gag | atg | cag | gct | gag | gca | gaa | agg | aaa | aaa | cgc | gct | caa | atc | 672 |
| Ala | Met | Glu | Met | Gln | Ala | Glu | Ala | Glu | Arg | Lys | Lys | Arg | Ala | Gln | Ile | |
| | 210 | | | | | 215 | | | | | 220 | | | | | |
| ctt | gag | tca | gaa | ggg | atg | aaa | cag | gcc | caa | atc | ctt | gaa | tca | gaa | ggg | 720 |
| Leu | Glu | Ser | Glu | Gly | Met | Lys | Gln | Ala | Gln | Ile | Leu | Glu | Ser | Glu | Gly | |
| 225 | | | | | 230 | | | | | 235 | | | | | 240 | |
| aaa | aag | act | gcc | cag | atc | ctt | gaa | tct | gaa | gga | gct | atg | ttg | gat | cta | 768 |
| Lys | Lys | Thr | Ala | Gln | Ile | Leu | Glu | Ser | Glu | Gly | Ala | Met | Leu | Asp | Leu | |
| | | | | 245 | | | | | 250 | | | | | 255 | | |
| gca | aac | cgt | gcc | aag | ggt | gcg | gct | gaa | gca | att | ctt | gcc | aag | tca | gaa | 816 |
| Ala | Asn | Arg | Ala | Lys | Gly | Ala | Ala | Glu | Ala | Ile | Leu | Ala | Lys | Ser | Glu | |
| | | | 260 | | | | | 265 | | | | | 270 | | | |
| gct | act | gct | cgt | gga | atg | aga | ttg | gtt | tca | gat | gcg | atg | aca | act | gaa | 864 |
| Ala | Thr | Ala | Arg | Gly | Met | Arg | Leu | Val | Ser | Asp | Ala | Met | Thr | Thr | Glu | |

-continued

```
              275                 280                 285
ggc agt gcc aag gct gct agc ctg aaa ctt gca gag caa tac atc gaa       912
Gly Ser Ala Lys Ala Ala Ser Leu Lys Leu Ala Glu Gln Tyr Ile Glu
    290                 295                 300 gca ttc tca aat ctg gca caa aag aca aat aca atg ctt ctt cca ggt       960
Ala Phe Ser Asn Leu Ala Gln Lys Thr Asn Thr Met Leu Leu Pro Gly
305                 310                 315                 320 gat agt gcc agc cca gca tct ttc gtg gcc cag gca atg aag acg tat      1008
Asp Ser Ala Ser Pro Ala Ser Phe Val Ala Gln Ala Met Lys Thr Tyr
                325                 330                 335 gag caa atc cat tcc cac agc cag gca tta aag agc cac ccc cag ata      1056
Glu Gln Ile His Ser His Ser Gln Ala Leu Lys Ser His Pro Gln Ile
        340                 345                 350 gaa gag ctg aag gaa tca gga gag acc agt cct gct cca tct tct gag      1104
Glu Glu Leu Lys Glu Ser Gly Glu Thr Ser Pro Ala Pro Ser Ser Glu
    355                 360                 365 gcg agc aag aca cca cca ctc att gag gaa gca gat tct aac cag acc      1152
Ala Ser Lys Thr Pro Pro Leu Ile Glu Glu Ala Asp Ser Asn Gln Thr
370                 375                 380 ttc tca ctg caa cgc ccc aag aac aag cag tga                          1185
Phe Ser Leu Gln Arg Pro Lys Asn Lys Gln
385                 390
```

<210> SEQ ID NO 6
<211> LENGTH: 394
<212> TYPE: PRT
<213> ORGANISM: Zea mays
<220> FEATURE:
<221> NAME/KEY: misc_feature
<222> LOCATION: (1)..(1185)
<223> OTHER INFORMATION: stomatin-like protein [Zea mays]. ACCESSION
      AAF68388
      VERSION       AAF68388.1  GI:7716464
      DBSOURCE      accession AF236372.1

<400> SEQUENCE: 6

```
Met Ala Ser Leu Leu Arg Arg Ser Ala Val Pro Ala Arg Gln Leu Leu
1               5                   10                  15

Leu Leu Pro Arg His Phe Ala Ala Gly Ser Ala Pro Ala Leu Ser
            20                  25                  30

Arg Ser Phe Ser Arg Phe Asn Pro Arg Asp Asp Ser Ser Met Phe Asp
        35                  40                  45

Pro Pro Glu Pro Pro Val Asn Trp Gly Val Ser Ile Val Pro Glu Lys
    50                  55                  60

Lys Ala Tyr Val Val Glu Arg Phe Gly Lys Tyr Leu Lys Thr Leu Gly
65                  70                  75                  80

Ser Gly Phe His Leu Leu Ile Pro Ala Val Asp Arg Ile Ala Tyr Val
                85                  90                  95

His Ser Leu Lys Glu Glu Thr Ile Pro Ile Pro His Gln Asn Ala Ile
            100                 105                 110

Thr Lys Asp Asn Val Thr Ile Gln Ile Asp Ser Val Ile Tyr Val Lys
        115                 120                 125

Ile Met Asp Pro Tyr Leu Ala Ser Tyr Gly Val Glu Asn Pro Ile Tyr
    130                 135                 140

Ala Val Leu Gln Leu Ala Gln Thr Thr Met Arg Ser Glu Leu Gly Lys
145                 150                 155                 160

Ile Thr Leu Asp Lys Thr Phe Glu Glu Arg Asp Ala Leu Asn Glu Lys
                165                 170                 175

Ile Val Ser Ala Ile Asn Glu Ala Ala Thr Asp Trp Gly Leu Lys Cys
            180                 185                 190
```

-continued

```
Ile Arg Tyr Glu Ile Arg Asp Ile Asn Pro Pro Ala Gly Ile Arg Gln
            195                 200                 205
Ala Met Glu Met Gln Ala Glu Ala Glu Arg Lys Lys Arg Ala Gln Ile
        210                 215                 220
Leu Glu Ser Glu Gly Met Lys Gln Ala Gln Ile Leu Glu Ser Glu Gly
225                 230                 235                 240
Lys Lys Thr Ala Gln Ile Leu Glu Ser Glu Gly Ala Met Leu Asp Leu
                245                 250                 255
Ala Asn Arg Ala Lys Gly Ala Ala Glu Ala Ile Leu Ala Lys Ser Glu
            260                 265                 270
Ala Thr Ala Arg Gly Met Arg Leu Val Ser Asp Ala Met Thr Thr Glu
        275                 280                 285
Gly Ser Ala Lys Ala Ala Ser Leu Lys Leu Ala Glu Gln Tyr Ile Glu
    290                 295                 300
Ala Phe Ser Asn Leu Ala Gln Lys Thr Asn Thr Met Leu Leu Pro Gly
305                 310                 315                 320
Asp Ser Ala Ser Pro Ala Ser Phe Val Ala Gln Ala Met Lys Thr Tyr
                325                 330                 335
Glu Gln Ile His Ser His Ser Gln Ala Leu Lys Ser His Pro Gln Ile
            340                 345                 350
Glu Glu Leu Lys Glu Ser Gly Glu Thr Ser Pro Ala Pro Ser Ser Glu
        355                 360                 365
Ala Ser Lys Thr Pro Pro Leu Ile Glu Glu Ala Asp Ser Asn Gln Thr
    370                 375                 380
Phe Ser Leu Gln Arg Pro Lys Asn Lys Gln
385                 390
```

```
<210> SEQ ID NO 7
<211> LENGTH: 1548
<212> TYPE: DNA
<213> ORGANISM: Arabidopsis thaliana (thale cress)
<220> FEATURE:
<221> NAME/KEY: CDS
<222> LOCATION: (1)..(1548)
<220> FEATURE:
<221> NAME/KEY: misc_feature
<222> LOCATION: (1)..(1548)
<223> OTHER INFORMATION: putative protein [Arabidopsis thaliana].
      ACCESSION   CAB81408
      VERSION     CAB81408.1  GI:7269612
      DBSOURCE    embl locus ATCHRIV67, accession AL161571.2.
```

```
<400> SEQUENCE: 7 atg aac cac ctc gtt cgt aaa agc tcc gtc ggt tac tcc gcc ttg agg      48
Met Asn His Leu Val Arg Lys Ser Ser Val Gly Tyr Ser Ala Leu Arg
1               5                   10                  15 tcc gtt tcg tac ctc cgt caa tct gcc gtt acc tct cca cct ccg att      96
Ser Val Ser Tyr Leu Arg Gln Ser Ala Val Thr Ser Pro Pro Pro Ile
            20                  25                  30 ttc tcc gcc gcc gct tca acc gtt cgc cag ttc act tcc gcc ggc tat     144
Phe Ser Ala Ala Ala Ser Thr Val Arg Gln Phe Thr Ser Ala Gly Tyr
        35                  40                  45 cct tcc aac agt ttt caa ttg acg ccg ccg acg aat tgg gga atc cgg     192
Pro Ser Asn Ser Phe Gln Leu Thr Pro Pro Thr Asn Trp Gly Ile Arg
    50                  55                  60 ata gtt ccg gag agg aag gcg ttt gtg att gag cga ttc ggt aaa tac     240
Ile Val Pro Glu Arg Lys Ala Phe Val Ile Glu Arg Phe Gly Lys Tyr
65                  70                  75                  80 gct acg acg ttg ccg tcg ggg att cat ttc ctc att ccg ttc gtg gat     288
Ala Thr Thr Leu Pro Ser Gly Ile His Phe Leu Ile Pro Phe Val Asp
```

|          |          |          |          |          |          |          |          |          |          |          |          |          |          |          |          |     |
|----------|----------|----------|----------|----------|----------|----------|----------|----------|----------|----------|----------|----------|----------|----------|----------|-----|
|          |          |          | 85       |          |          |          | 90       |          |          |          | 95       |          |          |          |          |     |
| cgt      | att      | gct      | tat      | gtt      | cat      | tct      | ctc      | aag      | gaa      | gaa      | gct      | atc      | ccg      | att      | ccg      | 336 |
| Arg      | Ile      | Ala      | Tyr      | Val      | His      | Ser      | Leu      | Lys      | Glu      | Glu      | Ala      | Ile      | Pro      | Ile      | Pro      |     |
|          |          |          | 100      |          |          |          | 105      |          |          |          | 110      |          |          |          |          |     |
| aat      | cag      | act      | gcg      | att      | act      | aaa      | gac      | aac      | gtt      | agt      | atc      | cac      | atc      | gat      | ggt      | 384 |
| Asn      | Gln      | Thr      | Ala      | Ile      | Thr      | Lys      | Asp      | Asn      | Val      | Ser      | Ile      | His      | Ile      | Asp      | Gly      |     |
|          |          | 115      |          |          |          |          | 120      |          |          |          | 125      |          |          |          |          |     |
| gtt      | ctc      | tac      | gtt      | aag      | att      | gtg      | gat      | cct      | aag      | tta      | gct      | tct      | tat      | ggc      | gtt      | 432 |
| Val      | Leu      | Tyr      | Val      | Lys      | Ile      | Val      | Asp      | Pro      | Lys      | Leu      | Ala      | Ser      | Tyr      | Gly      | Val      |     |
|          | 130      |          |          |          |          | 135      |          |          |          | 140      |          |          |          |          |          |     |
| gag      | agt      | cct      | atc      | tat      | gct      | gtt      | gta      | cag      | ctg      | gct      | cag      | acc      | aca      | atg      | cgt      | 480 |
| Glu      | Ser      | Pro      | Ile      | Tyr      | Ala      | Val      | Val      | Gln      | Leu      | Ala      | Gln      | Thr      | Thr      | Met      | Arg      |     |
| 145      |          |          |          | 150      |          |          |          | 155      |          |          |          |          |          |          | 160      |     |
| agt      | gag      | ctt      | ggt      | aag      | atc      | act      | ctt      | gat      | aag      | acc      | ttt      | gag      | gaa      | cga      | gac      | 528 |
| Ser      | Glu      | Leu      | Gly      | Lys      | Ile      | Thr      | Leu      | Asp      | Lys      | Thr      | Phe      | Glu      | Glu      | Arg      | Asp      |     |
|          |          |          |          | 165      |          |          |          | 170      |          |          |          |          |          | 175      |          |     |
| act      | ctc      | aac      | gag      | aag      | ata      | gtg      | gaa      | gcc      | atc      | aat      | gtt      | gct      | gca      | aaa      | gac      | 576 |
| Thr      | Leu      | Asn      | Glu      | Lys      | Ile      | Val      | Glu      | Ala      | Ile      | Asn      | Val      | Ala      | Ala      | Lys      | Asp      |     |
|          |          | 180      |          |          |          |          | 185      |          |          |          | 190      |          |          |          |          |     |
| tgg      | ggt      | ctt      | cag      | tgc      | ctt      | cgt      | tat      | gag      | ata      | agg      | gat      | att      | atg      | ccc      | cct      | 624 |
| Trp      | Gly      | Leu      | Gln      | Cys      | Leu      | Arg      | Tyr      | Glu      | Ile      | Arg      | Asp      | Ile      | Met      | Pro      | Pro      |     |
|          |          | 195      |          |          |          |          | 200      |          |          |          | 205      |          |          |          |          |     |
| cat      | gga      | gtg      | cga      | gct      | gct      | atg      | gaa      | atg      | caa      | gct      | gaa      | gct      | gag      | cgt      | aaa      | 672 |
| His      | Gly      | Val      | Arg      | Ala      | Ala      | Met      | Glu      | Met      | Gln      | Ala      | Glu      | Ala      | Glu      | Arg      | Lys      |     |
|          | 210      |          |          |          |          | 215      |          |          |          | 220      |          |          |          |          |          |     |
| aag      | aga      | gcc      | cag      | att      | ctt      | gag      | tct      | gaa      | gga      | gaa      | agg      | caa      | tcc      | cat      | atc      | 720 |
| Lys      | Arg      | Ala      | Gln      | Ile      | Leu      | Glu      | Ser      | Glu      | Gly      | Glu      | Arg      | Gln      | Ser      | His      | Ile      |     |
| 225      |          |          |          | 230      |          |          |          | 235      |          |          |          |          |          |          | 240      |     |
| aac      | att      | gct      | gat      | ggt      | aag      | aaa      | agt      | tct      | gta      | atc      | ttg      | gca      | tct      | gaa      | gca      | 768 |
| Asn      | Ile      | Ala      | Asp      | Gly      | Lys      | Lys      | Ser      | Ser      | Val      | Ile      | Leu      | Ala      | Ser      | Glu      | Ala      |     |
|          |          |          |          | 245      |          |          |          | 250      |          |          |          |          |          | 255      |          |     |
| gca      | aag      | atg      | gac      | cag      | gtg      | aat      | cga      | gca      | caa      | ggt      | gag      | gca      | gaa      | gca      | ata      | 816 |
| Ala      | Lys      | Met      | Asp      | Gln      | Val      | Asn      | Arg      | Ala      | Gln      | Gly      | Glu      | Ala      | Glu      | Ala      | Ile      |     |
|          |          | 260      |          |          |          |          | 265      |          |          |          | 270      |          |          |          |          |     |
| cta      | gct      | aga      | gca      | caa      | gca      | act      | gcg      | aaa      | ggc      | ctg      | gtc      | ttg      | tta      | tct      | cag      | 864 |
| Leu      | Ala      | Arg      | Ala      | Gln      | Ala      | Thr      | Ala      | Lys      | Gly      | Leu      | Val      | Leu      | Leu      | Ser      | Gln      |     |
|          |          | 275      |          |          |          |          | 280      |          |          |          | 285      |          |          |          |          |     |
| tcc      | ctc      | aag      | gaa      | act      | ggg      | gga      | gta      | gag      | gcg      | gcg      | agt      | ttg      | aga      | gtt      | gca      | 912 |
| Ser      | Leu      | Lys      | Glu      | Thr      | Gly      | Gly      | Val      | Glu      | Ala      | Ala      | Ser      | Leu      | Arg      | Val      | Ala      |     |
|          | 290      |          |          |          |          | 295      |          |          |          | 300      |          |          |          |          |          |     |
| gag      | caa      | tac      | att      | aca      | gcc      | ttc      | ggt      | aac      | att      | gcc      | aag      | gag      | ggt      | acg      | ata      | 960 |
| Glu      | Gln      | Tyr      | Ile      | Thr      | Ala      | Phe      | Gly      | Asn      | Ile      | Ala      | Lys      | Glu      | Gly      | Thr      | Ile      |     |
| 305      |          |          |          | 310      |          |          |          | 315      |          |          |          |          |          |          | 320      |     |
| atg      | ttg      | ctt      | cca      | agt      | ggt      | gct      | tca      | aat      | cct      | gct      | agc      | atg      | att      | gct      | caa      | 1008 |
| Met      | Leu      | Leu      | Pro      | Ser      | Gly      | Ala      | Ser      | Asn      | Pro      | Ala      | Ser      | Met      | Ile      | Ala      | Gln      |     |
|          |          |          |          | 325      |          |          |          | 330      |          |          |          |          |          | 335      |          |     |
| gct      | tta      | aca      | atg      | tac      | aaa      | agc      | ctt      | gtc      | atc      | aat      | ggt      | cca      | agc      | aaa      | gat      | 1056 |
| Ala      | Leu      | Thr      | Met      | Tyr      | Lys      | Ser      | Leu      | Val      | Ile      | Asn      | Gly      | Pro      | Ser      | Lys      | Asp      |     |
|          |          | 340      |          |          |          |          | 345      |          |          |          | 350      |          |          |          |          |     |
| cac      | caa      | gaa      | aca      | caa      | gca      | ctt      | gat      | gaa      | aca      | gat      | ttg      | gaa      | gag      | ttg      | gaa      | 1104 |
| His      | Gln      | Glu      | Thr      | Gln      | Ala      | Leu      | Asp      | Glu      | Thr      | Asp      | Leu      | Glu      | Glu      | Leu      | Glu      |     |
|          |          | 355      |          |          |          |          | 360      |          |          |          | 365      |          |          |          |          |     |
| gac      | atg      | ggt      | gag      | aaa      | cat      | ata      | tca      | gaa      | ggc      | tct      | aat      | aac      | cga      | tca      | ggc      | 1152 |
| Asp      | Met      | Gly      | Glu      | Lys      | His      | Ile      | Ser      | Glu      | Gly      | Ser      | Asn      | Asn      | Arg      | Ser      | Gly      |     |
|          | 370      |          |          |          |          | 375      |          |          |          | 380      |          |          |          |          |          |     |
| tca      | ata      | tca      | ttt      | gac      | aca      | gag      | aaa      | cca      | gct      | ctt      | ccc      | att      | gta      | agt      | ttt      | 1200 |
| Ser      | Ile      | Ser      | Phe      | Asp      | Thr      | Glu      | Lys      | Pro      | Ala      | Leu      | Pro      | Ile      | Val      | Ser      | Phe      |     |
| 385      |          |          |          | 390      |          |          |          | 395      |          |          |          |          |          |          | 400      |     |
| gtt      | ttc      | caa      | act      | aat      | cct      | ttc      | aat      | cca      | aaa      | acc      | atg      | gga      | gcc      | tgt      | gcg      | 1248 |
| Val      | Phe      | Gln      | Thr      | Asn      | Pro      | Phe      | Asn      | Pro      | Lys      | Thr      | Met      | Gly      | Ala      | Cys      | Ala      |     |

```
                    405                 410                 415
agc aaa cct aag gaa tct gac atc gtc gaa ggc tct gtc tcg acc gaa    1296
Ser Lys Pro Lys Glu Ser Asp Ile Val Glu Gly Ser Val Ser Thr Glu
        420                 425                 430 aat gct gtt gtt gag tcc aag aat gcc gcg acc gag aca gat gcc aca    1344
Asn Ala Val Val Glu Ser Lys Asn Ala Ala Thr Glu Thr Asp Ala Thr
            435                 440                 445 tta act cag gag aag aag gaa gag tcc att gaa gag aca aag aag gaa    1392
Leu Thr Gln Glu Lys Lys Glu Glu Ser Ile Glu Glu Thr Lys Lys Glu
    450                 455                 460 ggt gag aca aaa gag gac tcc tct gag gca acc aag gct gag cca act    1440
Gly Glu Thr Lys Glu Asp Ser Ser Glu Ala Thr Lys Ala Glu Pro Thr
465                 470                 475                 480 cca gaa gct gtg aag gca gaa gaa aaa aca tct tct gag act gag cca    1488
Pro Glu Ala Val Lys Ala Glu Glu Lys Thr Ser Ser Glu Thr Glu Pro
                485                 490                 495 cca gca caa gag acc aca cct gct gct aaa acc gat gag gcc cct ctc    1536
Pro Ala Gln Glu Thr Thr Pro Ala Ala Lys Thr Asp Glu Ala Pro Leu
            500                 505                 510 gtg atc ctt tga                                                     1548
Val Ile Leu
        515

<210> SEQ ID NO 8
<211> LENGTH: 515
<212> TYPE: PRT
<213> ORGANISM: Arabidopsis thaliana (thale cress)
<220> FEATURE:
<221> NAME/KEY: misc_feature
<222> LOCATION: (1)..(1548)
<223> OTHER INFORMATION: putative protein [Arabidopsis thaliana].
      ACCESSION   CAB81408
      VERSION     CAB81408.1  GI:7269612
      DBSOURCE    embl locus ATCHRIV67, accession AL161571.2.

<400> SEQUENCE: 8

Met Asn His Leu Val Arg Lys Ser Ser Val Gly Tyr Ser Ala Leu Arg
1               5                   10                  15

Ser Val Ser Tyr Leu Arg Gln Ser Ala Val Thr Ser Pro Pro Ile
            20                  25                  30

Phe Ser Ala Ala Ser Thr Val Arg Gln Phe Thr Ser Ala Gly Tyr
        35                  40                  45

Pro Ser Asn Ser Phe Gln Leu Thr Pro Thr Asn Trp Gly Ile Arg
    50                  55                  60

Ile Val Pro Glu Arg Lys Ala Phe Val Ile Glu Arg Phe Gly Lys Tyr
65                  70                  75                  80

Ala Thr Thr Leu Pro Ser Gly Ile His Phe Leu Ile Pro Phe Val Asp
                85                  90                  95

Arg Ile Ala Tyr Val His Ser Leu Lys Glu Glu Ala Ile Pro Ile Pro
            100                 105                 110

Asn Gln Thr Ala Ile Thr Lys Asp Asn Val Ser Ile His Ile Asp Gly
        115                 120                 125

Val Leu Tyr Val Lys Ile Val Asp Pro Lys Leu Ala Ser Tyr Gly Val
    130                 135                 140

Glu Ser Pro Ile Tyr Ala Val Val Gln Leu Ala Gln Thr Thr Met Arg
145                 150                 155                 160

Ser Glu Leu Gly Lys Ile Thr Leu Asp Lys Thr Phe Glu Glu Arg Asp
                165                 170                 175

Thr Leu Asn Glu Lys Ile Val Glu Ala Ile Asn Val Ala Ala Lys Asp
            180                 185                 190
```

Trp Gly Leu Gln Cys Leu Arg Tyr Glu Ile Arg Asp Ile Met Pro Pro
    195                 200                 205

His Gly Val Arg Ala Ala Met Glu Met Gln Ala Glu Ala Glu Arg Lys
210                 215                 220

Lys Arg Ala Gln Ile Leu Glu Ser Glu Gly Glu Arg Gln Ser His Ile
225                 230                 235                 240

Asn Ile Ala Asp Gly Lys Lys Ser Ser Val Ile Leu Ala Ser Glu Ala
                245                 250                 255

Ala Lys Met Asp Gln Val Asn Arg Ala Gln Gly Glu Ala Glu Ala Ile
            260                 265                 270

Leu Ala Arg Ala Gln Ala Thr Ala Lys Gly Leu Val Leu Leu Ser Gln
        275                 280                 285

Ser Leu Lys Glu Thr Gly Val Glu Ala Ala Ser Leu Arg Val Ala
    290                 295                 300

Glu Gln Tyr Ile Thr Ala Phe Gly Asn Ile Ala Lys Glu Gly Thr Ile
305                 310                 315                 320

Met Leu Leu Pro Ser Gly Ala Ser Asn Pro Ala Ser Met Ile Ala Gln
                325                 330                 335

Ala Leu Thr Met Tyr Lys Ser Leu Val Ile Asn Gly Pro Ser Lys Asp
            340                 345                 350

His Gln Glu Thr Gln Ala Leu Asp Glu Thr Asp Leu Glu Glu Leu Glu
        355                 360                 365

Asp Met Gly Glu Lys His Ile Ser Gly Ser Asn Asn Arg Ser Gly
    370                 375                 380

Ser Ile Ser Phe Asp Thr Glu Lys Pro Ala Leu Pro Ile Val Ser Phe
385                 390                 395                 400

Val Phe Gln Thr Asn Pro Phe Asn Pro Lys Thr Met Gly Ala Cys Ala
                405                 410                 415

Ser Lys Pro Lys Glu Ser Asp Ile Val Glu Gly Ser Val Ser Thr Glu
            420                 425                 430

Asn Ala Val Val Glu Ser Lys Asn Ala Ala Thr Glu Thr Asp Ala Thr
        435                 440                 445

Leu Thr Gln Glu Lys Lys Glu Glu Ser Ile Glu Glu Thr Lys Lys Glu
    450                 455                 460

Gly Glu Thr Lys Glu Asp Ser Ser Glu Ala Thr Lys Ala Glu Pro Thr
465                 470                 475                 480

Pro Glu Ala Val Lys Ala Glu Glu Lys Thr Ser Ser Glu Thr Glu Pro
                485                 490                 495

Pro Ala Gln Glu Thr Thr Pro Ala Ala Lys Thr Asp Glu Ala Pro Leu
            500                 505                 510

Val Ile Leu
        515

<210> SEQ ID NO 9
<211> LENGTH: 1236
<212> TYPE: DNA
<213> ORGANISM: Arabidopsis thaliana (thale cress)
<220> FEATURE:
<221> NAME/KEY: CDS
<222> LOCATION: (1)..(1236)
<220> FEATURE:
<221> NAME/KEY: misc_feature
<222> LOCATION: (1)..(1236)
<223> OTHER INFORMATION: unknown protein [Arabidopsis thaliana].
      ACCESSION   NP_567778
      VERSION     NP_567778.1  GI:18417021
      DBSOURCE    REFSEQ: accession NM_118894.2

<400> SEQUENCE: 9

```
atg aac cac ctc gtt cgt aaa agc tcc gtc ggt tac tcc gcc ttg agg      48
Met Asn His Leu Val Arg Lys Ser Ser Val Gly Tyr Ser Ala Leu Arg
1               5                   10                  15 tcc gtt tcg tac ctc cgt caa tct gcc gtt acc tct cca cct ccg att      96
Ser Val Ser Tyr Leu Arg Gln Ser Ala Val Thr Ser Pro Pro Pro Ile
            20                  25                  30 ttc tcc gcc gcc gct tca acc gtt cgc cag ttc act tcc gcc ggc tat     144
Phe Ser Ala Ala Ala Ser Thr Val Arg Gln Phe Thr Ser Ala Gly Tyr
        35                  40                  45 cct tcc aac agt ttt caa ttg acg ccg ccg acg aat tgg gga atc cgg     192
Pro Ser Asn Ser Phe Gln Leu Thr Pro Pro Thr Asn Trp Gly Ile Arg
    50                  55                  60 ata gtt ccg gag agg aag gcg ttt gtg att gag cga ttc ggt aaa tac     240
Ile Val Pro Glu Arg Lys Ala Phe Val Ile Glu Arg Phe Gly Lys Tyr
65                  70                  75                  80 gct acg acg ttg ccg tcg ggg att cat ttc ctc att ccg ttc gtg gat     288
Ala Thr Thr Leu Pro Ser Gly Ile His Phe Leu Ile Pro Phe Val Asp
                85                  90                  95 cgt att gct tat gtt cat tct ctc aag gaa gaa gct atc ccg att ccg     336
Arg Ile Ala Tyr Val His Ser Leu Lys Glu Glu Ala Ile Pro Ile Pro
            100                 105                 110 aat cag act gcg att act aaa gac aac gtt agt atc cac atc gat ggt     384
Asn Gln Thr Ala Ile Thr Lys Asp Asn Val Ser Ile His Ile Asp Gly
        115                 120                 125 gtt ctc tac gtt aag att gtg gat cct aag tta gct tct tat ggc gtt     432
Val Leu Tyr Val Lys Ile Val Asp Pro Lys Leu Ala Ser Tyr Gly Val
    130                 135                 140 gag agt cct atc tat gct gtt gta cag ctg gct cag acc aca atg cgt     480
Glu Ser Pro Ile Tyr Ala Val Val Gln Leu Ala Gln Thr Thr Met Arg
145                 150                 155                 160 agt gag ctt ggt aag atc act ctt gat aag acc ttt gag gaa cga gac     528
Ser Glu Leu Gly Lys Ile Thr Leu Asp Lys Thr Phe Glu Glu Arg Asp
                165                 170                 175 act ctc aac gag aag ata gtg gaa gcc atc aat gtt gct gca aaa gac     576
Thr Leu Asn Glu Lys Ile Val Glu Ala Ile Asn Val Ala Ala Lys Asp
            180                 185                 190 tgg ggt ctt cag tgc ctt cgt tat gag ata agg gat att atg ccc cct     624
Trp Gly Leu Gln Cys Leu Arg Tyr Glu Ile Arg Asp Ile Met Pro Pro
        195                 200                 205 cat gga gtg cga gct gct atg gaa atg caa gct gaa gct gag cgt aaa     672
His Gly Val Arg Ala Ala Met Glu Met Gln Ala Glu Ala Glu Arg Lys
    210                 215                 220 aag aga gcc cag att ctt gag tct gaa gga gaa agg caa tcc cat atc     720
Lys Arg Ala Gln Ile Leu Glu Ser Glu Gly Glu Arg Gln Ser His Ile
225                 230                 235                 240 aac att gct gat ggt aag aaa agt tct gta atc ttg gca tct gaa gca     768
Asn Ile Ala Asp Gly Lys Lys Ser Ser Val Ile Leu Ala Ser Glu Ala
                245                 250                 255 gca aag atg gac cag gtg aat cga gca caa ggt gag gca gaa gca ata     816
Ala Lys Met Asp Gln Val Asn Arg Ala Gln Gly Glu Ala Glu Ala Ile
            260                 265                 270 cta gct aga gca caa gca act gcg aaa ggc ctg gtc ttg tta tct cag     864
Leu Ala Arg Ala Gln Ala Thr Ala Lys Gly Leu Val Leu Leu Ser Gln
        275                 280                 285 tcc ctc aag gaa act ggg gga gta gag gcg gcg agt ttg aga gtt gca     912
Ser Leu Lys Glu Thr Gly Gly Val Glu Ala Ala Ser Leu Arg Val Ala
    290                 295                 300 gag caa tac att aca gcc ttc ggt aac att gcc aag gag ggt acg ata     960
Glu Gln Tyr Ile Thr Ala Phe Gly Asn Ile Ala Lys Glu Gly Thr Ile
```

```
                305                 310                 315                 320
atg ttg ctt cca agt ggt gct tca aat cct gct agc atg att gct caa         1008
Met Leu Leu Pro Ser Gly Ala Ser Asn Pro Ala Ser Met Ile Ala Gln
                    325                 330                 335 gct tta aca atg tac aaa agc ctt gtc atc aat ggt cca agc aaa gat         1056
Ala Leu Thr Met Tyr Lys Ser Leu Val Ile Asn Gly Pro Ser Lys Asp
            340                 345                 350 cac caa gaa aca caa gca ctt gat gaa aca gat ttg gaa gag ttg gaa         1104
His Gln Glu Thr Gln Ala Leu Asp Glu Thr Asp Leu Glu Glu Leu Glu
        355                 360                 365 gac atg ggt gag aaa cat ata tca gaa ggc tct aat aac cga tca ggc         1152
Asp Met Gly Glu Lys His Ile Ser Glu Gly Ser Asn Asn Arg Ser Gly
370                 375                 380 tca ata tca ttt gac aca gag aaa cca ggt cac acc ggt gaa cca cga         1200
Ser Ile Ser Phe Asp Thr Glu Lys Pro Gly His Thr Gly Glu Pro Arg
385                 390                 395                 400 ttt tct ctt cag aac cgc aac aag gat ccg cag tag                         1236
Phe Ser Leu Gln Asn Arg Asn Lys Asp Pro Gln
                405                 410

<210> SEQ ID NO 10
<211> LENGTH: 411
<212> TYPE: PRT
<213> ORGANISM: Arabidopsis thaliana (thale cress)
<220> FEATURE:
<221> NAME/KEY: misc_feature
<222> LOCATION: (1)..(1236)
<223> OTHER INFORMATION: unknown protein [Arabidopsis thaliana].
      ACCESSION    NP_567778
      VERSION      NP_567778.1  GI:18417021
      DBSOURCE     REFSEQ: accession NM_118894.2

<400> SEQUENCE: 10

Met Asn His Leu Val Arg Lys Ser Ser Val Gly Tyr Ser Ala Leu Arg
1               5                   10                  15

Ser Val Ser Tyr Leu Arg Gln Ser Ala Val Thr Ser Pro Pro Ile
                20                  25                  30

Phe Ser Ala Ala Ala Ser Thr Val Arg Gln Phe Thr Ser Ala Gly Tyr
            35                  40                  45

Pro Ser Asn Ser Phe Gln Leu Thr Pro Thr Asn Trp Gly Ile Arg
        50                  55                  60

Ile Val Pro Glu Arg Lys Ala Phe Val Glu Arg Phe Gly Lys Tyr
65                  70                  75                  80

Ala Thr Thr Leu Pro Ser Gly Ile His Phe Leu Ile Pro Phe Val Asp
                85                  90                  95

Arg Ile Ala Tyr Val His Ser Leu Lys Glu Glu Ala Ile Pro Ile Pro
            100                 105                 110

Asn Gln Thr Ala Ile Thr Lys Asp Asn Val Ser Ile His Ile Asp Gly
        115                 120                 125

Val Leu Tyr Val Lys Ile Asp Pro Lys Leu Ala Ser Tyr Gly Val
            130                 135                 140

Glu Ser Pro Ile Tyr Ala Val Val Gln Leu Ala Gln Thr Thr Met Arg
145                 150                 155                 160

Ser Glu Leu Gly Lys Ile Thr Leu Asp Lys Thr Phe Glu Glu Arg Asp
                165                 170                 175

Thr Leu Asn Glu Lys Ile Val Glu Ala Ile Asn Val Ala Ala Lys Asp
            180                 185                 190

Trp Gly Leu Gln Cys Leu Arg Tyr Glu Ile Arg Asp Ile Met Pro Pro
        195                 200                 205
```

```
His Gly Val Arg Ala Ala Met Glu Met Gln Ala Glu Ala Glu Arg Lys
    210                 215                 220

Lys Arg Ala Gln Ile Leu Glu Ser Glu Gly Glu Arg Gln Ser His Ile
225                 230                 235                 240

Asn Ile Ala Asp Gly Lys Lys Ser Ser Val Ile Leu Ala Ser Glu Ala
                245                 250                 255

Ala Lys Met Asp Gln Val Asn Arg Ala Gln Gly Glu Ala Glu Ala Ile
            260                 265                 270

Leu Ala Arg Ala Gln Ala Thr Ala Lys Gly Leu Val Leu Leu Ser Gln
            275                 280                 285

Ser Leu Lys Glu Thr Gly Gly Val Glu Ala Ala Ser Leu Arg Val Ala
290                 295                 300

Glu Gln Tyr Ile Thr Ala Phe Gly Asn Ile Ala Lys Glu Gly Thr Ile
305                 310                 315                 320

Met Leu Leu Pro Ser Gly Ala Ser Asn Pro Ala Ser Met Ile Ala Gln
                325                 330                 335

Ala Leu Thr Met Tyr Lys Ser Leu Val Ile Asn Gly Pro Ser Lys Asp
            340                 345                 350

His Gln Glu Thr Gln Ala Leu Asp Glu Thr Asp Leu Glu Glu Leu Glu
        355                 360                 365

Asp Met Gly Glu Lys His Ile Ser Gly Ser Asn Asn Arg Ser Gly
370                 375                 380

Ser Ile Ser Phe Asp Thr Glu Lys Pro Gly His Thr Gly Glu Pro Arg
385                 390                 395                 400

Phe Ser Leu Gln Asn Arg Asn Lys Asp Pro Gln
                405                 410

<210> SEQ ID NO 11
<211> LENGTH: 1206
<212> TYPE: DNA
<213> ORGANISM: Arabidopsis thaliana (thale cress)
<220> FEATURE:
<221> NAME/KEY: CDS
<222> LOCATION: (1)..(1206)
<220> FEATURE:
<221> NAME/KEY: misc_feature
<222> LOCATION: (1)..(1206)
<223> OTHER INFORMATION: unknown protein [Arabidopsis thaliana].
      ACCESSION   NP_200221
      VERSION     NP_200221.1  GI:15239547
      DBSOURCE    REFSEQ: accession NM_124790.2

<400> SEQUENCE: 11 atg aat cag ctc gcg ctt tca aga tcc ggt tac acc gcc gcc gtg agg    48
Met Asn Gln Leu Ala Leu Ser Arg Ser Gly Tyr Thr Ala Ala Val Arg
1               5                   10                  15 ttt ctc cct atg ctt tcc gca gct gtt ccg aag atc tta tca tct ctc    96
Phe Leu Pro Met Leu Ser Ala Ala Val Pro Lys Ile Leu Ser Ser Leu
            20                  25                  30 gcc gcc gca tcc acc gtc cgc aac ttc agc tct acc gga agt cct ctc   144
Ala Ala Ala Ser Thr Val Arg Asn Phe Ser Ser Thr Gly Ser Pro Leu
        35                  40                  45 acc agc tac caa atc aat aaa cct tcg ccg tca aaa tcc ttc act tcc   192
Thr Ser Tyr Gln Ile Asn Lys Pro Ser Pro Ser Lys Ser Phe Thr Ser
50                  55                  60 agg ctt ctc cac caa tcc tcc tcc gcc ggt act cct ccg caa caa ctt   240
Arg Leu Leu His Gln Ser Ser Ser Ala Gly Thr Pro Pro Gln Gln Leu
65                  70                  75                  80 ttc ggc gcc cgt agc ttc tca tct ccc agc agt gat ttc aac agc tac   288
Phe Gly Ala Arg Ser Phe Ser Ser Pro Ser Ser Asp Phe Asn Ser Tyr
                85                  90                  95
```

| | | |
|---|---|---|
| cac att aat ccg ccg tct aac tgg gga atc cga atc gtg ccg gag agg<br>His Ile Asn Pro Pro Ser Asn Trp Gly Ile Arg Ile Val Pro Glu Arg<br>100 105 110 | | 336 |
| aaa gct tgt gtg att gag cgg ttt ggt aaa ttc cac acg act ttg ccg<br>Lys Ala Cys Val Ile Glu Arg Phe Gly Lys Phe His Thr Thr Leu Pro<br>115 120 125 | | 384 |
| gcg ggg att cac ttc ctt gtt ccg ttt gtg gat cgt atc gct tat gtt<br>Ala Gly Ile His Phe Leu Val Pro Phe Val Asp Arg Ile Ala Tyr Val<br>130 135 140 | | 432 |
| cat tct cta aag gaa gaa gcg att cct att ggt aat cag act gcg att<br>His Ser Leu Lys Glu Glu Ala Ile Pro Ile Gly Asn Gln Thr Ala Ile<br>145 150 155 160 | | 480 |
| aca aag gat aac gtt agc atc cac atc gat ggt gtt ctc tac gtt aag<br>Thr Lys Asp Asn Val Ser Ile His Ile Asp Gly Val Leu Tyr Val Lys<br>165 170 175 | | 528 |
| att gtg gat cct aag ttg gct tct tat ggc gtt gag aat ccg atc tat<br>Ile Val Asp Pro Lys Leu Ala Ser Tyr Gly Val Glu Asn Pro Ile Tyr<br>180 185 190 | | 576 |
| gct gtt atg cag ttg gct cag act aca atg cgt agt gag ctc ggt aaa<br>Ala Val Met Gln Leu Ala Gln Thr Thr Met Arg Ser Glu Leu Gly Lys<br>195 200 205 | | 624 |
| att act ctt gac aag act ttt gag gaa cgg gac act ctc aat gag aag<br>Ile Thr Leu Asp Lys Thr Phe Glu Glu Arg Asp Thr Leu Asn Glu Lys<br>210 215 220 | | 672 |
| att gtg gaa gcc atc aat gtt gct gca aaa gat tgg ggt ctt cag tgc<br>Ile Val Glu Ala Ile Asn Val Ala Ala Lys Asp Trp Gly Leu Gln Cys<br>225 230 235 240 | | 720 |
| ctt cgt tat gag atc agg gat atc atg cct cct aat gga gtg aga gtt<br>Leu Arg Tyr Glu Ile Arg Asp Ile Met Pro Pro Asn Gly Val Arg Val<br>245 250 255 | | 768 |
| gct atg gaa atg caa gct gaa gct gaa cgt aaa aag aga gcc cag att<br>Ala Met Glu Met Gln Ala Glu Ala Glu Arg Lys Lys Arg Ala Gln Ile<br>260 265 270 | | 816 |
| ctt gag tct gaa gga gaa cgt caa gcc cat atc aat aga gct gat ggt<br>Leu Glu Ser Glu Gly Glu Arg Gln Ala His Ile Asn Arg Ala Asp Gly<br>275 280 285 | | 864 |
| aag aaa agt tct gta atc ttg gaa tca gaa gct gca atg atg gac caa<br>Lys Lys Ser Ser Val Ile Leu Glu Ser Glu Ala Ala Met Met Asp Gln<br>290 295 300 | | 912 |
| gtc aat cgt gca caa ggt gag gct gaa gca ata tta gct aga gca caa<br>Val Asn Arg Ala Gln Gly Glu Ala Glu Ala Ile Leu Ala Arg Ala Gln<br>305 310 315 320 | | 960 |
| gca aca gcc aag gga ctg gcc atg gta tct caa tcc ctc aag gaa gct<br>Ala Thr Ala Lys Gly Leu Ala Met Val Ser Gln Ser Leu Lys Glu Ala<br>325 330 335 | | 1008 |
| ggt gga gag gag gct gcg agt ttg aga gtt gcg gag caa tac att caa<br>Gly Gly Glu Glu Ala Ala Ser Leu Arg Val Ala Glu Gln Tyr Ile Gln<br>340 345 350 | | 1056 |
| gct ttt ggc aaa att gct aag gag ggt aca aca atg ctg ctt ccg agt<br>Ala Phe Gly Lys Ile Ala Lys Glu Gly Thr Thr Met Leu Leu Pro Ser<br>355 360 365 | | 1104 |
| aat gtc gac aat cct gct agc atg atc gct caa gct tta gga atg tac<br>Asn Val Asp Asn Pro Ala Ser Met Ile Ala Gln Ala Leu Gly Met Tyr<br>370 375 380 | | 1152 |
| aaa ggg ttg tca aca aag gtc cca aca gtg gtt tca ggg aaa ctt ctg<br>Lys Gly Leu Ser Thr Lys Val Pro Thr Val Val Ser Gly Lys Leu Leu<br>385 390 395 400 | | 1200 |
| gag tag<br>Glu | | 1206 |

```
<210> SEQ ID NO 12
<211> LENGTH: 401
<212> TYPE: PRT
<213> ORGANISM: Arabidopsis thaliana (thale cress)
<220> FEATURE:
<221> NAME/KEY: misc_feature
<222> LOCATION: (1)..(1206)
<223> OTHER INFORMATION: unknown protein [Arabidopsis thaliana].
          ACCESSION   NP_200221
          VERSION     NP_200221.1  GI:15239547
          DBSOURCE    REFSEQ: accession NM_124790.2

<400> SEQUENCE: 12

Met Asn Gln Leu Ala Leu Ser Arg Ser Gly Tyr Thr Ala Ala Val Arg
1               5                   10                  15

Phe Leu Pro Met Leu Ser Ala Ala Val Pro Lys Ile Leu Ser Ser Leu
            20                  25                  30

Ala Ala Ala Ser Thr Val Arg Asn Phe Ser Thr Gly Ser Pro Leu
        35                  40                  45

Thr Ser Tyr Gln Ile Asn Lys Pro Ser Pro Ser Lys Ser Phe Thr Ser
    50                  55                  60

Arg Leu Leu His Gln Ser Ser Ala Gly Thr Pro Pro Gln Gln Leu
65                  70                  75                  80

Phe Gly Ala Arg Ser Phe Ser Ser Pro Ser Asp Phe Asn Ser Tyr
                85                  90                  95

His Ile Asn Pro Pro Ser Asn Trp Gly Ile Arg Ile Val Pro Glu Arg
            100                 105                 110

Lys Ala Cys Val Ile Glu Arg Phe Gly Lys Phe His Thr Thr Leu Pro
        115                 120                 125

Ala Gly Ile His Phe Leu Val Pro Phe Val Asp Arg Ile Ala Tyr Val
    130                 135                 140

His Ser Leu Lys Glu Glu Ala Ile Pro Ile Gly Asn Gln Thr Ala Ile
145                 150                 155                 160

Thr Lys Asp Asn Val Ser Ile His Ile Asp Gly Val Leu Tyr Val Lys
                165                 170                 175

Ile Val Asp Pro Lys Leu Ala Ser Tyr Gly Val Glu Asn Pro Ile Tyr
            180                 185                 190

Ala Val Met Gln Leu Ala Gln Thr Thr Met Arg Ser Glu Leu Gly Lys
        195                 200                 205

Ile Thr Leu Asp Lys Thr Phe Glu Glu Arg Asp Thr Leu Asn Glu Lys
    210                 215                 220

Ile Val Glu Ala Ile Asn Val Ala Ala Lys Asp Trp Gly Leu Gln Cys
225                 230                 235                 240

Leu Arg Tyr Glu Ile Arg Asp Ile Met Pro Pro Asn Gly Val Arg Val
                245                 250                 255

Ala Met Glu Met Gln Ala Glu Ala Glu Arg Lys Lys Arg Ala Gln Ile
            260                 265                 270

Leu Glu Ser Glu Gly Glu Arg Gln Ala His Ile Asn Arg Ala Asp Gly
        275                 280                 285

Lys Lys Ser Ser Val Ile Leu Glu Ser Glu Ala Ala Met Met Asp Gln
    290                 295                 300

Val Asn Arg Ala Gln Gly Glu Ala Glu Ala Ile Leu Ala Arg Ala Gln
305                 310                 315                 320

Ala Thr Ala Lys Gly Leu Ala Met Val Ser Gln Ser Leu Lys Glu Ala
                325                 330                 335

Gly Gly Glu Glu Ala Ala Ser Leu Arg Val Ala Glu Gln Tyr Ile Gln
            340                 345                 350
```

```
Ala Phe Gly Lys Ile Ala Lys Glu Gly Thr Thr Met Leu Leu Pro Ser
            355                 360                 365

Asn Val Asp Asn Pro Ala Ser Met Ile Ala Gln Ala Leu Gly Met Tyr
        370                 375                 380

Lys Gly Leu Ser Thr Lys Val Pro Thr Val Val Ser Gly Lys Leu Leu
385                 390                 395                 400

Glu

<210> SEQ ID NO 13
<211> LENGTH: 1206
<212> TYPE: DNA
<213> ORGANISM: Arabidopsis thaliana (thale cress)
<220> FEATURE:
<221> NAME/KEY: CDS
<222> LOCATION: (1)..(1206)
<220> FEATURE:
<221> NAME/KEY: misc_feature
<222> LOCATION: (1)..(1206)
<223> OTHER INFORMATION: stomatin-like protein [Arabidopsis thaliana].
      ACCESSION   AAM63205
      VERSION     AAM63205.1  GI:21554125
      DBSOURCE    accession AY085995.1

<400> SEQUENCE: 13 atg aat cag ctc gcg ctt tca aga tcc ggt tac acc gcc gcc gtg agg        48
Met Asn Gln Leu Ala Leu Ser Arg Ser Gly Tyr Thr Ala Ala Val Arg
1               5                   10                  15 ttt ctc cct atg ctt tcc gca gct gtt ccg aag atc tta tca tct ctc        96
Phe Leu Pro Met Leu Ser Ala Ala Val Pro Lys Ile Leu Ser Ser Leu
            20                  25                  30 gcc gcc gca tcc acc gtc cgc aac ttc agc tct acc gga agt cct ctc       144
Ala Ala Ala Ser Thr Val Arg Asn Phe Ser Ser Thr Gly Ser Pro Leu
        35                  40                  45 acc agc tac caa atc aat aaa cct tcg ccg tca aaa tcc ttc act tcc       192
Thr Ser Tyr Gln Ile Asn Lys Pro Ser Pro Ser Lys Ser Phe Thr Ser
    50                  55                  60 agg ctt ctc cac caa tcc tcc tcc gcc ggt act cct ccg caa caa ctt       240
Arg Leu Leu His Gln Ser Ser Ser Ala Gly Thr Pro Pro Gln Gln Leu
65                  70                  75                  80 ttc ggc gcc cgt agc ttc tca tct ccc agc agt gat ttc aac agc tac       288
Phe Gly Ala Arg Ser Phe Ser Ser Pro Ser Ser Asp Phe Asn Ser Tyr
                85                  90                  95 cac att aat ccg ccg tct aac tgg gga atc cga atc gtg ccg gag agg       336
His Ile Asn Pro Pro Ser Asn Trp Gly Ile Arg Ile Val Pro Glu Arg
            100                 105                 110 aaa gct tgt gtg att gag cgg ttt ggt aaa ttc cac acg act ttg ccg       384
Lys Ala Cys Val Ile Glu Arg Phe Gly Lys Phe His Thr Thr Leu Pro
        115                 120                 125 gcg ggg att cac ttc ctt gtt ccg ttt gtg gat cgt atc gct tat gtt       432
Ala Gly Ile His Phe Leu Val Pro Phe Val Asp Arg Ile Ala Tyr Val
    130                 135                 140 cat tct cta aag gaa gaa gcg att cct att ggt aat cag act gcg att       480
His Ser Leu Lys Glu Glu Ala Ile Pro Ile Gly Asn Gln Thr Ala Ile
145                 150                 155                 160 aca aag gat aac gtt agc atc cac atc gat ggt ttt ctc tac gtt aag       528
Thr Lys Asp Asn Val Ser Ile His Ile Asp Gly Phe Leu Tyr Val Lys
                165                 170                 175 att gtg gat cct aag ttg gct tct tat ggc gtt gag aat ccg atc tat       576
Ile Val Asp Pro Lys Leu Ala Ser Tyr Gly Val Glu Asn Pro Ile Tyr
            180                 185                 190 gct gtt atg cag ttg gct cag act aca atg cgt agt gag ctc ggt aaa       624
Ala Val Met Gln Leu Ala Gln Thr Thr Met Arg Ser Glu Leu Gly Lys
```

```
att act ctt gac aag act ttt gag gaa cgg gac act ctc aat gag aag      672
Ile Thr Leu Asp Lys Thr Phe Glu Glu Arg Asp Thr Leu Asn Glu Lys
210                 215                 220 att gtg gaa gcc atc aat gtt gct gca aaa gat tgg ggt ctt cag tgc      720
Ile Val Glu Ala Ile Asn Val Ala Ala Lys Asp Trp Gly Leu Gln Cys
225                 230                 235                 240 ctt agt tat gag atc agg gat atc atg cct cct aat gga gtg aga gtt      768
Leu Ser Tyr Glu Ile Arg Asp Ile Met Pro Pro Asn Gly Val Arg Val
                245                 250                 255 gct atg gaa atg caa gct gaa gct gaa cgt aaa aag aga gcc cag att      816
Ala Met Glu Met Gln Ala Glu Ala Glu Arg Lys Lys Arg Ala Gln Ile
        260                 265                 270 ctt gag tct gaa gga gaa cgt caa gcc cat atc aat aga gct gat ggt      864
Leu Glu Ser Glu Gly Glu Arg Gln Ala His Ile Asn Arg Ala Asp Gly
    275                 280                 285 aag aaa agt tct gta atc ttg gaa tca gaa gct gca atg atg gac caa      912
Lys Lys Ser Ser Val Ile Leu Glu Ser Glu Ala Ala Met Met Asp Gln
290                 295                 300 gtc aat cgt gca caa ggt gag gct gaa gca ata tta gct aga gca caa      960
Val Asn Arg Ala Gln Gly Glu Ala Glu Ala Ile Leu Ala Arg Ala Gln
305                 310                 315                 320 gca aca gcc aag gga ctg gcc atg gta tct caa tcc ctc aag gaa gct     1008
Ala Thr Ala Lys Gly Leu Ala Met Val Ser Gln Ser Leu Lys Glu Ala
                325                 330                 335 ggt gga gag gag gct gcg agt ttg aga gtt gcg gag caa tac att caa     1056
Gly Gly Glu Glu Ala Ala Ser Leu Arg Val Ala Glu Gln Tyr Ile Gln
        340                 345                 350 gct ttt ggc aaa att gct aag gag ggt aca aca atg ctg ctt ccg agt     1104
Ala Phe Gly Lys Ile Ala Lys Glu Gly Thr Thr Met Leu Leu Pro Ser
    355                 360                 365 aat gtc gac aat cct gct agc atg atc gct caa gct tta gga atg tac     1152
Asn Val Asp Asn Pro Ala Ser Met Ile Ala Gln Ala Leu Gly Met Tyr
370                 375                 380 aaa ggc ttg tca aca aag gtc cca aca gtg gtt tca ggg aaa ctt ctg     1200
Lys Gly Leu Ser Thr Lys Val Pro Thr Val Val Ser Gly Lys Leu Leu
385                 390                 395                 400 gag tag                                                             1206
Glu
```

<210> SEQ ID NO 14
<211> LENGTH: 401
<212> TYPE: PRT
<213> ORGANISM: Arabidopsis thaliana (thale cress)
<220> FEATURE:
<221> NAME/KEY: misc_feature
<222> LOCATION: (1)..(1206)
<223> OTHER INFORMATION: stomatin-like protein [Arabidopsis thaliana].
    ACCESSION   AAM63205
    VERSION     AAM63205.1  GI:21554125
    DBSOURCE    accession AY085995.1

<400> SEQUENCE: 14

```
Met Asn Gln Leu Ala Leu Ser Arg Ser Gly Tyr Thr Ala Ala Val Arg
1               5                   10                  15

Phe Leu Pro Met Leu Ser Ala Ala Val Pro Lys Ile Leu Ser Ser Leu
            20                  25                  30

Ala Ala Ala Ser Thr Val Arg Asn Phe Ser Ser Thr Gly Ser Pro Leu
        35                  40                  45

Thr Ser Tyr Gln Ile Asn Lys Pro Ser Pro Ser Lys Phe Thr Ser
    50                  55                  60
```

```
Arg Leu Leu His Gln Ser Ser Ala Gly Thr Pro Pro Gln Gln Leu
 65                  70                  75                  80

Phe Gly Ala Arg Ser Phe Ser Pro Ser Asp Phe Asn Ser Tyr
             85                  90                  95

His Ile Asn Pro Pro Ser Asn Trp Gly Ile Arg Ile Val Pro Glu Arg
             100                 105                 110

Lys Ala Cys Val Ile Glu Arg Phe Gly Lys Phe His Thr Thr Leu Pro
             115                 120                 125

Ala Gly Ile His Phe Leu Val Pro Phe Val Asp Arg Ile Ala Tyr Val
             130                 135                 140

His Ser Leu Lys Glu Glu Ala Ile Pro Ile Gly Asn Gln Thr Ala Ile
145                 150                 155                 160

Thr Lys Asp Asn Val Ser Ile His Ile Asp Gly Phe Leu Tyr Val Lys
                165                 170                 175

Ile Val Asp Pro Lys Leu Ala Ser Tyr Gly Val Glu Asn Pro Ile Tyr
                180                 185                 190

Ala Val Met Gln Leu Ala Gln Thr Thr Met Arg Ser Glu Leu Gly Lys
            195                 200                 205

Ile Thr Leu Asp Lys Thr Phe Glu Arg Asp Thr Leu Asn Glu Lys
210                 215                 220

Ile Val Glu Ala Ile Asn Val Ala Ala Lys Asp Trp Gly Leu Gln Cys
225                 230                 235                 240

Leu Ser Tyr Glu Ile Arg Asp Ile Met Pro Pro Asn Gly Val Arg Val
                245                 250                 255

Ala Met Glu Met Gln Ala Glu Ala Glu Arg Lys Lys Arg Ala Gln Ile
            260                 265                 270

Leu Glu Ser Glu Gly Glu Arg Gln Ala His Ile Asn Arg Ala Asp Gly
        275                 280                 285

Lys Lys Ser Ser Val Ile Leu Glu Ser Glu Ala Ala Met Met Asp Gln
290                 295                 300

Val Asn Arg Ala Gln Gly Glu Ala Glu Ala Ile Leu Ala Arg Ala Gln
305                 310                 315                 320

Ala Thr Ala Lys Gly Leu Ala Met Val Ser Gln Ser Leu Lys Glu Ala
                325                 330                 335

Gly Gly Glu Glu Ala Ala Ser Leu Arg Val Ala Glu Gln Tyr Ile Gln
            340                 345                 350

Ala Phe Gly Lys Ile Ala Lys Glu Gly Thr Thr Met Leu Leu Pro Ser
            355                 360                 365

Asn Val Asp Asn Pro Ala Ser Met Ile Ala Gln Ala Leu Gly Met Tyr
370                 375                 380

Lys Gly Leu Ser Thr Lys Val Pro Thr Val Val Ser Gly Lys Leu Leu
385                 390                 395                 400

Glu

<210> SEQ ID NO 15
<211> LENGTH: 282
<212> TYPE: PRT
<213> ORGANISM: Artificial Sequence
<220> FEATURE:
<223> OTHER INFORMATION: Consensus sequence from sequence alignment of
      the STM1 sequences shown
<220> FEATURE:
<221> NAME/KEY: MISC_FEATURE
<222> LOCATION: (1)..(143)
<223> OTHER INFORMATION: Consensus Sequence 1 (100%): Xaa at location 1,
      3, 5, 7, 8, 13, 16, 18, 24-26, 29-30, 32, 34, 36, 38, 52, 56-59,
      67, 69, 71-74, 79, 82-83, 89-90, 93, 96, 121, 124-125, 128-129,
      132, 135-136, 140, 142-143 can be any amino acid; Xaa can be no,
```

-continued one or two amino acid(s), preferably, Xaa is one amino acid.
<220> FEATURE:
<221> NAME/KEY: MISC_FEATURE
<222> LOCATION: (150)..(282)
<223> OTHER INFORMATION: Consensus Sequence 1 (100%): Xaa at location
      150, 153, 155-157, 164, 178-200, 202-206, 210, 212, 219-221, 225,
      227-230, 232-237, 239-241, 244, 246-247, 252-253, 256-258,
      260-265, 269-273, 275-278, 281-282 can be any amino acid; Xaa can
      be no, one or two amino acid(s), preferably, Xaa is one amino
      acid.

<400> SEQUENCE: 15

Xaa Pro Xaa Asn Xaa Gly Xaa Xaa Ile Val Pro Glu Xaa Lys Ala Xaa
 1               5                  10                  15

Val Xaa Glu Arg Phe Gly Lys Xaa Xaa Xaa Thr Leu Xaa Xaa Gly Xaa
             20                  25                  30

His Xaa Leu Xaa Pro Xaa Val Asp Arg Ile Ala Tyr Val His Ser Leu
         35                  40                  45

Lys Glu Glu Xaa Ile Pro Ile Xaa Xaa Xaa Xaa Ala Ile Thr Lys Asp
 50                  55                  60

Asn Val Xaa Ile Xaa Ile Xaa Xaa Xaa Tyr Val Lys Ile Xaa Asp
 65                  70                  75                  80

Pro Xaa Xaa Ala Ser Tyr Gly Val Xaa Xaa Pro Ile Xaa Ala Val Xaa
             85                  90                  95

Gln Leu Ala Gln Thr Thr Met Arg Ser Glu Leu Gly Lys Ile Thr Leu
            100                 105                 110

Asp Lys Thr Phe Glu Glu Arg Asp Xaa Leu Asn Xaa Xaa Ile Val Xaa
            115                 120                 125

Xaa Ile Asn Xaa Ala Ala Xaa Xaa Trp Gly Leu Xaa Cys Xaa Xaa Tyr
            130                 135                 140

Glu Ile Arg Asp Ile Xaa Pro Pro Xaa Gly Xaa Xaa Xaa Ala Met Glu
145                 150                 155                 160

Met Gln Ala Xaa Ala Glu Arg Lys Lys Arg Ala Gln Ile Leu Glu Ser
            165                 170                 175

Glu Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Ala Xaa Xaa Xaa Xaa Xaa Xaa Asn Arg
            195                 200                 205

Ala Xaa Gly Xaa Ala Glu Ala Ile Leu Ala Xaa Xaa Xaa Ala Thr Ala
            210                 215                 220

Xaa Gly Xaa Xaa Xaa Xaa Ser Xaa Xaa Xaa Xaa Xaa Gly Xaa Xaa
225                 230                 235                 240

Xaa Ala Ala Xaa Leu Xaa Xaa Ala Glu Gln Tyr Xaa Xaa Ala Phe Xaa
            245                 250                 255

Xaa Xaa Ala Xaa Xaa Xaa Xaa Xaa Leu Leu Pro Xaa Xaa Xaa Xaa
            260                 265                 270

Xaa Pro Xaa Xaa Xaa Xaa Ala Gln Xaa Xaa
            275                 280

<210> SEQ ID NO 16
<211> LENGTH: 282
<212> TYPE: PRT
<213> ORGANISM: Artificial Sequence
<220> FEATURE:
<223> OTHER INFORMATION: Consensus sequence from sequence alignment of
      the STM1 sequences shown
<220> FEATURE:
<221> NAME/KEY: MISC_FEATURE
<222> LOCATION: (1)..(272)
<223> OTHER INFORMATION: Consensus Sequence 1: Xaa at location 3, 25,
      36, 96, 153, 157, 182, 186, 197, 228, 237, 240, 253, 270, 272 can be any amino acid; Xaa can be no, one or two amino acid(s), preferably, Xaa is one amino acid.

<400> SEQUENCE: 16

```
Pro Pro Xaa Asn Trp Gly Ile Arg Ile Val Pro Glu Arg Lys Ala Phe
1               5                   10                  15

Val Ile Glu Arg Phe Gly Lys Tyr Xaa Thr Thr Leu Pro Ser Gly Ile
            20                  25                  30

His Phe Leu Xaa Pro Phe Val Asp Arg Ile Ala Tyr Val His Ser Leu
        35                  40                  45

Lys Glu Glu Ala Ile Pro Ile Pro Asn Gln Thr Ala Ile Thr Lys Asp
50                  55                  60

Asn Val Ser Ile His Ile Asp Gly Val Leu Tyr Val Lys Ile Val Asp
65                  70                  75                  80

Pro Lys Leu Ala Ser Tyr Gly Val Glu Asn Pro Ile Tyr Ala Val Xaa
                85                  90                  95

Gln Leu Ala Gln Thr Thr Met Arg Ser Glu Leu Gly Lys Ile Thr Leu
            100                 105                 110

Asp Lys Thr Phe Glu Glu Arg Asp Thr Leu Asn Glu Lys Ile Val Glu
        115                 120                 125

Ala Ile Asn Val Ala Ala Lys Asp Trp Gly Leu Gln Cys Leu Arg Tyr
    130                 135                 140

Glu Ile Arg Asp Ile Met Pro Pro Xaa Gly Val Arg Xaa Ala Met Glu
145                 150                 155                 160

Met Gln Ala Glu Ala Glu Arg Lys Lys Arg Ala Gln Ile Leu Glu Ser
                165                 170                 175

Glu Gly Glu Arg Gln Xaa His Ile Asn Xaa Ala Asp Gly Lys Lys Ser
            180                 185                 190

Ser Val Ile Leu Xaa Ser Glu Ala Ala Met Met Asp Gln Val Asn Arg
        195                 200                 205

Ala Gln Gly Glu Ala Glu Ala Ile Leu Ala Arg Ala Gln Ala Thr Ala
    210                 215                 220

Lys Gly Leu Xaa Leu Val Ser Gln Ser Leu Lys Glu Xaa Gly Gly Xaa
225                 230                 235                 240

Glu Ala Ala Ser Leu Arg Val Ala Glu Gln Tyr Ile Xaa Ala Phe Gly
                245                 250                 255

Asn Ile Ala Lys Glu Gly Thr Thr Met Leu Leu Pro Ser Xaa Ala Xaa
            260                 265                 270

Asn Pro Ala Ser Met Ile Ala Gln Ala Leu
        275                 280
```

<210> SEQ ID NO 17
<211> LENGTH: 282
<212> TYPE: PRT
<213> ORGANISM: Artificial Sequence
<220> FEATURE:
<223> OTHER INFORMATION: Consensus sequence from sequence alignment of the STM1 sequences shown
<220> FEATURE:
<221> NAME/KEY: MISC_FEATURE
<222> LOCATION: (1)..(272)
<223> OTHER INFORMATION: Consensus Sequence 3: Xaa at position 25, 153, 157, 186, 197, 228, 237, 240, 253, 270, 272 can be any amino acid; Xaa can be no, one or two amino acid(s), preferably, Xaa is one amino acid.
<220> FEATURE:
<221> NAME/KEY: MISC_FEATURE
<222> LOCATION: (1)..(282)
<223> OTHER INFORMATION: Position 3 might also show V, T or A. Position 36 might also show V or M. Position 96 might also show L, V or M. Position 182 might also show S

<400> SEQUENCE: 17

```
Pro Pro Ser Asn Trp Gly Ile Arg Ile Val Pro Glu Arg Lys Ala Phe
1               5                   10                  15
Val Ile Glu Arg Phe Gly Lys Tyr Xaa Thr Thr Leu Pro Ser Gly Ile
            20                  25                  30
His Phe Leu Ile Pro Phe Val Asp Arg Ile Ala Tyr Val His Ser Leu
        35                  40                  45
Lys Glu Glu Ala Ile Pro Ile Pro Asn Gln Thr Ala Ile Thr Lys Asp
    50                  55                  60
Asn Val Ser Ile His Ile Asp Gly Val Leu Tyr Val Lys Ile Val Asp
65                  70                  75                  80
Pro Lys Leu Ala Ser Tyr Gly Val Glu Asn Pro Ile Tyr Ala Val Ile
                85                  90                  95
Gln Leu Ala Gln Thr Thr Met Arg Ser Glu Leu Gly Lys Ile Thr Leu
            100                 105                 110
Asp Lys Thr Phe Glu Glu Arg Asp Thr Leu Asn Glu Lys Ile Val Glu
        115                 120                 125
Ala Ile Asn Val Ala Ala Lys Asp Trp Gly Leu Gln Cys Leu Arg Tyr
    130                 135                 140
Glu Ile Arg Asp Ile Met Pro Pro Xaa Gly Val Arg Xaa Ala Met Glu
145                 150                 155                 160
Met Gln Ala Glu Ala Glu Arg Lys Lys Arg Ala Gln Ile Leu Glu Ser
                165                 170                 175
Glu Gly Glu Arg Gln Ala His Ile Asn Xaa Ala Asp Gly Lys Lys Ser
            180                 185                 190
Ser Val Ile Leu Xaa Ser Glu Ala Ala Met Met Asp Gln Val Asn Arg
        195                 200                 205
Ala Gln Gly Glu Ala Glu Ala Ile Leu Ala Arg Ala Gln Ala Thr Ala
    210                 215                 220
Lys Gly Leu Xaa Leu Val Ser Gln Ser Leu Lys Glu Xaa Gly Gly Xaa
225                 230                 235                 240
Glu Ala Ala Ser Leu Arg Val Ala Glu Gln Tyr Ile Xaa Ala Phe Gly
                245                 250                 255
Asn Ile Ala Lys Glu Gly Thr Thr Met Leu Leu Pro Ser Xaa Ala Xaa
            260                 265                 270
Asn Pro Ala Ser Met Ile Ala Gln Ala Leu
        275                 280
```

<210> SEQ ID NO 18
<211> LENGTH: 24
<212> TYPE: DNA
<213> ORGANISM: Artificial sequence
<220> FEATURE:
<223> OTHER INFORMATION: PCR Primer

<400> SEQUENCE: 18
gatatggcga tgtcgacggc gacc       24

<210> SEQ ID NO 19
<211> LENGTH: 23
<212> TYPE: DNA
<213> ORGANISM: Artificial sequence
<220> FEATURE:
<223> OTHER INFORMATION: PCR Primer

<400> SEQUENCE: 19
aacttacttc tggtgcggaa agg       23

```
<210> SEQ ID NO 20
<211> LENGTH: 10
<212> TYPE: DNA
<213> ORGANISM: Artificial sequence
<220> FEATURE:
<223> OTHER INFORMATION: Promoter element

<400> SEQUENCE: 20
tcatcttctt                                                        10
```

USE OF STOMATIN (STM1) POLYNUCLEOTIDES FOR ACHIEVING A PATHOGEN RESISTANCE IN PLANTS

RELATED APPLICATIONS

This application is a national stage application (under 35 U.S.C. §371) of PCT/EP2007/050062, filed Jan. 4, 2007, which claims benefit of European application 06100304.2, filed Jan. 12, 2006.

SEQUENCE LISTING SUBMISSION

The Sequence Listing associated with this application is filed in electronic format via EFS-Web and hereby incorporated by reference into the specification in its entirety. The name of the text file containing the Sequence Listing is Sequenece_Listing_13987_00094. The size of the text file is 82 KB, and the text file was created on Jun. 15, 2011.

FIELD OF THE INVENTION

The invention relates to a method of generating or increasing a pathogen resistance in plants by reducing the expression of at least one stomatin polypeptide or a functional equivalent thereof. The invention relates to novel nucleic acid sequences coding for a *Hordeum vulgare* stomatin (HvSTM1) polynucleotide and describes homologous sequences (STM1) thereof, and to their use in methods for obtaining a pathogen resistance in plants, and to nucleic acid constructs, expression cassettes and vectors which comprise these sequences and which are suitable for mediating a fungal resistance in plants. The invention furthermore relates to transgenic organisms, in particular plants, which are transformed with these expression cassettes or vectors, and to cultures, parts or transgenic propagation material derived therefrom.

DESCRIPTION OF RELATED ART

There are only few approaches which confer a resistance to pathogens, mainly fungal pathogens, to plants. This shortcoming can partly be attributed to the complexity of the biological systems in question. Another fact which stands in the way of obtaining resistances to pathogens is that little is known about the interactions between pathogen and plant. The large number of different pathogens, the infection mechanisms developed by these organisms and the defence mechanisms developed by the plant phyla, families and species interact with one another in many different ways.

Fungal pathogens have developed essentially two infection strategies. Some fungi enter into the host tissue via the stomata (for example rusts, *Septoria* species, *Fusarium* species) and penetrate the mesophyll tissue, while others penetrate via the cuticles into the epidermal cells underneath (for example *Blumeria* species).

The infections caused by the fungal pathogens lead to the activation of the plant's defence mechanisms in the infected plants. Thus, it has been possible to demonstrate that defence reactions against epidermis-penetrating fungi frequently start with the formation of a penetration resistance (formation of papillae, strengthening of the cell wall with callose as the main constituent) underneath the fungal penetration hypha (Elliott et al. Mol Plant Microbe Interact. 15: 1069-77; 2002).

In some cases, however, the plant's defence mechanisms only confer an insufficient protection mechanism against the attack by pathogens.

The formation of a penetration resistance to pathogens whose infection mechanism comprises a penetration of the epidermal cells or of the mesophyll cells is of great importance both for monocotyledonous and for dicotyledonous plants. In contrast to described mlo-mediated resistance, it can probably make possible the development of a broad-spectrum resistance against obligatory biotrophic, hemibiotrophic and necrotrophic fungi.

The present invention was therefore based on the object of providing a method for generating a resistance of plants to penetrating pathogens.

The object is achieved by the embodiments characterized in the claims.

BRIEF DESCRIPTION OF THE DRAWINGS

FIG. 1 shows increase in the mildew resistance of barley by RNAi from stomatin STM1 proteins. Barley leaf segments were bombarded with an RNAi construct against STM1, the leaf segments were inoculated with barley mildew of the isolate Bgh-A6 and the frequency of fungal haustoria in transformed epidermal cells was determined in relation to the vector control ("relative HAU formation"). An RNAi against STM1 reduced the number of penetrated epidermal cells by more than 50%. SNAP34 acts as the control.

FIG. 2 shows sequence alignment from stomatin STM1 protein sequences with polypeptides from barley, rice, maize and Arabidopsis thaliana. BlastX_1_STM_Os: SEQ ID NO: 4; BlastX_2_STM_Zm: SEQ ID NO: 6; BlastX_3_STM_Ath SEQ ID NO: 8; BlastX_4_STM_Ath: SEQ ID NO: 10; BlastX_5_STM_Ath: SEQ ID NO: 12; BlastX_6_STM_Ath: SEQ ID NO: 14; Translation of HvSTM1: SEQ ID NO: 2; Consensus: SEQ ID NO: 17.

DETAILED DESCRIPTION OF THE INVENTION

The invention therefore relates to a method of increasing the resistance to penetrating pathogens in a monocotyledonous or dicotyledonous plant, or a part of a plant, for example in an organ, tissue, a cell or a part of a plant cell, for example in an organelle, which comprises lessening or reducing the activity or amount of a stomatin protein (STM1) in the plant, or a part of the plant, for example in an organ, tissue, a cell or a part of a cell, for example in a cell compartment, for example in an organelle, in comparison with a control plant or a part of a control plant, for example its organ, tissue, cell or part of a cell, for example in a cell compartment, for example in an organelle.

Preferably, a race-unspecific resistance is obtained in the method according to the invention. Thus, for example, a broad-spectrum resistance against obligatorily biotrophic and/or hembiotrophic and/or necrotrophic fungi of plants, in particular against mesophyll-penetrating pathogens, can be obtained by the method according to the invention.

Surprisingly, it has been observed that the gene silencing via dsRNAi of a gene which codes for the stomatin protein HvSTM1 results in an increase in the resistance of monocotyledonous and dicotyledonous plants to fungal pathogens. Thus, this negative control function in the event of attack by fungal pathogens has been demonstrated for the stomatin protein HvSTM1 from barley (*Hordeum vulgare*) (HvSTM1), wheat (*Triticum aestivum*) and thale cress (*Arabidopsis thaliana*).

It has been found within the scope of a TIGS (=Transient Induced Gene Silencing) analysis in barley by the method of Schweizer et al. (2001) that a dsRNAi-mediated silencing of the gene HvSTM greatly increases the resistance to *Blumeria*

*graminis* f. sp. *hordei* (synonym: *Erysiphe graminis* DC. f. sp. *hordei*). This effect has also been obtained in dicotyledonous species such as, for example, *Arabidopsis thaliana* by inducing the post-transcriptional gene silencing (PTGS). This emphasizes the universal importance of the loss-of-function of HvSTM1-homologous genes for the development of a broad-spectrum pathogen resistance of the plant.

Stomatin is an integral membrane protein which has first been identified in blood cells. In certain hereditary diseases, in which this protein is absent, a hemolytic anemia results. In this stomatocytosis, the blood cells suffer a pronounced passive diffusion of singly charged cations, which results in hyperhydration as the result of a high sodium concentration and a low potassium concentration. The name stomatin is derived from the mouth-like structure of these erythrocytes (Greek Stoma=mouth). Stomatin acts as a negative membrane permeability regulator for singly charged cations. Stomatin has a single membrane domain, while the remainder of the protein protrudes into the cytoplasm. The molecular mechanisms via which stomatin exerts its function is unclear. It is assumed that the cytoplasmic domain of the protein acts sterically as a sort of plug which closes ion channels and perhaps interacts with the cytoskeleton (Stewart G W, Argent A C, Dash B C J (1993) Biochim. Biophys. Acta 1225, 15-25; Stewart G W et al. (1992) Blood 79, 1593-1601).

A first potential plant stomatin was cloned in maize (Nadimpalli R et al. (2000) J. Biol. Chem. 275, 29579-29586). However, no functional data for this gene, Zm-stm1, were published. A potential role in pathogen defence has been assumed for other genes which were cloned in this work since transcripts of these genes were upregulated in the lesion Mimic-Mutante Les9. While such a context has not been demonstrated for Zm-stm1, the authors speculate about a role as a positive pathogen defence regulator, for example as promoters of the hypersensitive reaction (HR). In the same line as this argumentation, two other study groups have found that genes for proteins in *Arabidopsis* in the background of two mutants with an increased resistance are upregulated and that stomatin could therefore act as PR protein (Petersen M et al. (2000) Cell 103, 1111-1120; Brodersen P et al. (2002) Genes & Dev 16, 490-502).

The finding that a reduction in the expression of stomatin leads to a significant increase in the pathogen resistance in plants was all the more surprising.

In a further embodiment, the invention therefore relates to a method of generating a plant with an increased resistance to plant pathogens, preferably with a broad-spectrum resistance, in particular to fungal pathogens, for example from the classes Ascomycetes, Basidiomycetes, Chytridiomycetes or Oomycetes, for example of mildews of the family Erysiphaceae, genus *Blumeria*, by interfering with the cell wall structure, in particular by reducing the membrane permeability, for example for singly charged cations, in particular by modifying the ion concentration in the cell, preferably by increasing the concentration of singly charged cations, such as, for example, sodium, for example by mutation of an ion channel or of a protein which interacts with, or regulates, an ion channel.

In an embodiment, the invention therefore relates to a method of generating a plant with an increased resistance to plant pathogens, preferably with a broad-spectrum resistance, in particular to fungal pathogens, for example from the classes Ascomycetes, Basidiomycetes, Chytridiomycetes or Oomycetes, for example of mildews of the family Erysiphaceae, genus *Blumeria*, by reducing the expression or by mutation of a stomatin STM1 protein In a further embodiment, the activity of a subtilisin-like polypeptide is reduced, for example blocked or eliminated, in the method according to the invention.

In a further embodiment, in the method according to the invention the activity of a polypeptide is reduced or eliminated, which is encoded by a polynucleotide comprising at least one nucleic acid molecule selected from the group consisting of:

(a) nucleic acid molecule which codes for at least one polypeptide comprising the sequence as shown in SEQ ID No: 2, 4, 6, 8, 10, 12, 14 15, 16 or 17;

(b) nucleic acid molecule which comprises at least one polynucleotide of the sequence as shown in SEQ ID No: or 1, 3, 5, 7, 9, 11 or 13;

(c) nucleic acid molecule which codes for a polypeptide whose sequence has at least 50% identity to the sequences SEQ ID No: 2;

(d) nucleic acid molecule according to (a) to (c) which codes for a fragment or an epitope of the sequences as shown in SEQ. ID No.: 2, 4, 6, 8, 10, 12, 14, 15, 16 or 17;

(e) nucleic acid molecule which codes for a polypeptide which is recognized by a monoclonal antibody directed against a polypeptide which is encoded by the nucleic acid molecules as shown in (a) to (c);

(f) nucleic acid molecule which hybridizes under stringent conditions with a nucleic acid molecule as shown in (a) to (c); and (g) nucleic acid molecule which can be isolated from a DNA library using a nucleic acid molecule as shown in (a) to (c) or their part-fragments of at least 15 nt, preferably 20 nt, 30 nt, 50 nt, 100 nt, 200 nt or 500 nt, as probe under stringent hybridization conditions;

or comprises a complementary sequence thereof is reduced, for example eliminated.

In the method according to the invention, it is in particular the resistance to mesophyll-cell-penetrating pathogens which is preferably increased.

In one embodiment, the resistance is obtained by lessening, reducing or blocking the expression of a polypeptide, preferably of a polypeptide which is encoded by the above-described nucleic acid molecule, for example that of a stomatin STM1 from barley as shown herein in SEQ ID No. 2 and 3, or from Rice:

LOCUS XP_480193 377 aa linear PLN 9-NOV-2004
DEFINITION putative Band 7 protein [*Oryza sativa* (japonica cultivar-group)].
ACCESSION XP_480193
VERSION XP_480193.1 GI:50941331
DBSOURCE REFSEQ: accession XM_480193.1, Maize:

LOCUS AAF68388 394 aa linear PLN 11-SEP-2002
DEFINITION stomatin-like protein [*Zea mays*].
ACCESSION AAF68388
VERSION AAF68388.1 GI:7716464
DBSOURCE accession AF236372.1 or:

LOCUS CAB81408 515 aa linear PLN 16-APR-2005
DEFINITION putative protein [*Arabidopsis thaliana*].
ACCESSION CAB81408
VERSION CAB81408.1 GI:7269612
DBSOURCE embl locus ATCHRIV67, accession AL161571.2
LOCUS NP_567778 411 aa linear PLN 04-NOV-2005
DEFINITION unknown protein [*Arabidopsis thaliana*].
ACCESSION NP_567778
VERSION NP_567778.1 GI:18417021

DBSOURCE REFSEQ: accession NM_118894.2
LOCUS NP_200221 401 aa linear PLN 04-NOV-2005
DEFINITION unknown protein [*Arabidopsis thaliana*].
ACCESSION NP_200221
VERSION NP_200221.1 GI:15239547
DBSOURCE REFSEQ: accession NM_124790.2
LOCUS AAM63205 401 aa linear PLN 14-APR-2003
DEFINITION stomatin-like protein [*Arabidopsis thaliana*].
ACCESSION AAM63205
VERSION AAM63205.1 GI:21554125
DBSOURCE accession AY085995.1

On the other hand, it is also possible to reduce, lessen or block the endogenous activity of one of these polypeptides by methods known to the skilled worker, for example by mutating a genomically coding region for the active center, for binding sites, for localization signals, for domains, clusters and the like, such as, for example, of coding regions for coiled coil, HEAT, FBOX, LRR, IBIB, C2, WD40, beach, U-box or UND domains. The activity can be reduced in accordance with the invention by mutations which affect the secondary, tertiary or quaternary structure of the protein.

Mutations can be inserted for example by an EMS mutagenesis. Domains can be identified by suitable computer programs such as, for example, SMART or InterPRO, for example as described in Andersen P., The Journal of Biol. Chemistry, 279, 38, pp. 40053-40061, 2004 or Y. Mudgil, Plant Physiology, 134, 59-66, 2004, and literature cited therein. The suitable mutants can then be identified for example by tilling.

In one embodiment, the lessening of the polypeptide quantity, activity or function of a stomatin STM1 protein in a plant is combined with increasing the polypeptide quantity, activity or function of other resistance factors, preferably of a Bax inhibitor 1 protein (BI-1), preferably of the Bax inhibitor 1 protein from *Hordeum vulgare* (GenBank Acc.-No.: AJ290421), from *Nicotiana tabacum* (GenBank Acc.-No.: AF390556), rice (GenBank Acc.-No.: AB025926), *Arabidopsis* (GenBank Acc.-No.: AB025927) or tobacco and oilseed rape (GenBank Acc.-No.: AF390555, Bolduc N et al. (2003) Planta 216:377-386) or of ROR2 (for example from barley (GenBank Acc.-No.: AY246906), SnAP34 (for example from barley (GenBank Acc.-No.: AY247208) and/or of the lumenal binding protein BiP for example from rice (GenBank Acc.-No. AF006825). An increase can be achieved for example by mutagenesis or overexpression of a transgene, inter alia.

In one embodiment, the lowering of the polypeptide quantity, activity or function of a stomatin STM1 protein in a plant is combined with decreasing the protein quantity, activity or function of other resistance factors, preferably of the proteins RacB (for example from barley (GenBank Acc.-No.: AJ344223), CSL1 (for example from *Arabidopsis* (GenBank Acc.-No.: NM116593), HvNaOX (for example from barley (GenBank Acc.-No.: AJ251717), MLO (for example from barley (GenBank Acc.-No. Z83834), ARM1 (armadillo repeat protein; application number 05110468.5).

The activity or function of MLO, BI-1 and/or NaOX can be reduced or inhibited analogously to what has been described for MLO in WO 98/04586; WO 00/01722; WO 99/47552 and the further publications mentioned hereinbelow, whose content is herewith expressly incorporated by reference, in particular in order to describe the activity and inhibition of MLO. The description of the abovementioned publications describes processes, methods and especially preferred embodiments for lessening or inhibiting the activity or function of MLO; the examples indicate specifically how this can be realized.

The reduction of the activity or function, if appropriate of the expression of BI-1 is described in detail in WO 2003020939, which is herewith expressly incorporated into the present description. The description of the abovementioned publication describes processes and methods for lessening or inhibiting the activity or function of BI-1; the examples indicate specifically how this can be realized. The reduction or inhibition of the activity or function of BI-1 is especially preferably carried out in accordance with the embodiments especially preferred in WO 2003020939 and the examples and in the organisms shown therein as being especially preferred, in particular in a plant, for example constitutively, or a part thereof, for example in a tissue, but especially advantageously at least in the epidermis or in a considerable part of the epidermal cells. The reduction of the activity or function, if appropriate of the expression, of BI-1 is described extensively in WO 2003020939. The skilled worker finds in WO 2003020939 the sequences which code for BI-1 proteins and can also identify BI-1 with the method provided in WO 2003020939.

The reduction of the activity or function, if appropriate of the expression, of NaOX is described extensively in PCT/EP/03/07589, which is herewith expressly incorporated into the present description. The description of the abovementioned publication describes processes and methods for lessening or inhibiting the activity or function of NaOX, and the examples indicate specifically how this can be realized. The reduction or inhibition of the activity or function of NaOX is especially preferably carried out in accordance with the embodiments especially preferred in PCT/EP/03/07589 and the examples and in the organisms shown therein as being especially preferred, in particular in a plant, for example constitutively, or a part thereof, for example in a tissue, but especially advantageously at least in the epidermis or in a considerable part of the epidermal cells. The skilled worker finds in PCT/EP/03/07589 the sequences which code for NaOX proteins and can also identify NaOX with the method provided in PCT/EP/03/07589.

The terms "to lessen", "to reduce" or "to repress" or their substantives are used synonymously in the present text.

"Lessening", "reduction" or "repression" or their verbs are understood as meaning, in accordance with the invention, that the activity in the plant is lower than in a control plant or is lower in a part of a plant than in the same part of a control plant, for example in an organ, an organelle, a tissue or a cell. In one embodiment, the activity of the abovementioned polypeptide is 10%, 20%, 30%, 40%, 50%, 60%, 70%, 80%, 90%, 95%, 97%, 99% or more lower than in the control. In one embodiment, no expression of the abovementioned polypeptide takes place. As a consequence, these terms also comprise the complete inhibition or blocking of an activity, for example by the knock-out of a gene.

"Reduction", "to reduce", "lessening" or "to lessen", "repression" or "to repress" comprise the partial or essentially complete inhibition or blocking of the functionality of a protein, based on a variety of cell-biological mechanisms.

Lessening within the purpose of the invention also comprises a quantitative reducing of a protein down to an essentially complete absence of the protein (i.e. lack of detectability of activity or function or lack of immunological detectability of the protein). Here, the expression of a certain protein or the activity or function in a cell or an organism is reduced by preferably more than 50%, especially preferably by more than 80%, very especially preferably by more than 90%.

For example, the expression of a nucleic acid molecule for a stomatin STM1 protein, for example in combination with a tissue-specific increase in the activity of a Bax inhibitor-1 protein may take place in the mesophyll tissue. The reduction of the stomatin STM1 protein quantity in a transgenic plant which for example overexpresses BI-1 in the mesophyll tissue offers the possibility of generating a complete and comprehensive fungal resistance in the plant.

In a further embodiment, the increase in the polypeptide quantity, activity or function of a Bax Inhibitor 1 protein from *Hordeum vulgare* (GenBank Acc.-No.: AJ290421), from *Nicotiana tabacum* (GenBank Acc.-No.: AF390556), rice (GenBank Acc.-No.: AB025926), *Arabidopsis* (GenBank Acc.-No.: AB025927) or tobacco and oilseed rape (GenBank Acc.-No.: AF390555, Bolduc N et al. (2003) Planta 216:377-386) or of ROR2 (for example from barley (GenBank Acc.-No.: AY246906), SnAP34 (for example from barley (GenBank Acc.-No.: AY247208) and/or of the lumenal binding protein BiP for example from rice (GenBank Acc.-No. AF006825) is effected in combination with the reduction in the protein quantity or activity or function of the proteins RacB (for example from barley (GenBank Acc.-No.: AJ344223), CSL1 (for example from *Arabidopsis* (GenBank Acc.-No.: NM116593), HvNaOX (for example from barley (GenBank Acc.-No.: AJ251717), and/or MLO (for example from barley (GenBank Acc.-No. Z83834). As a consequence, in one embodiment, at least one of the abovementioned genes which are suitable for overexpression or increased activity is activated or overexpressed and/or at least one of the abovementioned genes which is suitable for reduction is reduced.

An increase in the expression can be obtained as described herein. An increase in the expression or function is understood as meaning herein both the activation or enhancement of the expression or function of the endogenous protein, including a de novo expression, and an increase or enhancement by expression of a transgenic protein or factor.

For the purposes of the invention, "organism" means "non-human organisms" as long as the term relates to a viable multi-celled organism.

For the purposes of the invention, "plants" means all dicotyledonous or monocotyledonous plants. Preferred are plants which can be subsumed under the class of the Liliatae (Monocotyledoneae or monocotyledonous plants). The term includes the mature plants, seeds, shoots and seedlings, and parts, propagation material, plant organs, tissue, protoplasts, callus and other cultures, for example cell cultures derived from the above, and all other types of associations of plant cells which give functional or structural units. Mature plants means plants at any developmental stage beyond the seedling stage. Seedling means a young, immature plant in an early developmental stage.

"Plant" also comprises annual and perennial dicotyledonous or monocotyledonous plants and includes by way of example, but not by limitation, those of the genera *Bromus, Asparagus, Pennisetum, Lolium, Oryza, Zea, Avena, Hordeum, Secale, Triticum, Sorghum* and *Saccharum*.

In a preferred embodiment, the method according to the invention is applied to monocotyledonous plants, for example from the family Poaceae, especially preferably to the genera *Oryza, Zea, Avena, Hordeum, Secale, Triticum, Sorghum* and *Saccharum*, very especially preferably to agriculturally important plants such as, for example, *Hordeum vulgare* (barley), *Triticum aestivum* (wheat), *Triticum aestivum* subsp. *spelta* (spelt), Triticale, *Avena sativa* (oats), *Secale cereale* (rye), *Sorghum bicolor* (sorghum), *Zea mays* (maize), *Saccharum officinarum* (sugar cane) or *Oryza sativa* (rice). Thus, in a preferred embodiment, the expression or activity of the stomatin STM1 protein or polynucleotide is reduced in one of these plants.

"Epidermal tissue" or epidermis means the external tissue layers of the plants. It can be single layered or multiple layered; and there is epidermis-"enriched" gene expression, such as, for example, Cer3, which can act as marker, exists; Hannoufa, A. (1996) Plant J. 10 (3), 459-467.

By "epidermis", the skilled worker preferably means the predominant dermal tissue of primary aerial plant parts, such as of the shoots, the leaves, flowers, fruits and seeds.

The epidermal cells excrete a water-repellent layer, the cuticle, towards the outside. The roots are surrounded by the rhizodermis, which resembles the epidermis in many ways, but also differs substantially therefrom. The epidermis develops from the outermost layer of the apical meristem. The origin of the rhizodermis, in contrast, is less clear. Phylogenetically speaking, it can be assigned either to the calyptra or to the primary bark, depending on the species. A large number of functions can be ascribed to the epidermis: it protects the plant from dehydration and regulates the transpiration rate. It protects the plant from a wide range of chemical and physical external factors and against feeding animals and attack by parasites. It is involved in the gas exchange, in the secretion of certain metabolites and in the absorption of water. It contains receptors for light and mechanical stimuli. It therefore acts as signal transformer between the environment and the plant. In accordance with the various functions, the epidermis comprises a number of differently differentiated cells. Other aspects are species having specific variants and different organization of the epidermides in the individual parts of a plant. Essentially, it consists of three categories of cells: the "actual" epidermal cells, the cells of the stomata and of the trichomes (Greek: trichoma, hair), which are epidermal appendages with different shapes, structures and functions.

The "actual", i.e. the least specialized epidermal cells, account for most of the bulk of the cells of the epidermal tissue. In topview, they appear either polygonal (slab or plate shaped) or elongated. The walls between them are often wavy or sinuate. It is not known what induces this shape during development; existing hypotheses only offer unsatisfactory explanations herefor. Elongated epidermal cells can be found in organs or parts of organs that are elongated themselves, thus, for example, in stems, petioles, leaf veins and on the leaves of most monocots. The upper surface and undersurface of laminae can be covered in epidermides with different structures, it being possible for the shape of the cells, the wall thickness and the distribution and number of specialized cells (stomata and/or trichomes) per unit area to vary. A high degree of variation is also found within individual families, for example in the Crassulaceae. In most cases, the epidermis consists of a single layer, though multi-layered water-storing epidermides have been found among species from a plurality of families (Moraceae: most *Ficus* species; Piperaceae: Peperonia, Begoniaceae, Malvaceae and the like). Epidermal cells secrete a cuticle to the outside which covers all epidermal surfaces as an uninterrupted film. It may either be smooth or structured by bulges, rods, folds and furrows. However, the folding of the cuticle, which can be observed when viewing the surface, is not always caused by the formation of cuticular rods. Indeed, there are cases where cuticular folding is merely the expression of the underlying bulges of the cell wall. Epidermal appendages of various form, structure and function are referred to as trichomes and, in the present context, likewise come under the term "epidermis". They occur in the form of protective hairs, supportive hairs and gland hairs in the form of scales, different papillae and, in the case of roots, as absorbent hairs. They are formed exclusively by epidermal cells. Frequently, a trichome is formed by only one such cell, however, occasionally, more than one cell is involved in its formation.

The term "epidermis" likewise comprises papillae. Papillae are bulges of the epidermal surface. The textbook example thereof is the papillae on flower surfaces of the pansy (*Viola tricolor*) and the leaf surfaces of many species from tropical rain forests. They impart a velvet-like consistency to the surface. Some epidermal cells can form water stores. A typical example is the water vesicles at the surfaces of many *Mesembryanthemum* species and other succulents. In some plants, for example in the case of campanula (*Campanula persicifolia*), the outer walls of the epidermis are thickened like a lens.

The main biomass of all tissues is the parenchyma. The parenchymatic tissues include the mesophyll which, in leaves, can be differentiated into palisade parenchyma and spongy parenchyma. Accordingly the skilled worker understands, by mesophyll, a parenchymatic tissue. Parenchymatic cells are always alive, in most cases isodiametric, rarely elongated. The pith of the shoots, the storage tissues of the fruits, seeds, the root and other underground organs are also to be considered as parenchymas, as is the mesophyll. "Mesophyll tissue" means the foliar tissue between the epidermal layers, and consists of palisade tissue, spongy tissue and the vascular bundles of the leaf.

In the leaves of most ferns and phanerogams, especially in the case of the dicots and many monocots, the mesophyll is subdivided into palisade parenchymas and spongy parenchymas. A "typical" leaf is of dorsiventral organization. In most cases, the palisade parenchyma is at the upper surface of the leaf immediately underneath the epidermis. The spongy parenchyma fills the underlying space. It is interspersed by a voluminous intercellular system whose gas space is in direct contact with the external space via the stomata.

The palisade parenchyma consists of elongated cylindrical cells. In some species, the cells are irregular, occasionally bifurcate (Y-shaped: arm palisade parenchyma). Such variants are found in ferns, conifers and a few angiosperms (for example in some *Ranunculaceae* and *Caprifoliaceae* species [example: elder]). Besides the widest-spread organization form which has just been described, the following variants have been found:

palisade parenchyma at the leaf undersurface. Particularly conspicuously in scaly leaves. (For example arbor vitae (*thuja*), and in the leaves of wild garlic (*Allium ursinum*).

Palisade parenchyma at both leaf surfaces (upper surface and undersurface). Frequently found in plants of dry habitats (xerophytes). Example: prickly lettuce (*Lactuca serriola*);

Ring-shaped closed palisade parenchyma: in cylindrically organized leaves and in needles from conifers.

The variability of the cells of the spongy parenchyma, and the organization of the spongy parenchyma itself, are even more varied than that of the palisade parenchyma. It is most frequently referred to as aerenchyma since it comprises a multiplicity of interconnected intercellular spaces.

The mesophyll may comprise what is known as the assimilation tissue, but the terms mesophyll and assimilation tissue are not to be used synonymously. There are chloroplast-free leaves whose organization differs only to a minor extent from comparable green leaves. As a consequence, they comprise mesophyll, but assimilation does not take place; conversely, assimilation also takes place in, for example, sections of the shoot. Further aids for characterizing epidermis and mesophyll can be found by the skilled worker for example in v. GUTTENBERG, H.: Lehrbuch der Allgemeinen Botanik [Textbook of general botany]. Berlin: Akademie-Verlag 1955 (5th Ed.), HABERLANDT, G.: Physiologische Pflanzenanatomie [Physiological plant anatomy]. Leipzig: W. Engelmann 1924 (6th Ed.); TROLL, W.: Morphologie der Pflanzen [Plant morphology]. Volume 1: Vegetationsorgane [Vegetation organs]. Berlin: Gebr. Borntraeger, 1937; TROLL, W.: Praktische Einführung in die Pflanzenmorphologie [Practical introduction to plant morphology]. Jena: VEB G. Thieme Verlag 1954/1957; TROLL, W., HÖHN, K.: Allgemeine Botanik [General botany]. Stuttgart: F. Enke Verlag, 1973 (4th Ed.)

As a consequence, epidermis or epidermal cells can be characterized in histological or biochemical, including molecular-biochemical, terms. In one embodiment, the epidermis is characterized in biochemical terms. In one embodiment, the epidermis can be characterized by the activity of one or more of the following promoters:

WIR5 (=GstA1), acc. X56012, Dudler & Schweizer, unpublished.
GLP4, acc. AJ310534; Wei, Y.; (1998) Plant Molecular Biology 36, 101-112.
GLP2a, acc. AJ237942, Schweizer, P., (1999). Plant J 20, 541-552.
Prx7, acc. AJ003141, Kristensen B K, 2001. Molecular Plant Pathology, 2(6), 311-317
GerA, acc. AF250933; Wu S, 2000. Plant Phys Biochem 38, 685-698
OsROC1, acc. AP004656
RTBV, acc. AAV62708, AAV62707; Klöti, A, 1999, PMB 40, 249-266
Cer3; Hannoufa, A. (1996), Plant J. 10 (3), 459-467.

In another embodiment, the epidermis is characterized in that only some of the promoters are active, for example 2, 3, 5 or 7 or more, but at least one of the abovementioned promoters is active. In one embodiment, the epidermis is characterized in that all the abovementioned promoters are active in the tissue or the cell.

In one embodiment, the expression or activity of the stomatin STM1 protein or polynucleotide in the epidermis is reduced by the expression of an inhibitory molecule under the control of an epidermis-specific promoter, in particular under the control of one of the abovementioned promoters. Examples of inhibitory molecules are listed hereinbelow, for example RNAi, antisense-RNA, microRNA, cosuppression, antibodies and other methods which are known to the skilled worker. The epidermis-specific expression of an inhibitory molecule in the epidermis is particularly advantageous for increasing the resistance of a plant to mildew.

As a consequence, mesophyll or mesophyll cells can be characterized in biochemical, including molecular-biological, or histological terms. In one embodiment, the mesophyll is characterized in biochemical terms. In one embodiment, the mesophyll can be characterized by the activity of one or more of the following promoters:

PPCZm1 (=PEPC); Kausch, A. P., (2001) Plant Mol. Biol. 45, 1-15
OsrbcS, Kyozuka et al Plant Phys: 1993 102: Kyozuka J, 1993. Plant Phys 102, 991-1000
OsPPDK, acc. AC099041.
TaGF-2.8, acc. M63223; Schweizer, P., (1999). Plant J 20, 541-552.
TaFBPase, acc. X53957;
TaWIS1, acc. AF467542; US 200220115849
HvBIS1, acc. AF467539; US 200220115849
ZmMIS1, acc. AF467514; US 200220115849
HvPR1a, acc. X74939; Bryngelsson et al. Molecular Plant-Microbe Interactions (1994)

HvPR1b, acc. X74940; Bryngelsson et al. Molecular Plant-Microbe Interactions (1994)
HvB1,3gluc; acc. AF479647
HvPrx8, acc. AJ276227; Kristensen et al MPP 2001 (see above)
HvPAL, acc. X97313; Wei, Y.; (1998) Plant Molecular Biology 36, 101-112.

In another embodiment, the mesophyll is characterized in that only some of the promoters are active, for example 2, 3, 5 or 7 or more, but at least one of the abovementioned promoters is active. In one embodiment, the mesophyll is characterized in that all the abovementioned promoters are active in the tissue or the cell.

In one embodiment, all of the abovementioned promoters are active in the epidermis of a plant which is used or generated in accordance with the invention or of a plant according to the invention in the epidermis and in the mesophyll. In one embodiment, only some of the abovementioned promoters are active, for example 2, 5, 7 or more, but at least one of the promoters enumerated above is in each case active.

In one embodiment, the expression or activity of the stomatin STM1 protein or polynucleotide in the mesophyll is reduced by the expression of an inhibitory molecule under the control of a mesophyll-specific promoter, in particular under the control of one of the abovementioned promoters. Examples of inhibitory molecules are listed hereinbelow, for example RNAi, antisense-RNA, microRNA, cosuppression, antibodies and other methods which are known to the skilled worker. The epidermis-specific expression of an inhibitory molecule in the mesophyll is particularly advantageous for increasing the resistance of a plant to *Septoria* and/or rusts.

In one embodiment, the expression or activity of the stomatin STM1 protein or polynucleotide in the mesophyll and in the epidermis is reduced by the expression of inhibitory molecules under the control of mesophyll- and/or epidermis-specific promoters, in particular under the control of the abovementioned promoters. Examples of inhibitory molecules are mentioned hereinbelow, for example RNAi, antisense-RNA, antibodies and others.

"Nucleic acids" means biopolymers of nucleotides which are linked with one another via phosphodiester bonds (polynucleotides, polynucleic acids). Depending on the type of sugar in the nucleotides (ribose or deoxyribose), one distinguishes the two classes of the ribonucleic acids (RNA) and the deoxyribonucleic acids (DNA).

The term "crop" means all plant parts obtained by growing plants agriculturally and collected within the harvesting process.

"Resistance" means the preventing, the repressing, the reducing or the weakening of disease symptoms of a plant as the result of infection by a pathogen. The symptoms can be manifold, but preferably comprise those which directly or indirectly lead to an adversely affect on the quality of the plant, on the quantity of the yield, on the suitability for use as feed or foodstuff, or else which make sowing, growing, harvesting or processing of the crop more difficult.

In a preferred embodiment, the following disease symptoms are weakened, reduced or prevented: formation of pustules and hymenia on the surfaces of the affected tissues, maceration of the tissues, spreading necroses of the tissue, accumulation of mycotoxins, for example from *Fusarium graminearum* or *F. culmorum*.

"Conferring", "existing", "generating" or "increasing" a pathogen resistance means that the defence mechanisms of a certain plant or in a part of a plant, for example in an organ, a tissue, a cell or an organelle, have an increased resistance to one or more pathogens as the result of using the method according to the invention in comparison with a suitable control, for example the wildtype of the plant ("control plant", "starting plant"), to which the method according to the invention has not been applied, under otherwise identical conditions (such as, for example, climatic conditions, growing conditions, type of pathogen and the like). Preferably, at least the epidermis and/or mesophyll tissue in a plant, or the organs which have an epidermis and/or mesophyll tissue, have an increased resistance to the pathogens. For example, the resistance in the leaves is increased. In one embodiment, the resistance in lemma, palea and/or glume (anther primordium) is increased.

In one embodiment, the activity of the protein according to the invention, stomatin STM1, is therefore reduced in the abovementioned organs and tissues.

In this context, the increased resistance preferably manifests itself in a reduced manifestation of the disease symptoms, where disease symptoms—in addition to the abovementioned adverse effects—also comprises for example the penetration efficiency of a pathogen into the plant or the plant cell, or the proliferation efficiency in or on the same. In this context, the disease symptoms are preferably reduced by at least 10% or at least 20%, especially preferably by at least 40% or 60%, very especially preferably by at least 70% or 80%, most preferably by at least 90% or 95%.

For the purposes of the invention, "pathogen" means organisms whose interactions with a plant lead to the above-described disease symptoms; in particular, pathogens means organisms from the Kingdom Fungi. Preferably, pathogen is understood as meaning a pathogen which penetrates epidermis or mesophyll cells, especially preferably pathogens which penetrate plants via stomata and subsequently penetrate mesophyll cells. Organisms which are preferably mentioned in this context are those from the phyla Ascomycota and Basidiomycota. Especially preferred in this context are the families Blumeriaceae, Pucciniaceae, Mycosphaerellaceae and Hypocreaceae.

Especially preferred are organisms of these families which belong to the genera *Blumeria, Puccinia, Fusarium* or *Mycosphaerella*.

Very especially preferred are the species *Blumeria graminis, Puccinia triticina, Puccinia striiformis, Mycosphaerella graminicola, Stagonospora nodorum, Fusarium graminearum, Fusarium culmorum, Fusarium avenaceum, Fusarium poae* and *Microdochium nivale*.

However, it is to be assumed that the reduction in the expression of Hvstomatin STM1, its activity or function also brings about a resistance to further pathogens. Changes in the cell wall structure may constitute a basic mechanism of pathogen resistance, as shown, for example, in Jacobs A K et al. (2003) Plant Cell, 15(11):2503-13.

Especially preferred are Ascomycota such as, for example, *Fusarium oxysporum (fusarium* wilt on tomato), *Septoria nodorum* and *Septoria tritici* (glume blotch on wheat), Basidiomycetes such as, for example, *Puccinia graminis* (stem rust on wheat, barley, rye, oats), *Puccinia recondita* (leaf rust on wheat), *Puccinia dispersa* (leaf rust on rye), *Puccinia hordei* (leaf rust on barley), *Puccinia coronata* (crown rust on oats).

In one embodiment, the method according to the invention leads to a resistance in
barley to the pathogen:
*Puccinia graminis* f.sp. *hordei* (barley stem rust),
in wheat to the pathogens:
  *Fusarium graminearum, Fusarium avenaceum, Fusarium culmorum, Puccinia graminis* f.sp. *tritici, Puccinia recondita* f.sp. *tritici, Puccinia striiformis*, Septoria nodorum, Septoria tritici, Septoria avenae or Puccinia graminis f.sp. tritici (wheat stem rust),
in maize to the pathogens:
Fusarium moniliforme* var. *subglutinans, Puccinia sorghi* or *Puccinia polysora,* in *sorghum* to the pathogens:

*Puccinia purpurea, Fusarium moniliforme, Fusarium graminearum* or *Fusarium oxysporum,* in soybean to the pathogens

*Phakopsora pachyrhizi* and *Phakopsora meibromae.*

In a preferred embodiment, the invention relates to a stomatin STM1 polypeptide which has the activity shown in the examples.

In one embodiment, a stomatin STM1 protein is understood as meaning a protein with a homology to one of the amino acid sequences shown in SEQ ID No: 2, 4, 6, 8, 10, 12, 14, 15, 16 or 17 or in the figures, for example a stomatin STM1 polypeptide from maize (ZmStomatin STM1) as in SEQ ID NO: 5 and/or from rice (*Oryza sativa*) as shown in SEQ ID NO: 3ar from *A. thaliana* as shown in SEQ ID NO: 7, 9, 11 and/or 13, or according to one of the consensus sequences as shown in SEQ ID NO.: 15, 16 or 17, or a functional fragment thereof. In one embodiment, the invention relates to functional equivalents of the abovementioned polypeptide sequences.

"Polypeptide quantity" means for example the number of molecules, or moles, of stomatin STM1 polypeptide molecules in an organism, a tissue, a cell or a cell compartment. "Reducing" the polypeptide quantity means the molar reduction in the number of stomatin STM1 polypeptides, in particular of those shown in SEQ ID No: 2, 4, 6, 8, 10, 12, 14, 15, 16 or 17, in an organism, a tissue, a cell or a cell compartment—for example by one of the methods described hereinbelow—in comparison with a suitable control, for example the wildtype (control plant) of the same genus and species to which this method has not been applied, under otherwise identical conditions (such as, for example, culture conditions, age of the plants and the like). The reduction in this context amounts to at least 5%, preferably at least 10% or at least 20%, especially preferably at least 40% or 60%, very especially preferably at least 70% or 80%, most preferably at least 90% or 99%.

The present invention furthermore relates to the generation of a pathogen resistance by reducing the function or activity of a TOMATIN polypeptide comprising the sequences shown in SEQ ID No: 2, 4, 6, 8, 10, 12, 14, 15, 16 or 17 or of a homolog thereof and/or a polypeptide which has a homology of at least 40% with the above, and/or of a functional equivalent of the abovementioned polypeptides.

Homology between two nucleic acid sequences is understood as meaning the identity of the nucleic acid sequence over in each case the entire sequence length, in a preferred embodiment over the entire expressed sequence length, preferably cDNA, yet more preferably over the coding sequence, preferably CDS, which is calculated by comparison with the aid of the program algorithm GAP (Wisconsin Package Version 10.0, University of Wisconsin, Genetics Computer Group (GCG), Madison, USA; Altschul et al. (1997) Nucleic Acids Res. 25:3389ff), setting the following parameters:

| | |
|---|---|
| Gap weight: 50 | Length weight: 3 |
| Average match: 10 | Average mismatch: 0 |

For example, a sequence which has at least 80% homology with the sequence SEQ ID NO: 1 at the nucleic acid level is understood as meaning a sequence which, upon comparison with the sequence SEQ ID NO: 1 by the above program algorithm with the above parameter set, has at least 80% homology.

"Identity between two proteins" is understood as meaning the identity of the amino acids over a specific protein region, preferably the entire length of the protein, in particular the identity which is calculated by comparison with the aid of software, for example the Lasergene software from DNA Star Inc., Madison, Wis. (USA) using the CLUSTAL methods (Higgins et al., 1989), Comput. Appl. Biosci., 5 (2), 151). Homologies can also be calculated with the aid of the Lasergene software from DNA Star Inc., Madison, Wis. (USA) using the CLUSTAL method (Higgins et al., 1989), Comput. Appl. Biosci., 5 (2), 151).

For the alignments shown herein (for example as in FIG. 4), the preset parameters from the page clustalw/Last updated: Oct. 17, 2005 11:27:35 were used with the following programs from FTP DIRECTORY: ebi.ac.uk/pub/software/unix/clustalw/:

ParClustal0.1.tar.gz [Nov. 28, 2001] 823975
ParClustal0.2.tar.gz [Jun. 27, 2002] 2652452
README [Jun. 13, 2003] 673
clustalw1.8.UNIX.tar.gz [Jul. 4, 1999] 4725425
clustalw1.8.mp.tar.gz [May 2, 2000] 174859
clustalw1.81.UNIX.tar.gz [Jun. 7, 2000] 555655
clustalw1.82.UNIX.tar.gz [Feb. 6, 2001] 606683
clustalw1.82.mac-osx.tar.gz [Oct. 15, 2002] 669021
clustalw1.83.UNIX.tar.gz [Jan. 30, 2003] 166863

Homology between two polypeptides is preferably understood as meaning the identity of the amino acid sequence over the indicated entire sequence length which is calculated by comparison with the aid of the program algorithm GAP (Wisconsin Package Version 10.0, University of Wisconsin, Genetics Computer Group (GCG), Madison, USA), setting the following parameters:

| | |
|---|---|
| Gap weight: 8 | Length weight: 2 |
| Average match: 2.912 | Average mismatch: −2.003 |

For example, a sequence which has at least 80% homology at the polypeptide level with the sequence SEQ ID NO: 2 is understood as meaning a sequence which, upon comparison with the sequence SEQ ID NO: 2 by the above program algorithm with the above parameter set has at least 80% homology.

In a preferred embodiment of the present invention, the stomatin STM1 protein activity, function or polypeptide quantity is reduced in the plant or in a part of the plant, for example in a plant organ, plant tissue, a plant cell or a part of a plant cell, for example a plant-specific organelle.

For example, the stomatin STM1 protein is encoded by a nucleic acid molecule comprising a nucleic acid molecule selected from the group consisting of:

a) nucleic acid molecule which codes for a polypeptide which comprises the sequence shown in SEQ ID No: 15, 16 or 17;
b) nucleic acid molecule which comprises at least one polynucleotide of the sequence according to SEQ ID No: or 3, 5, 7, 9, 11, or 13;
c) nucleic acid molecule which codes for a polypeptide whose sequence has 40%, 50%, 60%, 70%, 80%, 90%, 95%, 97%, 98%, 99% or more identity to the sequences SEQ ID No: 15, or 17;

d) nucleic acid molecule according to (a) to (c) which codes for a functional fragment or an epitope of the sequences as shown in SEQ ID No: 516 or 17;
e) nucleic acid molecule which codes for a polypeptide which is recognized by a monoclonal antibody directed against a polypeptide which is encoded by the nucleic acid molecules as shown in (a) to (c); and
f) nucleic acid molecule which hybridizes under stringent conditions with a nucleic acid molecule as shown in (a) to (c); or their part-fragments of at least 15 nucleotides (nt), preferably 20 nt, 30 nt, 50 nt, 100 nt, 200 nt or 500 nt;
g) nucleic acid molecule which can be isolated from a DNA library using a nucleic acid molecule as shown in (a) to (c) or their part-fragments of at least 15 nt, preferably 20 nt, 30 nt, 50 nt, 100 nt, 200 nt or 500 nt, as probe under stringent hybridization conditions;
or comprises a complementary sequence thereof or constitutes a functional equivalent thereof.

Preferably, the activity of the abovementioned polypeptides is reduced in the epidermal and/or mesophyll cells of a plant as detailed above.

In one embodiment, the activity of stomatin STM1 is reduced in lemma, palea and/or glume.

"Epitope" is understood as meaning the regions of an antigen which determine the specificity of the antibodies (the antigenic determinant). Accordingly, an epitope is the portion of an antigen which actually comes into contact with the antibody. Such antigenic determinants are those regions of an antigen to which the T-cell receptors react and, as a consequence, produce antibodies which specifically bind the antigenic determinant/epitope of an antigen. Accordingly, antigens, or their epitopes, are capable of inducing the immune response of an organism with the consequence of the formation of specific antibodies which are directed against the epitope. Epitopes consist for example of linear sequences of amino acids in the primary structure of proteins, or of complex secondary or tertiary protein structures. A hapten is understood as meaning a epitope which is dissociated from the context of the antigen environment. Although haptens have by definition an antibody directed against them, haptens are, under certain circumstances, not capable of inducing an immune response in an organism, for example after an injection. To this end, haptens are coupled with carrier molecules. An example which may be mentioned is dinitrophenol (DNP), which, after coupling to BSA (bovine serum albumine), has been used for generating antibodies which are directed against DNP. (Bohn, A., König, W. 1982).

Haptens are therefore substances (frequently small molecules) which, while they themselves do not trigger immune response, will indeed trigger such a response when coupled to a large molecular carrier.

The antibodies generated thus also include those which can bind to the hapten as such.

In one embodiment, the present invention relates to an antibody against a polypeptide characterized herein, in particular to a monoclonal antibody which binds a polypeptide which comprises an AA sequence or consists thereof, as shown in the sequences shown in SEQ ID No: 15, 16 or 17.

Antibodies within the scope of the present invention can be used for identifying and isolating polypeptides disclosed in accordance with the invention from organisms, preferably plants, especially preferably monocotyledonous plants. The antibodies can either be monoclonal, polyclonal or synthetic in nature or else consist of antibody fragments such as Fab, Fv or scFv fragments, which are formed by proteolytic degradation. "Single chain" Fv (scFv) fragments are single-chain fragments which, linked via a flexible linker sequence only comprise the variable regions of the heavy and light antibody chains. Such scFv fragments can also be produced as recombinant antibody derivatives. A presentation of such antibody fragments on the surface of filamentous phages makes possible the direct selection, from combinatory phage libraries, of scFv molecules which bind with high affinity.

Monoclonal antibodies can be obtained in accordance with the method described by Köhler and Milstein (Nature 256 (1975), 495).

"Functional equivalents" of a stomatin STM1 protein preferably means those polypeptides which have at least 40% homology with the polypeptides described by the sequences SEQ ID No: 15, 16 or 17 and which have essentially the same properties or function. Preferably, the homology amounts to 50%, 60%, 70%, 80%, 90%, 95%, 97%, 98%, 99% or more.

The functional equivalence can be determined for example by comparing the phenotypes of test organisms after expression of the polypeptides in question, under the most identical conditions possible, or after reduction of the expression or activity of the polypeptides to be compared, in the source organisms in question.

"Essentially identical properties" of a functional equivalent means above all imparting a pathogen-resistant phenotype or imparting or increasing the pathogen resistance to at least one pathogen when reducing the polypeptide quantity, activity or function of said functional stomatin STM1 protein equivalent in a plant, organ, tissue, part or cells, in particular in epidermal or mesophyll cells of same, preferably measured by the penetration efficiency of a pathogen, as shown in the examples.

"Analogous conditions" means that all basic conditions such as, for example, culture or growth conditions, assay conditions (such as buffers, temperature, substrates, pathogen concentration and the like) between the experiments to be compared are kept identical and that the set-ups only differ by the sequence of the stomatin STM1 polypeptides to be compared, by their source organism and, if appropriate, by the pathogen.

"Functional equivalents" also means natural or artificial mutation variants of the stomatin STM1 polypeptides as shown in SEQ ID No: 15, 16 or 17 and homologous polypeptides from other monocotyledonous and dicotyledonous plants which furthermore have essentially identical properties. Preferred are homologous polypeptides from preferred plants described herein. The sequences from other plants, which sequences are homologous to the stomatin STM1 protein sequences disclosed within the scope of the present invention, can be found readily for example by database search or by screening gene libraries using the stomatin STM1 protein sequences as search sequence or probe.

Functional equivalents can also be derived for example from one of the polypeptides according to the invention as shown in SEQ ID No: 15, or 17 by substitution, insertion or deletion and can have at least 60%, preferably at least 80%, by preference at least 90%, especially preferably at least 95%, very especially preferably at least 98% homology with these polypeptides and are distinguished by essentially identical properties to the polypeptides as shown in SEQ ID No: 15, 16 or 17.

Functional equivalents are also nucleic acid molecules which are derived from the nucleic acid sequences according to the invention as shown in SEQ ID No: 1, 3, 5, 7, 9, 11 or 13, 1, 3, 5, 7, 9, 11 or 13 by substitution, insertion or deletion and have at least 60%, preferably 80%, by preference at least 90%, especially preferably at least 95%, very especially preferably at least 98% homology with one of the polynucleotides according to the invention as shown in SEQ ID No: or, 3, 5, 7, 9, 11 or 13 and code for polypeptides with essentially identical properties to polypeptides as shown in SEQ ID No: 15, 16 or 17.

Examples of the functional equivalents of the stomatin STM1 proteins as shown in SEQ ID No: 15, or 17 which are to be reduced in the method according to the invention can be found by homology comparisons from databases, from organisms whose genomic sequence is known.

Screening cDNA libraries or genomic libraries of other organisms, preferably of the plant species mentioned further below, which are suitable as transformation hosts, using the nucleic acid sequence described in SEQ ID No: or, 3, 5, 7, 9, 11 or 13 or parts of the same as probe is also a method known to the skilled worker for identifying homologs in other species. In this context, the probes derived from the nucleic acid sequence as shown in SEQ ID No: or 1, 3, 51 or 1 have a length of at least 20 bp, preferably at least 50 bp, especially preferably at least 100 bp, very especially preferably at least 200 bp, most preferably at least 400 bp. The probe can also be one or more kilobases in length, for example 1 kb, 1.5 kb or 3 kb. A DNA strand which is complementary to the sequences described in SEQ ID No: or, or a fragment of same strand with a length of between 20 bp and several kilobases may also be employed for screening the libraries.

In the method according to the invention, those DNA molecules which hybridize under standard conditions with the nucleic acid molecules described by SEQ ID No: or 13 and which code for stomatin STM1 proteins, with the nucleic acid molecules which are complementary to the above or with parts of the above and which, as complete sequences, code for polypeptides which have identical properties to the polypeptides described in SEQ ID No: 15, 16 or 17, 101115, 16 or 17, may also be used.

"Standard hybridization conditions" is to be understood in the broad sense and means, depending on the application, stringent or else less stringent hybridization conditions. Such hybridization conditions are described, inter alia, in Sambrook J, Fritsch E F, Maniatis T et al., in Molecular Cloning (A Laboratory Manual), 2nd edition, Cold Spring Harbor Laboratory Press, 1989, pages 9.31-9.57) or in Current Protocols in Molecular Biology, John Wiley & Sons, N.Y. (1989), 6.3.1-6.3.6.

The skilled worker would choose hybridization conditions which allow him to differentiate between specific and unspecific hybridizations.

For example, the conditions during the wash step can be selected from among low-stringency conditions (with approximately 2×SSC at 50° C.) and high-stringency conditions (with approximately 0.2×SSC at 50° C., preferably at 65° C.) (20×SSC: 0.3M sodium citrate, 3M NaCl, pH 7.0). Moreover, the temperature during the wash step can be raised from low-stringency conditions at room temperature, approximately 22° C., to higher-stringency conditions at approximately 65° C. The two parameters, salt concentration and temperature can be varied simultaneously or else singly, keeping in each case the other parameter constant. During the hybridization, it is also possible to employ denaturant agents such as, for example, formamide or SDS. In the presence of 50% formamide, the hybridization is preferably carried out at 42° C. Some examples of conditions for hybridization and wash step are detailed hereinbelow:

(1) Hybridization conditions can be selected for example among the following conditions:
a) 4×SSC at 65° C.,
b) 6×SSC at 45° C.,
c) 6×SSC, 100 μg/ml denatured fragmented fish sperm DNA at 68° C.,
d) 6×SSC, 0.5% SDS, 100 μg/ml denatured salmon sperm DNA at 68° C.,
e) 6×SSC, 0.5% SDS, 100 μg/ml denatured fragmented salmon sperm DNA, 50% formamide at 42° C.,
f) 50% formamide, 4×SSC at 42° C., or
g) 50% (vol/vol) formamide, 0.1% bovine serum albumin, 0.1% Ficoll, 0.1% polyvinylpyrrolidone, 50 mM sodium phosphate buffer pH 6.5, 750 mM NaCl, 75 mM sodium citrate at 42° C., or
h) 2× or 4×SSC at 50° C. (low-stringency condition),
i) 30 to 40% formamide, 2× or 4×SSC at 42° C. (low-stringency condition),
j) 500 mN sodium phosphate buffer pH 7.2, 7% SDS (gN), 1 mM EDTA, 10 μg/ml single stranded DNA, 0.5% BSA (gN) (Church and Gilbert, Genomic sequencing. Proc. Natl. Acad. Sci. U.S.A. 81:1991. 1984)

(2) Wash steps can be selected for example among the following conditions:
a) 0.015 M NaCl/0.0015 M sodium citrate/0.1% SDS at 50° C.
b) 0.1×SSC at 65° C.
c) 0.1×SSC, 0.5% SDS at 68° C.
d) 0.1×SSC, 0.5% SDS, 50% formamide at 42° C.
e) 0.2×SSC, 0.1% SDS at 42° C.
f) 2×SSC at 65° C. (low-stringency condition).

In one embodiment, the hybridization conditions are selected as follows:

A hybridization buffer comprising formamide, NaCl and PEG 6000 is chosen. The presence of formamide in the hybridization buffer destabilizes double-strand nucleic acid molecules, whereby the hybridization temperature can be lowered to 42° C. without thereby reducing the stringency. The use of salt in the hybridization buffer increases the renaturation rate of a duplex, in other words the hybridization efficiency. Although PEG increases the viscosity of the solution, which has a negative effect on the renaturation rates, the presence of the polymer in the solution increases the concentration of the probe in the remaining medium, which increases the hybridization rate. The composition of the buffer is as follows:

| Hybridization buffer |
| --- |
| 250 mM sodium phosphate buffer pH 7.2 |
| 1 mM EDTA |
| 7% SDS (g/v) |
| 250 mM NaCl |
| 10 μg/ml ssDNA |
| 5% polyethylene glycol (PEG) 6000 |
| 40% formamide |

The hybridizations are carried out overnight at 42° C. On the following morning, the filters are washed 3× with 2×SSC+ 0.1% SDS for in each case approximately 10 minutes.

In a further preferred embodiment of the present invention, an increase in the resistance in the method according to the invention is achieved by
(a) reducing the expression of at least one stomatin STM1 protein;
(b) reducing the stability of at least one stomatin STM1 protein or of the mRNA molecules which correspond to this stomatin STM1 protein;
(c) reducing the activity of at least one stomatin STM1 protein;

(d) reducing the transcription of at least one gene which codes for stomatin STM1 protein by expressing an endogenous or artificial transcription factor; or (e) adding, to the food or to the medium, an exonogous factor which reduces the stomatin STM1 protein activity.

"Gene expression" and "expression" are to be understood as being synomymous and mean the realization of the information which is stored in a nucleic acid molecule. Reducing the expression of a gene therefore comprises the reduction of the polypeptide quantity of the encoded protein, for example of the stomatin STM1 polypeptide or of the stomatin STM1 protein function. The reduction of the gene expression of a stomatin STM1 protein gene can be realized in many different ways, for example by one of the methods listed hereinbelow.

"Reduction", "reducing" or "to reduce" in the context of a stomatin STM1 protein or stomatin STM1 protein function is to be interpreted in the broad sense and comprises the partial or essentially complete inhibition or blockage of the functionality of a stomatin STM1 polypeptide in a plant or a part, tissue, organ, cells or seeds derived therefrom, based on different cell-biological mechanisms.

Reducing within the meaning of the invention also comprises a quantitive reduction of a stomatin STM1 polypeptide down to an essentially complete absence of the stomatin STM1 polypeptide (i.e. lack of detectability of stomatin STM1 protein function or lack of immunological detectability of the stomatic STM1 protein). Here, the expression of a certain stomatin STM1 polypeptide or the stomatin STM1 protein function in a cell or an organism is preferably reduced by more than 50%, especially preferably by more than 80%, very especially preferably by more than 90%, in comparison with a suitable control, i.e. to the wildtype of the same type, for example of the same genus, species, variety, cultivar and the like ("control plants"), to which this method has not been applied, under otherwise identical conditions (such as, for example, culture conditions, age of the plants and the like).

In accordance with the invention, there are described various strategies for reducing the expression of a stomatin STM1 protein or a stomatin STM1 protein function. The skilled worker recognizes that a series of further methods is available for influencing the expression of a stomatin STM1 polypeptide or of the stomatin STM1 protein function in the desired manner.

In one embodiment, a reduction in the stomatin STM1 protein function is achieved in the method according to the invention by applying at least one method selected from the group consisting of:

a) introducing a nucleic acid molecule coding for ribonucleic acid molecules suitable for forming double-strand ribonucleic acid molecules (dsRNA), where the sense strand of the dsRNA molecule has at least 30% homology with the nucleic acid molecule according to the invention, for example with one of the nucleic acid molecules as shown in SEQ ID No: or 13, or coding for a consensus sequence as shown in SEQ ID NO.: 15, 16 or 17, or comprises a fragment of at least 17 base pairs, which has at least 50% homology with a nucleic acid molecule according to the invention, for example as shown in SEQ ID No: or or coding for a consensus sequence as shown in SEQ ID NO.: 15, 16 or 17, or with a functional equivalent of same, or introducing (an) expression cassette(s) which ensure(s) their expression.

b) introducing a nucleic acid molecule coding for an antisense ribonucleic acid molecule which has at least 30% homology with the noncoding strand of one of the nucleic acid molecules according to the invention, for example a nucleic acid molecule as shown in SEQ ID No: or or coding for a consensus sequence as shown in SEQ ID NO.: 1516 or 17, or comprising a fragment of at least 15 base pairs with at least 50% homology with a noncoding strand of a nucleic acid molecule according to the invention, for example as shown in SEQ ID No: or or coding for a consensus sequence as shown in SEQ ID NO.: 15, 16 or 17, or with a functional equivalent thereof. Comprised are those methods in which the antisense nucleic acid sequence against a stomatin STM1 protein gene (i.e. genomic DNA sequences) or a stomatin STM1 protein gene transcript (i.e. RNA sequences). Also comprised are α-anomeric nucleic acid sequences.

c) introducing a ribozyme which specifically cleaves, for example catalytically, the ribonucleic acid molecules encoded by a nucleic acid molecule according to the invention, for example as shown in SEQ ID No: or or coding for a consensus sequence as shown in SEQ ID NO.: 15, 16 or 17 or by their functional equivalents, by introducing an expression cassette which ensures the expression of such a ribozyme.

d) introducing an antisense nucleic acid molecule as specified in b), in combination with a ribozyme or with an expression cassette which ensures the expression of the ribozyme.

e) introducing nucleic acid molecules coding for sense ribonucleic acid molecules of a polypeptide according to the invention, for example as shown in the sequences SEQ ID No: 5, 16 or 17, for polypeptides with at least 40% homology with the amino acid sequence of a protein according to the invention, or is a functional equivalent thereof.

f) introducing a nucleic acid sequence coding for a dominant-negative polypeptide suitable for suppressing the stomatin STM1 protein function, or introducing an expression cassette which ensures the expression of this nucleic acid sequence.

g) introducing a factor which can specifically bind stomatin STM1 polypeptides or the DNA or RNA molecules coding for these polypeptides, or introducing an expression cassette which ensures the expression of this factor.

h) introducing a viral nucleic acid molecule which brings about a degradation of mRNA molecules which code for stomatin STM1 protein, or introducing an expression cassette which ensures the expression of this nucleic acid molecule.

i) introducing a nucleic acid construct suitable for inducing a homologous recombination on genes coding for stomatin STM1 protein.

j) introducing one or more mutations into one or more coding gene(s) coding for stomatin STM1 protein for generating a loss of function (for example generation of stop codons, reading-frame shifts and the like).

These and modified methods, and further methods, are known to the skilled worker and extensively described, for example also in PCT/EP2005/003297, which is explicitly included herein by reference with regard to these methods.

Each one of these methods can bring about a reduction in the stomatin STM1 protein expression or stomatin STM1 protein function for the purposes of the invention. A combined use is also feasible. Further methods are known to the skilled worker and can comprise the hindering or prevention of the processing of the stomatin STM1 polypeptide, of the transport of the stomatin STM1 polypeptide or its mRNA, inhibition of the ribosome attachment, inhibition of the RNA splicing, induction of a stomatin-STM1-protein-RNA-degrading enzyme and/or inhibition of the translational elongation or termination.

A reduction in the stomatin STM1 protein function or stomatin STM1 polypeptide quantity is preferably achieved by a reduced expression of an endogenous stomatin STM1 protein gene.

The individual preferred processes shall be described briefly hereinbelow:

a) Introducing a Double-Stranded Stomatin STM1 Protein RNA Nucleic Acid Sequence (Stomatin STM1 Protein dsRNA)

The method of regulating genes by means of double-stranded RNA ("double-stranded RNA interference"; dsR-NAi) has been described many times for animal and plant organisms (e.g. Matzke M A et al. (2000) Plant Mol Biol 43:401-415; Fire A. et al (1998) Nature 391:806-811; WO 99/32619; WO 99/53050; WO 00/68374; WO 00/44914; WO 00/44895; WO 00/49035; WO 00/63364). Efficient gene suppression can also be demonstrated in the case of transient expression, or following the transient transformation, for example as the result of a biolistic transformation (Schweizer P et al. (2000) Plant J 2000 24: 895-903). dsRNAi processes are based on the phenomenon that simultaneously introducing the complementary strand and counterstrand of a gene transcript suppresses the expression of the corresponding gene in a highly efficient manner. The phenotype caused is very similar to that of a corresponding knock-out mutant (Waterhouse P M et al. (1998) Proc Natl Acad Sci USA 95:13959-64).

The dsRNAi method has proved to be particularly efficient and advantageous when reducing the stomatin STM1 protein expression (WO 99/32619).

With regard to the double-stranded RNA molecules, stomatin STM1 protein nucleic acid sequence preferably means one of the sequences as shown in SEQ ID No: 1, 3, 5, 7, 9, 11 or 13, or coding for a consensus sequence as shown in SEQ ID NO.: 15, 16 or 17, or sequences which are essentially identical to those, preferably which have at least 50%, 60%, 70%, 80% or 90% or more identity to these, for example approximately 95%, 96%, 97%, 98%, 99% or more identity to these, or fragments of these with a length of at least 17 base pairs. "Essentially identical" means here that the dsRNA sequence may also have insertions, deletions and individual point mutations in comparison with the stomatin STM1 protein target sequence while still bringing about an efficient reduction in the expression. In one embodiment, the homology as defined above is at least 50%, for example approximately 80%, or approximately 90%, or approximately 100%, between the "sense" strand of an inhibitory dsRNA and a subsection of a stomatin STM1 protein nucleic acid sequence (or between the "antisense" strand and the complementary strand of a stomatin STM1 protein nucleic acid sequence). The length of the subsection is approximately 17 bases or more, for example approximately 25 bases, or approximately 50 bases, approximately 100 bases, approximately 200 bases or approximately 300 bases. Alternatively, an "essentially identical" dsRNA can also be defined as a nucleic acid sequence which is capable of hybridizing under stringent conditions with a part of a stomatin STM1 protein gene transcript.

The "antisense" RNA strand, too, can have insertions, deletions and individual point mutations in comparison with the complement of the "sense" RNA strand. The homology is preferably at least 80%, for example approximately 90%, or approximately 95%, or approximately 100%, between the "antisense" RNA strand and the complement of the "sense" RNA strand.

"Subsection of the "sense" RNA transcript" of a nucleic acid molecule coding for a stomatin STM1 polypeptide or a functional equivalent thereof means fragments of an RNA or mRNA transcribed by a nucleic acid molecule coding for a stomatin STM1 polypeptide or a functional equivalent thereof, preferably by a stomatin STM1 protein gene. In this context, the fragments preferably have a sequence length of approximately 20 bases or more, for example approximately 50 bases, or approximately 100 bases, or approximately 200 bases, or approximately 500 bases. Also comprised is the complete transcribed RNA or mRNA.

The dsRNA can consist of one or more strands of polymerized ribonucleotides. Modifications both of the sugar-phosphate backbone and of the nucleosides may also be present. For example, the phosphodiester bonds of the natural RNA can be modified in such a way that they comprise at least one nitrogen or sulfur heteroatom. Bases can be modified in such a way that the activity of, for example, adenosin deaminase is restricted. Such and further modifications are described hereinbelow in the methods of stabilizing antisense RNA.

To achieve the same purpose, it is, of course, also possible to introduce, into the cell or the organism, a plurality of individual dsRNA molecules, each of which comprises one of the above-defined ribonucleotide sequence segments.

The dsRNA can be prepared enzymatically or fully or partially by chemical synthesis.

If the two strands of the dsRNA are to be combined in one cell or plant, this can be accomplished in various ways:

a) transformation of the cell or plant with a vector which comprises both expression cassettes,
b) cotransformation of the cell or plant with two vectors, where one comprises the expression cassettes with the "sense" strand while the other one comprises the expression cassettes with the "antisense" strand, and/or
c) hybridization of two plants which have been transformed with in each case one vector, where one comprises the expression cassettes with the "sense" strand, while the other one comprises the expression cassettes with the "antisense" strand.

The formation of the RNA duplex can be initiated either externally or internally of the cell. As described in WO 99/53050, the dsRNA can also comprise a hairpin structure, by linking "sense" and "antisense" strand by means of a "linker" (for example an intron). The autocomplementary dsRNA structures are preferred since they only require the expression of a construct and always comprise the complementary strands in an equimolar ratio.

The expression cassettes coding for the "antisense" or "sense" strand of a dsRNA or for the autocomplementary strand of the dsRNA are preferably inserted into a vector and stably (for example using selection markers) inserted into the genome of a plant using the methods described hereinbelow in order to ensure permanent expression of the dsRNA.

The dsRNA can be introduced using a quantity which makes possible at least one copy per cell. Higher quantities (for example at least 5, 10, 100, 500 or 1000 copies per cell) can make, if appropriate, a more efficient reduction.

In order to bring about an efficient reduction in the stomatin STM1 protein expression, 100% sequence identity between dsRNA and a stomatin STM1 protein gene transcript or the gene transcript of a functionally equivalent gene is not necessarily required. Accordingly, there is the advantage that the method tolerates sequence deviations as they can exist as the result of genetic mutations, polymorphisms or evolutionary divergences. The large number of highly conserved amino acid residues between different stomatin STM1 protein sequences of different plants, as shown in the figures with reference to the consensus sequences, allows the conclusion that this polypeptide is highly conserved within plants, so that the expression of a dsRNA derived from one of the disclosed stomatin STM1 protein sequences as shown in SEQ ID No: or should also have an advantageous effect in other plant species.

As the result of the high number of conserved residues and of the homology between the individual stomatin STM1 polypeptides and their functional equivalents, it may also be possible to suppress the expression of further homologous stomatin STM1 polypeptides and/or their functional equivalents of the same organism, or else the expression of stomatin STM1 polypeptides in other, related species, using a single dsRNA sequence which has been generated starting from a specific stomatin STM1 protein sequence of an organism. For this purpose, the dsRNA preferably comprises sequence regions of stomatin STM1 protein gene transcripts which correspond to conserved regions. Said conserved regions can be derived readily from sequence alignments, for example as shown in the figures. It is preferred to derive dsRNA sequences from the conserved regions of the consensus sequence which are shown in the figures.

A dsRNA can be synthesized chemically or enzymatically. To this end, it is possible to use cellular RNA polymerases or bacteriophage RNA polymerases (such as, for example, T3, T7 or SP6 RNA polymerase). Suitable methods for the in vitro expression of RNA are described (WO 97/32016; U.S. Pat. No. 5,593,874; U.S. Pat. No. 5,698,425, U.S. Pat. No. 5,712,135, U.S. Pat. No. 5,789,214, U.S. Pat. No. 5,804,693). A dsRNA which has been synthetized chemically or enzymatically in vitro can be purified from the reaction mixture fully or in part, for example by extraction, precipitation, electrophoresis, chromatography or combinations of these methods, before it is introduced into a cell, tissue or organism. The dsRNA can be introduced into the cell directly or else applied extracellularly (for example into the interstitial space).

However, it is preferred to transform the plant stably with an expression construct which realizes the expression of the dsRNA. Suitable methods are described hereinbelow.

b) Introduction of a Stomatin STM1 Protein Antisense Nucleic Acid Sequence

Methods of suppressing a certain polypeptide by preventing the accumulation of its mRNA by means of the "antisense" technology have been described many times, including in plants (Sheehy et al. (1988) Proc Natl Acad Sci USA 85: 8805-8809; U.S. Pat. No. 4,801,340; Mol J N et al. (1990) FEBS Lett 268(2):427-430). The antisense nucleic acid molecule hybridizes with, or binds to, the cellular mRNA and/or genomic DNA coding for the callose synthase target polypeptide to be suppressed. The transcription and/or translation of the target polypeptide is thereby suppressed. The hybridization can be accomplished in a traditional manner via the formation of a stable duplex or, in the case of genomic DNA, by binding the antisense nucleic acid molecule to the duplex of the genomic DNA as the result of specific interaction in the large groove of the DNA helix.

An antisense nucleic acid molecule suitable for reducing a stomatin STM1 polypeptide can be derived using the nucleic acid sequence which codes for this polypeptide, for example the nucleic acid molecule according to the invention as shown in SEQ ID No: or or a nucleic acid molecule coding for a functional equivalent thereof following Watson's and Crick's base-pairing rules. The antisense nucleic acid molecule can be complementary to all of the transcribed mRNA of the said polypeptide, be limited to the coding region or else only consist of an oligonucleotide which is complementary to part of the coding or noncoding sequence of the mRNA. Thus, for example, the oligonucleotide can be complementary to the region which comprises the translation start for said polypeptide. Antisense nucleic acid molecules can have a length of, for example, 20, 25, 30, 35, 40, 45 or 50 nucleotides, but they may also be longer and comprise 100, 200, 500, 1000, 2000 or 5000 nucleotides. Antisense nucleic acid molecules can be expressed recombinantly or synthesized chemically or enzymatically, using methods known to the skilled worker. In the case of chemical synthesis, natural or modified nucleotides can be used. Modified nucleotides can impart an increased biochemical stability to the antisense nucleic acid molecule and lead to an increased physical stability of the duplex formed of antisense nucleic acid sequence and sense target sequence. Examples which can be used are phosphoro-thioate derivatives and acridine-substituted nucleotides such as 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, β-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylamino-methyluracil, 5-methoxyaminomethyl-2-thiouracil, β-D-mannosylqueosine, 5'-methoxycarboxymethyluracil, 5-methoxyuracil, 2-methylthio-N-6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid, 5-methyl-2-thiouracil, 3-(3-amino-3-N2-carboxypropyl)uracil and 2,6-diaminopurine.

In a further preferred embodiment, the expression of a stomatin STM1 polypeptide can be inhibited by nucleic acid molecules which are complementary to a conserved region (for example a region which has been conserved as described above) or to a regulatory region of a stomatin STM1 protein gene (for example a stomatin STM1 protein promoter and/or enhancer) and which form triple-helical structures with the DNA double helix therein, so that the transcription of the stomatin STM1 protein gene is reduced. Suitable methods have been described (Helene C (1991) Anticancer Drug Res 6(6):569-84; Helene C et al. (1992) Ann NY Acad Sci 660: 27-36; Maher L J (1992) Bioassays 14(12):807-815).

In a further embodiment, the antisense nucleic acid molecule can be an α-anomeric nucleic acid. Such α-anomeric nucleic acid molecules form specific double-stranded hybrids with complementary RNA in which—as opposed to the conventional β-nucleic acids—the two strands run in parallel with one another (Gautier C et al. (1987) Nucleic Acids Res 15:6625-6641). The antisense nucleic acid molecule can furthermore also comprise 2'-O-methylribonucleotides (Inoue et al. (1987) Nucleic Acids Res 15:6131-6148) or chimeric RNA-DNA analogs (Inoue et al. (1987) FEBS Lett 215:327-330).

c) Introduction of a Ribozyme which Specifically, for Example Catalytically, Cleaves the Ribonucleic Acid Molecules Coding for Stomatin STM1 Protein.

Catalytic RNA molecules or ribozymes can be adapted to any target RNA and cleave the phosphodiester backbone at specific positions, whereby the target RNA is functionally deactivated (Tanner N K (1999) FEMS Microbiol Rev 23(3): 257-275). As the result, the ribozyme is not modified itself, but is capable of cleaving further target RNA molecules in an analogous manner, whereby it obtains the characteristics of an enzyme.

In this manner, it is possible to use ribozymes (for example hammerhead ribozymes; Haselhoff and Gerlach (1988) Nature 334:585-591) in order to cleave the mRNA of an enzyme to be suppressed, for example callose synthases, and to prevent translation. Methods of expressing ribozymes for reducing certain polypeptides are described in (EP 0 291 533, EP 0 321 201, EP 0 360 257). A ribozyme expression has also been described in plant cells (Steinecke P et al. (1992) EMBO J. 11 (4):1525-1530; de Feyter R et al. (1996) Mol Gen Genet 250(3):329-338). Ribozymes can be identified from a library of various ribozymes via a selection process (Bartel D and Szostak J W (1993) Science 261:1411-1418). Preferably, the binding regions of the ribozyme hybridize with the conserved regions of the stomatin STM1 protein as described above.

d) Introduction of a Stomatin STM1 Protein Antisense Nucleic Acid Sequence in Combination with a Ribozyme.

The above-described antisense strategy can advantageously be coupled with a ribozyme method. The incorporation of ribozyme sequences into "antisense" RNAs imparts this enzyme-like, RNA-cleaving characteristic to precisely these antisense RNAs and thus increases their efficiency in the inactivation of the target RNA. The preparation and use of suitable ribozyme "antisense" RNA molecules is described, for example, in Haseloff et al. (1988) Nature 334: 585-591.

The ribozyme technology can increase the efficiency of an antisense strategy. Suitable target sequences and ribozymes can be determined for example as described in "Steinecke P, Ribozymes, Methods in Cell Biology 50, Galbraith et al. eds, Academic Press, Inc. (1995), p. 449-460", by calculating the secondary structure of ribozyme RNA and target RNA and by their interaction (Bayley C C et al. (1992) Plant Mol. Biol. 18(2):353-361; Lloyd A M and Davis R W et al. (1994) Mol Gen Genet 242(6):653-657). For example, it is possible to construct derivatives of the Tetrahymena L-19 IVS RNA which derivatives have complementary regions to the mRNA of the stomatin STM1 protein to be suppressed (see also U.S. Pat. No. 4,987,071 and U.S. Pat. No. 5,116,742).

e) Introduction of a Stomatin STM1 Protein Sense Nucleic Acid Sequence for Inducing a Cosuppression The expression of a stomatin STM1 protein nucleic acid sequence in sense orientation can lead to a cosuppression of the corresponding homologous, endogenous gene. The expression of sense RNA with homology to an endogenous gene can reduce or cancel the expression of the former, similar to what has been described for antisense approaches (Jorgensen et al. (1996) Plant Mol Biol 31(5):957-973; Goring et al. (1991) Proc Natl Acad Sci USA 88:1770-1774; Smith et al. (1990) Mol Gen Genet 224:447-481; Napoli et al. (1990) Plant Cell 2:279-289; Van der Krol et al. (1990) Plant Cell 2:291-99). Here, the construct introduced can represent the homologous gene to be reduced either fully or only in part. The possibility of translation is not required. The application of this technology to plants is described for example in Napoli et al. (1990) The Plant Cell 2: 279-289 and in U.S. Pat. No. 5,034,323.

The cosuppression is preferably realized using a sequence which is essentially identical to at least part of the nucleic acid sequence coding for a stomatin STM1 protein or a functional equivalent thereof, for example of the nucleic acid molecule according to the invention, for example of the nucleic acid sequence as shown in SEQ ID No: or 13, or of the nucleic acid sequence coding for a functional equivalent thereof.

f) Introduction of Nucleic Acid Sequences Coding for a Dominant-Negative Stomatin STM1 Protein.

The activity of a stomatin STM1 protein can probably also be realized by expression of a dominant-negative variant of this stomatin STM1 protein. Methods of reducing the function or activity of a polypeptide by means of coexpression of its dominant-negative form are known to the skilled worker (Lagna G and Hemmati-Brivanlou A (1998) Current Topics in Developmental Biology 36:75-98; Perlmutter R M und Alberola-IIa J (1996) Current Opinion in Immunology 8(2): 285-90; Sheppard D (1994) American Journal of Respiratory Cell & Molecular Biology. 11 (1):1-6; Herskowitz 1 (1987) Nature 329(6136):219-22).

A dominant-negative stomatin STM1 protein variant can be accomplished for example by altering amino acid residues which are part of the stomatin STM1 and, as the result of their mutation, the polypeptide loses its function. Amino acid residues which are preferably to be mutated are those which are conserved in the stomatin STM1 proteins of different organisms. Such conserved regions can be determined for example by means of computer-aided comparison ("alignment"). These mutations for obtaining a dominant-negative stomatin STM1 protein variant are preferably carried out at the level of the nucleic acid sequence coding for stomatin STM1 proteins. A suitable mutation can be realized for example by PCR-mediated in vitro mutagenesis using suitable oligonucleotide primers, by means of which the desired mutation is introduced. Methods which are known to the skilled worker are used for this purpose. For example, the "LA PCR in vitro Mutagenesis Kit" (Takara Shuzo, Kyoto) can be used for this purpose.

g) Introduction of Stomatin STM1 Protein Genes, RNAs or Polypeptide-Binding Factors.

A reduction of a stomatin STM1 protein gene expression is also possible using specific DNA-binding factors, for example using factors of the zinc finger transcription factor type. These factors attach to the genomic sequence of the endogenous target gene, preferably in the regulatory regions, and bring about a repression of the endogenous gene. The use of such a method makes possible the reduction of the expression of an endogenous stomatin STM1 protein gene without it being necessary to recombinantly manipulate the sequence of the latter. Suitable methods for the preparation of suitable factors are described (Dreier B et al. (2001) J Biol Chem 276(31):29466-78; Dreier B et al. (2000) J Mol Biol 303(4): 489-502; Beerli R R et al. (2000) Proc Natl Acad Sci USA 97 (4):1495-1500; Beerli R R et al. (2000) J Biol Chem 275(42): 32617-32627; Segal D J and Barbas C F 3rd. (2000) Curr Opin Chem Biol 4(1):34-39; Kang J S and Kim J S (2000) J Biol Chem 275(12):8742-8748; Beerli R R et al. (1998) Proc Natl Acad Sci USA 95(25):14628-14633; Kim J S et al. (1997) Proc Natl Acad Sci USA 94(8):3616-3620; Klug A (1999) J Mol Biol 293(2):215-218; Tsai S Y et al. (1998) Adv Drug Deliv Rev 30(1-3):23-31; Mapp A K et al. (2000) Proc Natl Acad Sci USA 97(8):3930-3935; Sharrocks A D et al. (1997) mnt J Biochem Cell Biol 29(12):1371-1387; Zhang L et al. (2000) J Biol Chem 275(43):33850-33860).

The selection of these factors can be accomplished using a suitable portion of a stomatin STM1 protein gene. This segment is preferably located in the region of the promoter region. However, for the purpose of suppressing a gene, it may also be located in the region of the coding exons or introns. The corresponding segments are obtainable for the skilled worker by means of database search from the gene library or, starting from a stomatin STM1 protein cDNA whose gene is not present in the gene library, by screening a genomic library for corresponding genomic clones. The methods required for this purpose are known to the skilled worker.

Furthermore, it is possible to introduce, into a cell, factors which themselves inhibit the stomatin STM1 protein target polypeptide. The polypeptide-binding factors can be, for example, aptamers (Famulok M and Mayer G (1999) Curr Top Microbiol Immunol 243:123-36) or antibodies or antibody fragments. The preparation of these factors is described and known to the skilled worker. For example, a cytoplasmic scFv antibody has been employed for modulating the activity of the phytochrome A protein in recombinantly modified tobacco plants (Owen M et al. (1992) Biotechnology (N Y) 10(7):790-794; Franken E et al. (1997) Curr Opin Biotechnol 8(4):411-416; Whitelam (1996) Trend Plant Sci 1:286-272).

Gene expression can also be suppresesd by customized, low-molecular-weight synthetic compounds, for example of the polyamide type (Dervan P B and Burli R W (1999) Current Opinion in Chemical Biology 3:688-693; Gottesfeld J M et al. (2000) Gene Expr 9(1-2):77-91). These oligomers consist of the units 3-(dimethylamino)propylamine, N-methyl-3-hydroxypyrrole, N-methylimidazole and N-methylpyrrole and can be adapted to each segment of double-stranded DNA in such a way that they bind into the major group in a sequence-specific fashion and block the expression of the gene sequences therein. Suitable methods are described (see, inter alia, Bremer R E et al. (2001) Bioorg Med. Chem. 9(8):2093-103; Ansari A Z et al. (2001) Chem. Biol. 8(6): 583-92; Gottesfeld J M et al. (2001) J Mol. Biol. 309(3):615-29; Wurtz N R et al. (2001) Org Lett 3(8):1201-3; Wang C C et al. (2001) Bioorg Med Chem 9(3):653-7; Urbach A R and Dervan P B (2001) Proc Natl Acad Sci USA 98(8):4343-8; Chiang S Y et al. (2000) J Biol. Chem. 275(32):24246-54).

h) Introduction of the Viral Nucleic Acid Molecules and Expression Constructs which Bring about the Degradation of Stomatin STM1 Protein RNA.

The stomatin STM1 protein expression can also be realized efficiently by induction of the specific stomatin STM1 protein RNA degradation by the plant with the aid of a viral expression system (Amplikon) (Angell, S M et al. (1999) Plant J. 20(3):357-362). These systems—also referred to as "VIGS" (viral-induced gene silencing)—introduce, by means of viral vectors, nucleic acid sequences with homology to the transcripts to be suppressed into the plant. Transcription is then cancelled, probably mediated by plant defence mechanisms against viruses. Suitable techniques and methods are described (Ratcliff F et al. (2001) Plant J 25(2):237-45; Fagard M and Vaucheret H (2000) Plant Mol Biol 43(2-3):285-93; Anandalakshmi R et al. (1998) Proc Natl Acad Sci USA 95(22):13079-84; Ruiz M T (1998) Plant Cell 10(6):937-46).

The methods of the dsRNAi, of cosuppression by means of sense RNA and of "VIGS" ("virus-induced gene silencing") are also referred to as "post-transcriptional gene silencing" (PTGS). PTGS methods are particularly advantageous because the demands for the homology between the endogenous gene to be suppressed and the recombinantly expressed sense or dsRNA nucleic acid sequence are less stringent than, for example, in a traditional antisense approach. Suitable homology criteria are mentioned in the description of the dsRNAI method and can generally be applied to PTGS methods or dominant-negative approaches. As the result of the high degree of homology between the stomatin STM1 proteins from maize, wheat, rice and barley, it can be concluded that this polypeptide is highly conserved in plants. Thus, it is probably also possible, using the stomatin STM1 protein nucleic acid molecules as they are described herein, in particular by means of the nucleic acid molecules which are derived from the consensus sequences, or else for example from the nucleic acid molecules from Arabidopsis, barley, maize or rice, also efficiently to suppress the expression of homologous stomatin STM1 polypeptides in other species without the isolation and structure elucidation of the stomatin STM1 protein homologs found in these species being compulsory. This substantially simplifies the labor required.

i) Introduction of a Nucleic Acid Construct Suitable for Inducing a Homologous Recombination on Genes Coding for Stomatin STM1 Proteins, for Example for the Generation of Knockout Mutants.

To generate a homologously-recombinant organism with reduced stomatin STM1 protein function, one uses for example a nucleic acid construct which comprises at least part of an endogenous stomatin STM1 protein gene which is modified by a deletion, addition or substitution of at least one nucleotide, for example in the conserved regions, in such a way that the functionality is reduced or entirely nullified.

For example, the primary, secondary, tertiary or quaternary structure can be disrupted, for example in such a manner that the binding ability, or regulatory ability, of the cytoplasmic protein domain or the integration of the protein into the membrane no longer exists or is disrupted, in particular reduced. Such a disruption can be accomplished for example by the mutation of one or more residues which are indicated in the consensus sequence as being conserved or highly conserved.

The modification can also relate to the regulatory elements (for example the promoter) of the gene, so that the coding sequence remains unaltered, but that expression (transcription and/or translation) does not take place and is reduced.

In the case of conventional homologous recombination, the modified region is flanked at its 5' and 3' terminus by further nucleic acid sequences which must be of sufficient length for making possible the recombination. As a rule, the length is in the range of from several hundred or more bases up to several kilobases (Thomas K R and Capecchi M R (1987) Cell 51:503; Strepp et al. (1998) Proc Natl Acad Sci USA 95(8):4368-4373). To carry out the homologous recombination, the host organism—for example a plant—is transformed with the recombination construct using the methods described hereinbelow, and clones which have undergone successful recombination are selected using for example a resistance to antibiotics or herbicides.

j) Introduction of Mutations into Endogenous Stomatin STM1 Protein Genes for Generating a Loss of Function (for Example Generation of Stop Codons, Reading-Frame Shifts and the Like)

Further suitable methods for reducing the stomatin STM1 protein function are the introduction of nonsense mutations into endogenous stomatin STM1 protein genes, for example by means of generation of knockout mutants with the aid of, for example, T-DNA mutagenesis (Koncz et al. (1992) Plant Mol Biol 20(5):963-976), ENU (N-ethyl-N-nitrosourea)-mutagenesis or homologous recombination (Hohn B and Puchta (1999) H Proc Natl Acad Sci USA 96:8321-8323.) or EMS mutagenesis (Birchler J A, Schwartz D. Biochem Genet 1979 December; 17(11-12):1173-80; Hoffmann G R. Mutat Res. 1980 January; 75(1):63-129). Point mutations can also be generated by means of DNA-RNA hybrid oligonucleotides, which are also known as "chimeraplasty" (Zhu et al. (2000) Nat Biotechnol 18(5):555-558, Cole-Strauss et al. (1999) Nucl Acids Res 27(5):1323-1330; Kmiec (1999) Gene therapy American Scientist 87(3):240-247).

The cell- or tissue-specific reduction in the activity of a stomatin STM1 can be effected for example by expressing a suitable construct, which, for example, an abovementioned nucleic acid molecule, for example the antisense RNA, dsRNA, RNAi, ribozymes, with a suitable tissue-specific promoter, for example a promoter as described herein as being specific for epidermis or mesophyll.

For the purposes of the present invention, "mutations" means the modification of the nucleic acid sequence of a gene variant in a plasmid or in the genome of an organism. Mutations can arise for example as the result of errors in the replication, or they can be caused by mutagens. While the spontaneous mutation rate in the cell genome of organisms is very low, the skilled worker is familiar with a multiplicity of biological, chemical or physical mutagens.

Mutations comprise substitutions, additions, deletions of one or more nucleic acid residues. Substitutions are understood as meaning the exchange of individual nucleic acid bases; one distinguishes between transitions (substitution of a purine base for a purine base, or of a pyrimidine base for a pyrimidine base) and transversions (substitution of a pyrimidine base for a purine base (or vice versa)).

Additions or insertions are understood as meaning the incorporation of additional nucleic acid residues into the DNA, it being possible to result in reading-frame shifts. In the case of such reading-frame shifts, one distinguishes between "in-frame" insertions/additions and "out-of-frame" insertions. In the case of the "in-frame" insertions/additions, the reading frame is retained, and a polypeptide which is enlarged by the number of the amino acids encoded by the inserted nucleic acids results. In the case of "out-of-frame" insertions/additions, the original reading frame is lost, and the formation of a complete and functional polypeptide is no longer possible.

Deletions describe the loss of one or more base pairs, which likewise lead to "in-frame" or "out-of-frame" reading-frame shifts and the consequences which this entails regarding the formation of an intact protein.

The mutagenic agents (mutagens) which can be used for generating random or site-specific mutations, and the methods and techniques which can be applied, are known to the skilled worker. Such methods and mutagens are described for example in A. M. van Harten [(1998), "Mutation breeding: theory and practical applications", Cambridge University Press, Cambridge, UK], E Friedberg, G Walker, W Siede [(1995), "DNA Repair and Mutagenesis", Blackwell Publishing], or K. Sankaranarayanan, J. M. Gentile, L. R. Ferguson [(2000) "Protocols in Mutagenesis", Elsevier Health Sciences].

Usual molecular-biological methods and processes, such as the in vitro mutagenesis kit, LA PCR in vitro Mutagenesis Kit (Takara Shuzo, Kyoto), or PCR mutageneses using suitable primers may be employed for introducing site-specific mutations.

As has already been mentioned above, a multiplicity of chemical, physical and biological mutagens exists.

Those mentioned hereinbelow are given by way of example, but not by limitation.

Chemical mutagens can be distinguished by their mechanism of action. Thus, there are base analogs (for example 5-bromouracil, 2-aminopurine), mono- and bifunctional alkylating agents (for example monofunctional agents such as ethylmethylsulfonate, dimethyl sulfate, or bifunctional agents such as dichloroethyl sulfite, mitomycin, nitrosoguanidine-dialkylnitrosamine, N-nitrosoguanidine derivatives) or intercalating substances (for example acridine, ethidium bromide).

Physical mutagens are, for example, ionizing radiation. Ionizing radiation is electromagnetic waves or particle radiation capable of ionizing molecules, i.e. of removing electrons from the latter. The remaining ions are highly reactive in most cases, so that, if they are generated in live tissue, are capable of causing great damage, for example to the DNA, and (at low intensity) thereby inducing mutations. Ionizing radiation is, for example, gamma-radiation (photo energy of approximately one megaelectron volt MeV), X-rays (photo energy of a plurality of or many kiloelectron volts keV) or else ultraviolet light (UV light, photon energy of above 3.1 eV). UV light causes the formation of dimers between bases; with thymidine dimers, which give rise to mutations, being the most frequent here.

The traditional generation of mutants by treating the seeds with mutagenic agents such as, for example, ethylmethylsulfonate (EMS) (Birchler J A, Schwartz D. Biochem Genet 1979 December; 17(11-12):1173-80; Hoffmann G R. Mutat Res. 1980 January; 75(1):63-129) or ionizing radiation has been joined by the use of biological mutagens, for example transposons (for example Tn5, Tn903, Tn916, Tn1000, Balcells et al., 1991, May B P et al. (2003) Proc Natl Acad Sci USA. September 30; 100(20):11541-6.) or molecular-biological methods such as the mutagenesis by means of T-DNA insertion (Feldman, K. A. Plant J. 1:71-82.1991, Koncz et al. (1992) Plant Mol Biol 20(5):963-976).

The use of chemical or biological mutagens is preferred for the generation of mutated gene variants. In the case of chemical agents, the generation of mutants by application of EMS (ethylmethylsulfonate) mutagenesis is mentioned by particular preference. In the case of the generation of mutants using biological mutagenesis, the T-DNA mutagenesis or transposon mutagenesis may be mentioned by preference.

Thus, it is also possible to employ those polypeptides for the method according to the invention which are obtained as the result of a mutation of a polypeptide according to the invention, for example as shown in SEQ ID No: 15, 16 or 17.

All substances and compounds which directly or indirectly bring about a reduction in the polypeptide quantity, RNA quantity, gene activity or polypeptide activity of a stomatin STM1 protein will hereinbelow be summarized under the term "anti-stomatin STM1 protein compounds". The term "anti-stomatin STM1 protein compound" explicitly includes the nucleic acid sequences, peptides, proteins or other factors which are employed in the above-described methods.

In a further preferred embodiment of the present invention, an increase in the resistance to pathogens from the families Blumeriaceae, Pucciniaceae, Mycosphaerellaceae and Hypocreaceae in a monocotyledonous or dicotyledonous plant or an organ, tissue or a cell thereof, is obtained by:
a) introduction, into a plant cell, of a recombinant expression cassette comprising an "anti-stomatin STM1 protein compound" in operable linkage with a promoter which is active in plants;
b) regeneration of the plant from the plant cell; and
c) expression of said "anti-stomatin STM1 protein compound" in a sufficient quantity and over a sufficiently long period to generate, or to increase, a pathogen resistance in said plant.

For example, regarding a nucleic acid sequence, an expression cassette or a vector comprising said nucleic acid sequence or an organism transformed with said nucleic acid sequence, expression cassette or vector, "transgenic" means all those constructs or organisms which are the result of recombinant methods and in which either
a) the stomatin STM1 protein nucleic acid sequence, or
b) a genetic control sequence which is operably linked with the stomatin STM1 protein nucleic acid sequence, for example a promoter, or
c) (a) and (b)
are not in their natural genetic environment or have been modified by recombinant methods, it being possible for the modification to be for example a substitution, addition, deletion or insertion of one or more nucleotide residues. Natural genetic environment means the natural chromosomal locus in the original organism, or else the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, very especially preferably at least 5000 bp. A naturally occurring expression cassette—for example the naturally occurring combination of the stomatin STM1 protein promoter with the corresponding stomatin STM1 protein gene—becomes a transgenic expression cassette when the latter is modified by non-natural, synthetic ("artificial") methods, such as, for example, treatment with a mutagen. Suitable methods are described (U.S. Pat. No. 5,565,350; WO 00/15815).

For the purposes of the invention, "introduction" comprises all those methods which are suitable for introducing an "anti-stomatin STM1 protein compound" directly or indirectly into a plant or into a cell, compartment, tissue, organ or seeds thereof, or for generating such a compound therein. It comprises direct and indirect methods. The introduction can lead to a transient presence of one "anti-stomatin STM1 protein compound" (for example of a dsRNA) or else to a stable presence.

As the result of the differing nature of the above-described approaches, the "anti-stomatin STM1 protein compound" can exert its function directly (for example by insertion into an endogenous stomatin STM1 protein gene). However, the function can also be exerted indirectly after transcription into an RNA (for example in the case of antisense approaches) or after transcription and translation into a protein (for example in the case of binding factors). Both direct and indirectly acting "anti callose synthase compounds" are comprised in accordance with the invention.

"Introduction" comprises for example methods such as transfection, transduction or transformation.

Thus, "anti-stomatin STM1 compound" also comprises for example recombinant expression constructs which bring about an expression (i.e. transcription and, if appropriate, translation) of, for example, a stomatin STM1 protein dsRNA or a stomatin STM1 protein "antisense" RNA, preferably in a plant or in a part, tissue, organ or seed thereof.

In said expression constructs/expression cassettes, a nucleic acid molecule whose expression (transcription and, if appropriate, translation) generates an "anti-stomatin STM1 protein compound" is preferably in operable linkage with at least one genetic control element (for example a promoter) which ensures an expression in plants. If the expression construct is to be introduced directly into the plant and the "anti-stomatin STM1 protein compound" (for example the stomatin STM1 protein dsRNA) is to be generated therein in planta, plant-specific genetic control elements (for example promoters) are preferred. However, the "anti-stomatin STM1 protein compound" can also be generated in other organisms or in vitro and then be introduced into the plant. Here, all procaryotic or eucaryotic genetic control elements (for example promoters) which permit the expression in the respective plant which has been chosen for the generation are preferred.

An "operable" linkage is understood as meaning for example the sequential arrangement of a promoter with the nucleic acid sequence to be expressed (for example an "anti-stomatin STM1 protein compound") and, if appropriate, further regulatory elements such as, for example, a terminator in such a way that each of the regulatory elements is capable of fulfilling its function in the transgenic expression of the nucleic acid sequence, depending on the arrangement of the nucleic acid sequences to sense or antisense RNA. A direct linkage in the chemical sense is not necessarily required for this purpose. Genetic control sequences such as, for example, enhancer sequences, can also exert their function on the target sequence from positions which are further removed or else from other DNA molecules. Preferred arrangements are those in which the nucleic acid sequence to be expressed recombinantly is positioned behind the sequence which acts as promoter, so that the two sequences are bonded covalently with one another. In this context, the distance between the promoter sequence and nucleic acid sequence to be expressed recombinantly is preferably less than 200 base pairs, especially preferably less than 100 base pairs, very especially preferably less than 50 base pairs.

The preparation of a functional linkage and the preparation of an expression cassette can be accomplished by means of customary recombination and cloning techniques as are described for example in Maniatis T, Fritsch E F and Sambrook J (1989) Molecular Cloning: A Laboratory Manual, Cold Spring Harbor Laboratory, Cold Spring Harbor (NY), in Silhavy T J, Berman M L and Enquist L W (1984) Experiments with Gene Fusions, Cold Spring Harbor Laboratory, Cold Spring Harbor (NY), in Ausubel F M et al. (1987) Current Protocols in Molecular Biology, Greene Publishing Assoc. and Wiley Interscience and in Gelvin et al. (1990) in: Plant Molecular Biology Manual. However, it is also possible to position further sequences which, for example, act as a linker with specific restriction enzyme cleavage sites or as a signal peptide between the two sequences. Moreover, the insertion of sequences can lead to the expression of fusion proteins. Preferably, the expression cassette consisting of a linkage of promoter and nucleic acid sequence to be expressed can be present in vector-integrated form and can be inserted into a plant genome by, for example, transformation.

However an expression cassette is also understood as meaning those constructs in which a promoter is placed behind an endogenous stomatin STM1 protein gene, for example by means of a homologous recombination, and where the expression of an antisense stomatin STM1 protein RNA brings about the reduction according to the invention of a stomatin STM1 protein. Analogously, an "anti-stomatin STM1 protein compound" (for example a nucleic acid sequence coding for a stomatin STM1 protein dsRNA or a stomatin STM1 protein antisense RNA) can be placed behind an endogenous promoter in such a way that the same effect occurs. Both approaches result in expression cassettes for the purposes of the invention.

Plant-specific promoters means in principle any promoter which is capable of controlling the expression of genes, in particular foreign genes, in plants or plant parts, plant cells, plant tissues, plant cultures. Here, the expression can be for example constitutional, inducible or development-dependent.

The following are preferred:
a) Constitutive Promoters

Preferred vectors are those which make possible a constitutive expression in plants (Benfey et al. (1989) EMBO J. 8:2195-2202). "Constitutive" promoter means those promoters which ensure expression in numerous, preferably all, tissues over a relatively large period of plant development, preferably at all times during plant development. In particular, a plant promoter or a promoter derived from a plant virus is preferably used. The promoter of the 35S transcript of the CaMV cauliflower mosaic virus (Franck et al. (1980) Cell 21:285-294; Odell et al. (1985) Nature 313:810-812; Shewmaker et al. (1985) Virology 140:281-288; Gardner et al. (1986) Plant Mol Biol 6:221-228) or the 19S CaMV Promoter (U.S. Pat. No. 5,352,605; WO 84/02913; Benfey et al. (1989) EMBO J. 8:2195-2202) is particularly preferred. A further suitable constitutive promoter is the rubisco small subunit (SSU) promoter (U.S. Pat. No. 4,962,028), the promoter of *agrobacterium* nopaline synthase, the TR double promoter, the *agrobacterium* OCS (octopine synthase) promoter, the ubiquitin promoter (Holtorf S et al. (1995) Plant Mol Biol 29:637-649), the ubiquitin 1 promoter (Christensen et al. (1992) Plant Mol Biol 18:675-689; Bruce et al. (1989) Proc Natl Acad Sci USA 86:9692-9696), the Smas promoter, the cinnamyl-alcohol dehydrogenase promoter (U.S. Pat. No. 5,683,439), the promoters of vacuolar ATPase subunits or the promoter of a proline-rich protein from wheat (WO 91/13991), and further promoters of genes whose constitutive expression in plants is known to the skilled worker. Especially preferred as constitutive promoter is the promoter of nitrilase-1 (nit1) gene from *A. thaliana* (GenBank Acc.-No.: Y07648.2, Nukleotide 2456-4340, Hillebrand et al. (1996) Gene 170:197-200).

b) Tissue-specific Promoters

One embodiment employs promoters with specificities for the anthers, ovaries, flowers, leaves, stems, roots and seeds.

Seed-specific promoters such as, for example, the promoter of phaseolin (U.S. Pat. No. 5,504,200; Bustos M M et al. (1989) Plant Cell 1(9):839-53), of the 2S albumin gene (Joseffson L G et al. (1987) J Biol Chem 262:12196-12201), of legumin (Shirsat A et al. (1989) Mol Gen Genet 215(2): 326-331), of the USP (unknown seed protein; Bäumlein H et al. (1991) Mol Gen Genet 225(3):459-67), of the napin gene (U.S. Pat. No. 5,608,152; Stalberg K et al. (1996) L Planta 199:515-519), of sucrose binding protein (WO 00/26388) or the legumin B4 promoter (LeB4; Bäumlein H et al. (1991) Mol Gen Genet 225: 121-128; Baeumlein et al. (1992) Plant Journal 2(2):233-9; Fiedler U et al. (1995) Biotechnology (NY) 13(10):1090f), the oleosin promoter from *arabidopsis* (WO 98/45461), the Bce4 promoter from *Brassica* (WO 91/13980). Further suitable seed-specific promoters are those of the genes coding for the high molecular weight glutenin (HMWG), gliadin, branching enzyme, ADP glucose pyrophosphatase (AGPase) or starch synthase. Further preferred promoters are those allowing seed-specific expression in monocotyledons such as maize, barley, wheat, rye, rice etc. It is possible and advantageous to employ the promoter of the lpt2 or lpt1 gene (WO 95/15389, WO 95/23230) or the promoters described in WO 99/16890 (promoters of the hordein gene, of the glutelin gene, of the oryzin gene, of the prolamin gene, of the gliadin gene, of the zein gene, of the kasirin gene or of the secalin gene).

Tuber-, storage root- or root-specific promoters, for example the patatin class I promoter (B33) or the promoter of the potato cathepsin D inhibitor.

Leaf-specific promoters, for example for example the promoter of the cytosolic FBPase from potato (WO 97/05900), the SSU promoter (small subunit) of the rubisco (ribulose-1, 5-bisphosphate carboxylase) or the ST-LSI promoter from potato (Stockhaus et al. (1989) EMBO J. 8:2445-2451). Epidermis-specific promoters, for example the promoter of the OXLP gene ("oxalate oxidase like protein"; Wei et al. (1998) Plant Mol. Biol. 36:101-112).

Examples of Other Tissue-Specific Promoters are:

Flower-specific Promoters for example the phytoen synthase promoter (WO 92/16635) or the promoter of the P-rr gene (WO 98/22593).

Anther-specific Promoters for example the 5126 promoter (U.S. Pat. Nos. 5,689,049, 5,689,051), the glob-I promoter and the γ-zein promoter. or the abovementioned epidermis- or mesophyll-specific promoters which are especially preferred.

In one embodiment, the activity of STM1, in particular of HvSTM1, in particular of the STM1 as described herein, is lowered, blocked or prevented in the epidermis, in particular for increasing the resistance to mildew, for example by means of gene silencing, for example by means of an RNAi, antisense, cosuppression or microRNA approach as can be carried out by the skilled worker on the basis of the methods and sequences disclosed herein.

In one embodiment, the activity of STM1, in particular of HvSTM1, in particular of STM1 as described herein, is lowered, blocked or prevented in the mesophyll, in particular for increasing the resistance to *Septoria* and rusts, for example by means of gene silencing, for example by means of an RNAi, antisense, cosuppression or microRNA approach as can be carried out by the skilled worker on the basis of the methods and sequences disclosed herein.

c) Chemically Inducible Promoters

The expression cassettes may also comprise a chemically inducible promoter (review article: Gatz et al. (1997) Annu. Rev. Plant Physiol Plant Mol Biol 48:89-108) through which expression of the exogenous gene in the plant can be controlled at a particular point in time. Promoters of this type, such as, for example, the PRP1 promoter (Ward et al. (1993) Plant Mol Biol 22:361-366), a salicylic acid-inducible promoter (WO 95/19443), a benzenesulfonamide-inducible promoter (EP 0 388 186), a tetracycline-inducible promoter (Gatz et al. (1992) Plant J 2:397-404), an abscisic acid-inducible promoter (EP 0 335 528) and an ethanol- or cyclohexanone-inducible promoter (WO 93/21334) can likewise be used. Thus, for example, the expression of a molecule which reduces or inhibits the stomatin STM1 protein function, such as, for example, the dsRNA, ribozymes, antisense nucleic acid molecules and the like which have been listed above can be induced at suitable points in time.

d) Stress- or Pathogen-inducible Promoters

Very especially advantageous is the use of inducible promoters for expressing the RNAi constructs employed for reducing the callose synthase polypeptide quantity, activity or function, which, for example, when pathogen-inducible promoters are used, makes possible an expression only when required, i.e. in the case of attack by pathogens).

In one embodiment, the method according to the invention therefore uses promoters which are active in plants which are pathogen-inducible promoters.

Pathogen-inducible promoters comprise the promoters of genes which are induced as a result of pathogen attack, such as, for example, genes of PR proteins, SAR proteins, β-1,3-glucanase, chitinase etc. (for example Redolfi et al. (1983) Neth J Plant Pathol 89:245-254; Uknes, et al. (1992) Plant Cell 4:645-656; Van Loon (1985) Plant Mol Viral 4:111-116; Marineau et al. (1987) Plant Mol Biol 9:335-342; Matton et al. (1987) Molecular Plant-Microbe Interactions 2:325-342; Somssich et al. (1986) Proc Natl Acad Sci USA 83:2427-2430; Somssich et al. (1988) Mol Gen Genetics 2:93-98; Chen et al. (1996) Plant J 10:955-966; Zhang and Sing (1994) Proc Natl Acad Sci USA 91:2507-2511; Warner, et al. (1993) Plant J 3:191-201; Siebertz et al. (1989) Plant Cell 1:961-968) (1989).

Also comprised are wound-inducible promoters such as that of the pinII gene (Ryan (1990) Ann Rev Phytopath 28:425-449; Duan et al. (1996) Nat Biotech 14:494-498), of the wun1 and wun2 gene (U.S. Pat. No. 5,428,148), of the win1 and win2 gene (Stanford et al. (1989) Mol Gen Genet 215:200-208), of the systemin gene (McGurl et al. (1992) Science 225:1570-1573), of the WIP1 gene (Rohmeier et al. (1993) Plant Mol Biol 22:783-792; Eckelkamp et al. (1993)

FEBS Letters 323:73-76), of the MPI gene (Corderok et al. (1994) Plant J 6(2):141-150) and the like.

A source of further pathogen-inducible promoters is the PR gene family. A series of elements in these promoters have proved advantageous. Thus, the region −364 to −288 in the promoter of PR-2d mediates salicylate specificity (Buchel et al. (1996) Plant Mol Biol 30, 493-504). The sequence 5'-TCATCTTCTT-3' (SEQ ID NO: 20) occurs repeatedly in the promoter of the barley β-1,3-glucanase and in more than 30 other stress-induced genes. In tobacco, this region binds a nuclear protein whose abundance is increased by salicylate. The PR-1 promoters from tobacco and *Arabidopsis* (EP-A 0 332 104, WO 98/03536) are also suitable as pathogen-inducible promoters. Preferred, since particularly specifically induced by pathogens, are the "acidic PR-5"-(aPR5) promoters from barley (Schweizer et al. (1997) Plant Physiol 114: 79-88) and wheat (Rebmann et al. (1991) Plant Mol Biol 16:329-331). aPR5 proteins accumulate within approximately 4 to 6 hours after attack by pathogens and only show very little background expression (WO 99/66057). One approach for obtaining an increased pathogen-induced specificity is the generation of synthetic promoters from combinations of known pathogen-responsive elements (Rushton et al. (2002) Plant Cell 14, 749-762; WO 00/01830; WO 99/66057). Other pathogen-inducible promoters from different species are known to the skilled worker (EP-A 1 165 794; EP-A 1 062 356; EP-A 1 041 148; EP-A 1 032 684).

Further pathogen-inducible promoters comprise the Flachs Fis1 promoter (WO 96/34949), the Vst1 promoter (Schubert et al. (1997) Plant Mol Biol 34:417-426) and the tobacco EAS4 sesquiterpene cyclase promoter (U.S. Pat. No. 6,100, 451).

Other preferred promoters are those which are induced by biotic or abiotic stress, such as, for example, the pathogen-inducible promoter of the PRP1 gene (or gst1 promoter), for example from potato (WO 96/28561; Ward et al. (1993) Plant Mol Biol 22:361-366), the heat-inducible hsp70 or hsp80 promoter from tomato (U.S. Pat. No. 5,187,267), the chill-inducible alpha-amylase promoter from potato (WO 96/12814), the light-inducible PPDK promoter or the wounding-inducible pinII promoter (EP-A 0 375 091).

e) Mesophyll-tissue-specific Promoters

In one embodiment, the method according to the invention employs mesophyll-tissue-specific promoters such as, for example, the promoter of the wheat germin 9f-3.8 gene (Gen-Bank Acc.-No.: M63224) or the barley GerA promoter (WO 02/057412). Said promoters are particularly advantageous since they are both mesophyll-tissue-specific and pathogen-inducible. Also suitable is the mesophyll-tissue-specific *Arabidopsis* CAB-2 promoter (GenBank Acc.-No.: X15222), and the *Zea mays* PPCZm1 promoter (GenBank Acc.-No.: X63869) or homologs thereof. Mesophyll-tissue-specific means that the transcription of a gene is limited to as few as possible plant tissues which comprise the mesophyll tissue as the result of the specific interaction of cis elements present in the promoter sequence and transcription factors binding to these elements; preferably, it means a transcription which is limited to the mesophyll tissue.

As regards further promoters which are expressed essentially in the mesophyll or in the epidermis, see the enumeration inserted further above.

f) Development-dependent Promoters

Examples of further suitable promoters are fruit ripening-specific promoters such as, for example, the fruit ripening-specific promoter from tomato (WO 94/21794, EP 409 625). Development-dependent promoters include some of the tissue-specific promoters because the development of individual tissues naturally takes place in a development-dependent manner.

Constitutive, and leaf- and/or stem-specific, pathogen-inducible, root-specific, mesophyll-tissue-specific promoters are particularly preferred, with constitutive, pathogen-inducible, mesophyll-tissue-specific and root-specific promoters being most preferred.

A further possibility is for further promoters which make expression possible in further plant tissues or in other organisms such as, for example, *E. coli* bacteria to be operably linked to the nucleic acid sequence to be expressed. All the promoters described above are in principle suitable as plant promoters.

Other promoters which are suitable for expression in plants are described (Rogers et al. (1987) Meth in Enzymol 153: 253-277; Schardl et al. (1987) Gene 61:1-11; Berger et al. (1989) Proc Natl Acad Sci USA 86:8402-8406).

The nucleic acid sequences present in the expression cassettes or vectors of the invention may be operably linked to further genetic control sequences besides a promoter. The term genetic control sequences has a wide meaning and means all sequences which have an influence on the coming into existence or the function of the expression cassette of the invention. For example, genetic control sequences modify transcription and translation in prokaryotic or eukaryotic organisms. The expression cassettes of the invention preferably comprise a promoter with an above-mentioned specificity 5'-upstream from the particular nucleic acid sequence which is to be expressed transgenically, and a terminator sequence as additional genetic control sequence 3'-downstream, and if appropriate further conventional regulatory elements, in each case operably linked to the nucleic acid sequence to be expressed transgenically.

Genetic control sequences also comprise further promoters, promoter elements or minimal promoters capable of modifying the expression-controlling properties. It is thus possible for example through genetic control sequences for tissue-specific expression to take place additionally dependent on particular stress factors. Corresponding elements are described for example for water stress, abscisic acid (Lam E and Chua N H, J Biol Chem 1991; 266(26): 17131-17135) and heat stress (Schoffl F et al., Molecular & General Genetics 217(2-3):246-53, 1989).

It is possible in principle for all natural promoters with their regulatory sequences like those mentioned above to be used for the method of the invention. It is additionally possible also for synthetic promoters to be used advantageously.

Genetic control sequences further comprise also the 5'-untranslated regions, introns or noncoding 3' region of genes such as, for example, the actin-1 intron, or the Adh1-S introns 1, 2 and 6 (generally: The Maize Handbook, Chapter 116, Freeling and Walbot, Eds., Springer, N.Y. (1994)). It has been shown that these may play a significant function in the regulation of gene expression. It has thus been shown that 5'-untranslated sequences are capable of enhancing transient expression of heterologous genes. An example of a translation enhancer which may be mentioned is the 5' leader sequence from the tobacco mosaic virus (Gallie et al. (1987) Nucl Acids Res 15:8693-8711) and the like. They may in addition promote tissue specificity (Rouster J et al. (1998) Plant J 15:435-440).

The expression cassette may advantageously comprise one or more so-called enhancer sequences in operable linkage with the promoter, which make increased transgenic expression of the nucleic acid sequence possible. Additional advantageous sequences such as further regulatory elements or terminators can also be inserted at the 3' end of the nucleic acid sequences to be expressed recombinantly. The nucleic acid sequences to be expressed recombinantly may be present in one or more copies in the gene construct.

Polyadenylation signals suitable as control sequences are plant polyadenylation signals, preferably those which correspond essentially to T-DNA polyadenylation signals from *Agrobacterium tumefaciens*, in particular to gene 3 of the T-DNA (octopine synthase) of the Ti plasmid pTiACHS (Gielen et al. (1984) EMBO J. 3:835 ff) or functional equivalents thereof. Examples of particularly suitable terminator sequences are the OCS (octopine synthase) terminator and the NOS (nopaline synthase) terminator.

Control sequences additionally mean those which make homologous recombination or insertion into the genome of a host organism possible or allow deletion from the genome. In homologous recombination, for example, the natural promoter of a particular gene can be specifically replaced by a promoter with specificity for the embryonal epidermis and/or the flower.

An expression cassette and/or the vectors derived from it may comprise further functional elements. The term functional element has a wide meaning and means all elements which have an influence on the production, replication or function of the expression cassettes, the vectors or the transgenic organisms of the invention. Non-restrictive examples which may be mentioned are:

a) Selection markers which confer a resistance to a metabolism inhibitor such as 2-deoxyglucose 6-phosphate (WO 98/45456), antibiotics or biozides, preferably herbicides, for example kanamycin, G 418, bleomycin, hygromycin or phosphinotricin and the like. Especially preferred selection markers are those which confer a resistance to herbicides. DNA sequences which code for phosphinothricin acetyltransferases (PAT), which inactivate glutamine synthase inhibitors (bar and pat gene), 5-enolpyruvylshikimate-3-phosphate synthase (EPSP synthase genes) which confer resistance to Glyphosat® (N-(phosphonomethyl)glycine), the gox gene, which codes for the Glyphosat®-degrading enzyme (glyphosate oxidoreductase), the deh gene (coding for a dehalogenase which inactivates dalapon), sulfonylurea- and imidazolinone-inactivating acetolactate synthases and bxn genes which code for bromoxynil-degrading nitrilase enzymes, the aasa gene, which confers a resistance to the antibiotic apectinomycin, the streptomycin phosphotransferase (SPT) gene, which makes possible a resistance to streptomycin, the neomycin phosphotransferase (NPTII) gene, which confers a resistance to kanamycin or geneticidin, the hygromycin phosphotransferase (HPT) gene, which mediates a resistance to hygromycin, the acetolactate synthase gene (ALS), which mediates a resistance to sulfonylurea herbicides (for example mutated ALS variants with, for example, the S4 and/or Hra mutation).

b) Reporter genes which code for easily quantifiable proteins and ensure via an intrinsic color or enzymic activity an assessment of the transformation efficiency or of the location or timing of expression. Very particular preference is given in this connection to reporter proteins (Schenborn E, Groskreutz D. Mol. Biotechnol. 1999; 13(1):29-44) such as the green fluorescence protein (GFP) (Sheen et al. (1995) Plant Journal 8(5):777-784; Haselhoff et al. (1997) Proc Natl Acad Sci USA 94(6):2122-2127; Reichel et al. (1996) Proc Natl Acad Sci USA 93(12):5888-5893; Tian et al. (1997) Plant Cell Rep 16:267-271; WO 97/41228; Chui W L et al. (1996) Curr Biol 6:325-330; Leffel S M et al. (1997) Biotechniques. 23(5):912-8), the chloramphenicol-transferase, a luciferase (Ow et al. (1986) Science 234:856-859; Millar et al. (1992) Plant Mol Biol Rep 10:324-414), the aequorin gene (Prasher et al. (1985) Biochem Biophys Res Commun 126(3):1259-1268), the β-galactosidase, R-locus gene (code for a protein which regulates the production of anthocyanin pigments (red coloration) in plant tissue and thus makes possible the direct analysis of the promoter activity without the addition of additional adjuvants or chromogenic substrates; Dellaporta et al., In: Chromosome Structure and Function: Impact of New Concepts, 18th Stadler Genetics Symposium, 11:263-282, (1988), with β-glucuronidase being very especially preferred (Jefferson et al., EMBO J. 1987, 6, 3901-3907).

c) Origins of replication which ensure replication of the expression cassettes or vectors of the invention in, for example, *E. coli*. Examples which may be mentioned are ORI (origin of DNA replication), the pBR322 ori or the P15A ori (Sambrook et al.: Molecular Cloning. A Laboratory Manual, $2^{nd}$ ed. Cold Spring Harbor Laboratory Press, Cold Spring Harbor, N.Y., 1989).

d) Elements which are necessary for *agrobacterium*-mediated plant transformation, such as, for example, the right or left border of the T-DNA or the vir region.

To select successfully transformed cells, it is generally required additionally to introduce a selectable marker which confers to the successfully transformed cells a resistance to a biocide (for example a herbicide), a metabolism inhibitor such as 2-deoxyglucose 6-phosphate (WO 98/45456) or an antibiotic. The selection marker permits the selection of the transformed cells from untransformed cells (McCormick et al. (1986) Plant Cell Reports 5:81-84).

The introduction of an expression cassette according to the invention into an organism or into cells, tissues, organs, parts or seeds thereof (preferably into plants or plant cells, tissues, organs, parts or seeds) can advantageously be accomplished using vectors in which the expression cassettes are present. The expression cassette can be introduced into the vector (for example a plasmid) via a suitable restriction cleavage site. The resulting plasmid is first introduced into *E. coli*. Correctly transformed *E. coli* are selected, cultured, and the recombinant plasmid is obtained using methods known to the skilled worker. Restriction analysis and sequencing can be used for verifying the cloning step.

Examples of vectors can be plasmids, cosmids, phages, viruses or else *agrobacteria*. In an advantageous embodiment, the introduction of the expression cassette is accomplished by means of plasmid vectors. Preferred vectors are those which make possible a stable integration of the expression cassette into the host genome.

The generation of a transformed organism (or a transformed cell) requires the introduction of suitable DNA molecules, and thus of the RNA molecules or proteins formed as the result of their gene expression, into the host cell in question.

A multiplicity of methods (Keown et al. (1990) Methods in Enzymology 185:527-537) is available for this procedure, which is referred to as transformation (or transduction or transfection). Thus, DNA or RNA can be introduced for example directly by means of microinjection or by bombardment with DNA-coated microparticles. Also, it is possible to permeabilize the cell chemically, for example with polyethylene glycol, so that the DNA can enter the cell by diffusion. Alternatively, the DNA can be introduced by protoplast fusion with other DNA-comprising units such as minicells, cells, lysosomes or liposomes. Another suitable method for introducing DNA is electroporation, where the cells are reversibly permeabilized by means of an electrical pulse.

Suitable methods are described (for example in Bilang et al. (1991) Gene 100:247-250; Scheid et al. (1991) Mol Gen Genet 228:104-112; Guerche et al. (1987) Plant Science 52:111-116; Neuhause et al. (1987) Theor Appl Genet 75:30-36; Klein et al. (1987) Nature 327:70-73; Howell et al. (1980) Science 208:1265; Horsch et al. (1985) Science 227:1229-1231; DeBlock et al. (1989) Plant Physiology 91:694-701; Methods for Plant Molecular Biology (Weissbach and Weissbach, eds.) Academic Press Inc. (1988); and Methods in Plant Molecular Biology (Schuler and Zielinski, eds.) Academic Press Inc. (1989)).

In plants, the described methods for the transformation and regeneration of plants from plant tissues or plant cells for the transient or stable transformation are used. Suitable methods are mainly the transformation of protoplasts by means of polyethylene-glycol-induced DNA uptake, the biolistic method with the gene gun, the so-called particle bombardment method, electroporation, the incubation of dry embryos in DNA-comprising solution, and Microinjection.

In addition to these "direct" transformation techniques, a transformation can also be carried out by bacterial infection by means of *Agrobacterium tumefaciens* or *Agrobacterium rhizogenes*. The methods are described for example in Horsch R B et al. (1985) Science 225: 1229f).

If *agrobacteria* are used, the expression cassette is to be integrated into specific plasmids, either into a shuttle or intermediate vector or into a binary vector. If a Ti or Ri plasmid is used for the transformation, at least the right border, but in most cases the right and the left border, of the Ti or Ri plasmid T-DNA is linked as flanking region with the expression cassette to be introduced.

It is preferred to use binary vectors. Binary vectors are capable of replicating both in *E. coli* and in *Agrobacterium*. As a rule, they comprise a selection marker gene and a linker or polylinker flanked by the right and left T-DNA border sequence. They can be transformed directly into *Agrobacterium* (Holsters et al. (1978) Mol Gen Genet 163:181-187). The selection marker gene permits a selection of transformed *agrobacteria* and is, for example, the nptII gene, which confers a resistance to kanamycin. The *agrobacterium* which acts as host organism in this case should already comprise a plasmid with the vir region. This is required for transferring the T-DNA to the plant cell. An *agrobacterium* thus transformed can be used for the transformation of plant cells. The use of T-DNA for the transformation of plant cells has been studied and described extensively (EP 120 516; Hoekema, in: The Binary Plant Vector System, Offsetdrukkerij Kanters B. V., Alblasserdam, Chapter V; An et al. (1985) EMBO J. 4:277-287). Various binary vectors are known and in some cases commercially available, such as, for example, pBI101.2 or pBIN19 (Clontech Laboratories, Inc. USA).

In the case of the injection or electroporation of DNA or RNA into plant cells, the plasmid used need not meet any particular requirements. Simple plasmids such as those from the pUC series can be used. If intact plants are to be regenerated from the transformed cells, it is necessary for an additional selectable marker gene to be located on the plasmid.

Stably transformed cells, i.e. those which comprise the introduced DNA integrated into the DNA of the host cell, can be selected from untransformed cells when a selectable marker is a component of the introduced DNA. For example, any gene which is capable of conferring a resistance to antibiotics or herbicides (such as kanamycin, G 418, bleomycin, hygromycin or phosphinothricin and the like) can act as marker (see hereinabove). Transformed cells which express such a marker gene are capable of surviving in the presence of concentrations of a suitable antibiotic or herbicide which kill an untransformed wild type. Examples are mentioned above and preferably comprise the bar gene, which confers resistance to the herbicide phosphinothricin (Rathore K S et al. (1993) Plant Mol Biol 21(5):871-884), the nptII gene, which confers resistance to kanamycin, the hpt gene, which confers resistance to hygromycin, or the EPSP gene, which confers resistance to the herbicide glyphosate. The selection marker permits the selection of transformed cells from untransformed cells (McCormick et al. (1986) Plant Cell Reports 5:81-84). The plants obtained can be bred and hybridized in the customary manner. Two or more generations should be grown in order to ensure that the genomic integration is stable and hereditary.

The abovementioned methods are described for example in Jenes B et al. (1993) Techniques for Gene Transfer, in: Transgenic Plants, Vol. 1, Engineering and Utilization, edited by S D Kung and R Wu, Academic Press, p. 128-143 and in Potrykus (1991) Annu Rev Plant Physiol Plant Molec Biol 42:205-225). The construct to be expressed is preferably cloned into a vector which is suitable for transforming *Agrobacterium tumefaciens*, for example pBin19 (Bevan et al. (1984) Nucl Acids Res 12:8711f).

As soon as a transformed plant cell has been generated, an intact plant can be obtained using methods known to the skilled worker. Here, the starting material is, for example, callus cultures. The development of shoot and root can be induced in the known manner from these as yet undifferentiated cell lumps. The plantlets obtained can be potted on and bred.

The skilled worker is also familiar with methods of regenerating plant parts and intact plants from plant cells. For example, methods described by Fennell et al. (1992) Plant Cell Rep. 11: 567-570; Stoeger et al (1995) Plant Cell Rep. 14:273-278; Jahne et al. (1994) Theor Appl Genet 89:525-533 are used for this purpose.

The method according to the invention can advantageously be combined with other methods which bring about a pathogen resistance (for example to insects, fungi, bacteria, nematodes and the like), stress resistance or another improvement of the plant's characteristics. Examples are mentioned inter alia in Dunwell J M, Transgenic approaches to crop improvement, J Exp Bot. 2000; 51 Spec No; pages 487-96.

In a preferred embodiment, the reduction of the function of a stomatin STM1 protein in a plant is accomplished in combination with an increase in the activity of a Bax inhibitor 1 protein. This can be effected for example by expressing a nucleic acid sequence which codes for a Bax inhibitor 1 protein, for example in the mesophyll tissue and/or root tissue.

In the method according to the invention, the Bax inhibitor 1 proteins from *Hordeum vulgare* or *Nicotiana tabacum* are especially preferred.

Another subject matter of the invention relates to nucleic acid molecules which comprise nucleic acid molecules coding for stomatin STM1 proteins from barley as shown by the polynucleotides SEQ. ID No: 1, and to the nucleic acid sequences which are complementary thereto, and to the sequences derived as the result of the degeneracy (degeneration) of the genetic code and to the nucleic acid molecules which code for functional equivalents of the polypeptides as shown in SEQ. ID No: 1, the nucleic acid molecules not consisting of the SEQ ID NO: 3, 5, 7, 9, 11, 13, 15, 17, 19, 21, 23, 25, 27, 29, 31, 33, 35, 37, 39, 41 or 43.

Another subject matter of the invention relates to the stomatin STM1 protein from barley as shown in SEQ. ID No.: 2 or to one which comprises these sequences, and to functional equivalents thereof, which do not consist of the SEQ ID NO: 4, 6, 8, 10, 12, 14, 16, 18, 20, 22, 24, 26, 28, 30, 32, 34, 36, 38, 42 or 44.

Another subject matter of the invention relates to doublestranded RNA nucleic acid molecules (dsRNA molecule) which, when introduced into a plant (or into a cell, tissue, organ or seed thereof), bring about the reduction of a stomatin STM1 protein, where the sense strand of said dsRNA molecule has at least 30%, preferably at least 40%, 50%, 60%, 70% or 80%, especially preferably at least 90%, very especially preferably 100%, homology with a nucleic acid molecule as shown in SEQ ID No: or 13, or to a fragment of at least 17 base pairs, preferably at least 18, 19, 20, 21, 22, 23, 24, 25, 26, 27, 28, 29 or 30 base pairs, especially preferably at least 40, 50, 60, 70, 80 or 90 base pairs, very especially preferably at least 100, 200, 300 or 400 base pairs, most preferably at least 500, 600, 700, 800, 900, at least 1000, base pairs and which has at least 50%, 60%, 70% or 80%, especially preferably at least 90%, very especially preferably 100%, homology with a nucleic acid molecule as shown in SEQ ID No: 1, 3, 5, 7, 9, 11 or 13 but do not correspond to SEQ ID NO: 3, 5, 7, 9, 11, 13, 15, 17, 19, 21, 23, 25, 27, 29, 31, 33, 35, 37, 39, 41 or 43.

The double-stranded structure can be formed starting from a single, autocomplementary strand or starting from two complementary strands. In an especially preferred embodiment, sense and antisense sequence are linked by a linking sequence (linker) and can form for example a hairpin structure. The linking sequence can very especially preferably be an intron, which is spliced out after the dsRNA has been synthesized.

The nucleic acid sequence coding for a dsRNA can comprise further elements, such as, for example, transcription termination signals or polyadenylation signals.

A further subject matter of the invention relates to transgenic expression cassettes which comprise one of the nucleic acid sequences according to the invention. In the transgenic expression cassettes according to the invention, the nucleic acid sequence coding for the stomatin STM1 proteins from barley, wheat and maize is linked with at least one genetic control element as defined above in such a manner that the expression (transcription and, if appropriate, translation) can be accomplished in a desired organism, preferably monocotyledonous plants. Genetic control elements which are suitable for this purpose are described above. The transgenic expression cassettes can also comprise further functional elements as defined above.

Such expression cassettes comprise for example a nucleic acid sequence according to the invention, for example one which is essentially identical to a nucleic acid molecule SEQ ID No: or 13, or a fragment thereof according to the invention, where said nucleic acid sequence is preferably arranged in sense orientation or in antisense orientation relative to a promoter and can therefore lead to the expression of sense or antisense RNA, where said promoter is a promoter which is active in plants, preferably a promoter which is inducible by pathogen attack. Also comprised according to the invention are transgenic vectors which comprise said transgenic expression cassettes.

Another subject matter of the invention relates to plants which, as the result of natural processes or of artificial induction, comprise one or more mutations in a nucleic acid molecule which comprises the nucleic acid sequence as shown in SEQ ID No: or 13, where said mutation brings about a reduction in the activity, function or polypeptide quantity of a polypeptide encoded by the nucleic acid molecules as shown in SEQ ID No: or. For example a mutation prepared and identified by tilling.

Preferred in this context are plants which belong to the family Poaceae, especially preferred are plants selected among the plant genera *Hordeum*, *Avena*, *Secale*, *Triticum*, *Sorghum*, *Zea*, *Saccharum* and *Oryza*, very especially preferably plants selected from the species *Hordeum vulgare* (barley), *Triticum aestivum* (wheat), *Triticum aestivum* subsp. *spelta* (spelt), Triticale, *Avena sativa* (oats), *Secale cereale* (rye), *Sorghum bicolor* (sorghum), *Zea mays* (maize), *Saccharum officinarum* (sugar cane) and *Oryza sativa* (rice).

One embodiment of the invention therefore relates to a monocotyledonous organism comprising a nucleic acid sequence according to the invention which comprises a mutation which brings about, in the organisms or parts thereof, a reduction in the activity of one of the proteins encoded by the nucleic acid molecules according to the invention. For example, the mutation relates to one or more amino acid residues which are identified as being conserved or highly conserved in the consensus sequence shown in the figures.

In accordance with the invention, stomatin STM1 of different organisms, in particular of plants, especially preferably of useful plants, in particular of stomatins of the plant genera *Hordeum*, *Avena*, *Secale*, *Triticum*, *Sorghum*, *Zea*, *Saccharum* and *Oryza* and also *Arabidopsis* generally have a socalled consensus region. FIG. 2 shows a so-called sequence alignment of different stomatin STM1 sequences with stomatin STM1 from barley. The colors used in the sequence alignment mean the following:

red against yellow: all positions identical (therefore also identical to the consensus)
dark blue against light blue: this position in this sequence is identical to the consensus
black against green: this position in this sequence shows strong similarity with the consensus (see hereinbelow)
green against white: this position in this sequence shows weak similarity with the consensus (see hereinbelow)
black against white: this position in this sequence differs from the consensus Strong and weak similarity are allocated in accordance with the table which follows (residue consensus):

| Residue | Strong* | Weak |
|---|---|---|
| A | GS | CTV |
| B | | |
| C | | AS |
| D | E | GHKNQRS |
| E | D | HKNQRS |
| F | WY | HILM |
| G | A | DNS |
| H | Y | DEFKNQR |
| I | LMV | F |
| K | R | DEHNQST |
| L | IMV | F |
| M | ILV | F |
| N | Q | DEGHKRST |
| P | | ST |
| Q | N | DEHKRS |
| R | K | DEHNQ |
| S | AT | CDEGKNPQ |
| T | S | AKNPV |
| V | ILM | AT |
| W | FY | |
| Y | FHW | |
| Z | | |

The consensus sequence derived therefrom which can be assumed to be decisive for the physiological function of the different stomatin STM1s reads:

XPXNXGXXIVPEXKAXVXERFGKXXXTLXXGXHXLXPXVDRIAYVHSLKE

EXIPIXXXXAITKDNVXIXIXXXXYVKIXDPXXASYGVXXPIXAVXQLAQ

TTMRSELGKITLDKTFEERDXLNXXIVXXINXAAXXWGLXCXXYEIRDIX

PPXGXXXAMEMQAXAERKKRAQILESEXXXXXXXXXXXXXXXXXXXXXXX

AXXXXXXNRAXGXAEAILAXXXATAXGXXXXSXXXXXXGXXXAAXLXXAEQ

YXXAFXXXAXXXXXXLLPXXXXXPXXXXAQXX where X can be one or more of any amino acids, with X preferably being any 1 to 3 amino acids, with X more preferably being any one amino acid (SEQ ID No.: 15) The underlined amino acids were identified as being conserved in all compared sequences.

The consensus sequence preferably reads:

PPXNWGIRIVPERKAFVIERFGKYXTTLPSGIHFLXPFVDRIAYVHSLKE

EAIPIPNQTAITKDNVSIHIDGVLYVKIVDPKLASYGVENPIYAVXQLAQ

TTMRSELGKITLDKTFEERDTLNEKIVEAINVAAKDWGLQCLRYEIRDIM

PPXGVRXAMEMQAEAERKKRAQILESEGERQXHINXADGKKSSVILXSEA

AMMDQVNRAQGEAEAILARAQATAKGLXLVSQSLKEXGGXEAASLRVAEQ

YIXAFGNIAKEGTTMLLPSXAXNPASMIAQAL where X can be any one or more amino acids, with X preferably being any 1 to 3 amino acids, with X more preferably being any one amino acid (SEQ ID No.: 16)

In an especially preferred embodiment, the consensus sequence reads:

PPSNWGIRIVPERKAFVIERFGKYXTTLPSGIHFLIPFVDRIAYVHSLKE

EAIPIPNQTAITKDNVSIHIDGVLYVKIVDPKLASYGVENPIYAVIQLAQ

TTMRSELGKITLDKTFEERDTLNEKIVEAINVAAKDWGLQCLRYEIRDIM

PPXGVRXAMEMQAEAERKKRAQILESEGERQAHINXADGKKSSVILXSEA

AMMDQVNRAQGEAEAILARAQATAKGLXLVSQSLKEXGGXEAASLRVAEQ

YIXAFGNIAKEGTTMLLPSXAXNPASMIAQAL where X can be any one or more amino acids, with X preferably being any 1 to 3 amino acids, with X more preferably being any one amino acid and where the following alternative bases are comprised:

Position 3 might also show V, T or A. Position 36 might also show V or M. Position 96 might also show L, V or M. Position 182 might also show S (SEQ ID No.: 17)

The present invention therefore also relates to nucleic acid sequences which code for the above-shown consensus sequence with the SEQ ID No. 15, preferably SEQ ID No. 16, more preferably SEQ ID No. 17, and to their use in the methods according to the invention for the generation of transgenic plants with an increased pathogen resistance by reducing the content and/or the activity of at least one stomatin STM1. In this context, the consensus sequence shown is preferably characteristic of stomatin STM1 from barley and preferably also for stomatin STM1 from other plants.

Accordingly, another subject matter of the invention relates to transgenic plants, transformed with at least
a) one nucleic acid sequence, which comprises the nucleic acid molecules as shown in SEQ ID No: or 13, the nucleic acid sequences complementary thereto, and the nucleic acid molecules which code for functional equivalents of the polypeptides as shown in SEQ ID No: 15, 16 or 17,
b) one double-stranded RNA nucleic acid molecule (dsRNA molecule) which brings about the reduction of a stomatin STM1 protein, where the sense strand of said dsRNA molecule has at least 30%, preferably at least 40%, 50%, 60%, 70% or 80%, especially preferably at least 90%, very especially preferably 100%, homology with a nucleic acid molecule as shown in S SEQ ID No: or 13, or a fragment of at least 17 base pairs, preferably at least 18, 19, 20, 21, 22, 23, 24, 25, 26, 27, 28, 29 or 30 base pairs, especially preferably at least 40, 50, 60, 70, 80 or 90 base pairs, very especially preferably at least 100, 200, 300 or 400 base pairs, most preferably at least 500, 600, 700, 800, 900 or more base pairs, which has at least 50%, 60%, 70% or 80%, especially preferably at least 90%, very especially preferably 100%, homology with a nucleic acid molecule as shown in SEQ ID No: or 13,
c) one transgenic expression cassette which comprises one of the nucleic acid sequences according to the invention, or a vector according to the invention, and cells, cell cultures, tissues, parts—such as, for example in the case of plant organisms, leaves, roots and the like—or propagation material derived from such organisms,
where in one embodiment the nucleic acid molecules do not consist of the nucleic acid molecules shown in SEQ ID No: or 13 and in one embodiment do not consist of the polypeptide molecules shown in SEQ ID No: 15, 16 or 17 and In one embodiment, the plant according to the invention or the plant used in accordance with the invention is not *Arabidopsis thaliana*.

Host or starting organisms which are preferred as "transgenic organisms" are mainly plants in accordance with the above definition. In one embodiment, the transgenic organism is a mature plant, seed, shoot and seedling, and parts, propagation material and cultures derived therefrom, for example cell cultures. "Mature plants" means plants at any desired developmental stage beyond the seedling. "Seedling" means a young immature plant in an early developmental stage. Plants which are especially preferred as host organisms are plants to which the method according to the invention of obtaining a pathogen resistance in accordance with above-mentioned criteria can be applied. In one embodiment, the plant is a monocotyledonous plant such as, for example, wheat, oats, sorghum and millet, barley, rye, maize, rice, buckwheat, sorghum, triticale, spelt or sugar cane, in particular selected from the species *Hordeum vulgare* (barley), *Triticum aestivum* (wheat), *Triticum aestivum* subsp. *spelta* (spelt), *Triticale, Avena sativa* (oats), *Secale cereale* (rye), *Sorghum bicolor* (sorghum), *Zea mays* (maize), *Saccharum officinarum* (sugar cane) and *Oryza sativa* (rice).

The generation of the transgenic organisms can be accomplished with the above-described methods for the transformation or transfection of organisms.

Another subject matter of the invention relates to the transgenic plants described in accordance with the invention which additionally have an increased Bax inhibitor 1 activity, with plants which have an increased Bax inhibitor 1 activity in mesophyll cells or root cells being preferred, with transgenic plants which belong to the family Poaceae and which have an increased Bax inhibitor 1 activity in mesophyll cells or root cells being especially preferred, with transgenic plants selected among the plant genera *Hordeum, Avena, Secale, Triticum, Sorghum, Zea, Saccharum* and *Oryza* being even more preferred, and with the plant species *Hordeum vulgare* (barley), *Triticum aestivum* (wheat), *Triticum aestivum* subsp.*spelta* (spelt), *Triticale, Avena sativa* (oats), *Secale cereale* (rye), *Sorghum bicolor* (sorghum), *Zea mays* (maize), *Saccharum officinarum* (sugar cane) and *Oryza sativa* (rice) being preferred most of all.

Another subject matter of the invention relates to the use of the transgenic organisms according to the invention and of the cells, cell cultures, parts—such as, for example in the case of transgenic plant organisms, roots, leaves and the like—and transgenic propagation material such as seeds or fruits derived therefrom for the preparation of foodstuffs or feedstuffs, pharmaceuticals or fine chemicals.

In one embodiment, the invention furthermore relates to a method for the recombinant production of pharmaceuticals or fine chemicals in host organisms, where a host organism or a part thereof is transformed with one of the above-described nucleic acid molecule expression cassettes and this expression cassette comprises one or more structural genes which code for the desired fine chemical or catalyse the biosynthesis of the desired fine chemical, where the transformed host organism is grown and where the desired fine chemical is isolated from the growth medium. This method can be applied widely to fine chemicals such as enzymes, vitamins, amino acids, sugars, fatty acids, natural and synthetic flavorings, aroma substances and colorants. Especially preferred is the production of tocopherols and tocotrienols and carotenoids. The growing of the transformed host organisms and the isolation from the host organisms or the growth medium are accomplished by methods known to the skilled worker. The production of pharmaceuticals such as, for example, antibodies or vaccines, is described in Hood E E, Jilka J M (1999). Curr Opin Biotechnol. 10(4):382-6; Ma J K, Vine N D (1999). Curr Top Microbiol Immunol. 236:275-92.

In accordance with the invention, the expression of a structural gene can, of course, also take place, or be influenced, independently of carrying out the method according to the invention or using the subject matters according to the invention.

Sequences
1. SEQ ID NO:1 and 2: HvSTM1, derived from cDNA
2. SEQ ID NO: 3 and 4:
LOCUS XP_480193 377 aa linear PLN 09-NOV-2004
DEFINITION putative Band 7 protein [*Oryza sativa* (japonica cultivar group)].
ACCESSION XP_480193
VERSION XP_480193.1 GI:50941331
DBSOURCE REFSEQ: accession XM_480193.1
KEYWORDS
SOURCE *Oryza sativa* (japonica cultivar group)
3. SEQ ID NO: 5 and 6:
LOCUS XP_480193 377 aa linear PLN 09-NOV-2004
DEFINITION putative Band 7 protein [*Oryza sativa* (japonica cultivar group)].
ACCESSION XP_480193
VERSION XP_480193.1 GI:50941331
DBSOURCE REFSEQ: accession XM_480193.1
KEYWORDS.
SOURCE *Zea mays*
4. SEQ ID NO: 7 and in 8
LOCUS CAB81408 515 aa linear PLN 16-APR-2005
DEFINITION putative protein [*Arabidopsis thaliana*].
ACCESSION CAB81408
VERSION CAB81408.1 GI:7269612
DBSOURCE embl locus ATCHRIV67, accession AL161571.2
KEYWORDS
SOURCE *Arabidopsis thaliana* (thale cress)
5. SEQ ID NO:9 and 10:
LOCUS NP_567778 411 aa linear PLN 04-NOV-2005
DEFINITION unknown protein [*Arabidopsis thaliana*].
ACCESSION NP_567778
VERSION NP_567778.1 GI:18417021
DBSOURCE REFSEQ: accession NM_118894.2
KEYWORDS
SOURCE *Arabidopsis thaliana* (thale cress)
6. SEQ ID NO:11 and 12:
LOCUS NP_200221 401 aa linear PLN 04-NOV-2005
DEFINITION unknown protein [*Arabidopsis thaliana*].
ACCESSION NP_200221
VERSION NP_200221.1 GI:15239547
DBSOURCE REFSEQ: accession NM_124790.2
KEYWORDS
SOURCE *Arabidopsis thaliana* (thale cress)
7. SEQ ID NO: 13 and 14:
LOCUS AAM63205 401 aa linear PLN 14-APR-2003
DEFINITION stomatin-like protein [*Arabidopsis thaliana*].
ACCESSION AAM63205
VERSION AAM63205.1 GI:21554125
DBSOURCE accession AY085995.1
KEYWORDS
SOURCE *Arabidopsis thaliana* (thale cress)
8. SEQ ID NO: 15, 16, 17: Consensus sequences derived from a sequence alignment of the polypeptides from SEQ ID NO.: 1 to 14.
9. SEQ ID NO: 18 and 19: PCR primer

EXAMPLES

General Methods:

The chemical synthesis of oligonucleotides can take place for example in a known manner by the phosphoamidite method (Voet, Voet, 2nd edition, Wiley Press New York, page 896-897). The cloning steps carried out for the purposes of the present invention, such as, for example, restriction cleavages, agarose gel electrophoresis, purification of DNA fragments, transfer of nucleic acids to nitrocellulose and nylon membranes, linkage of DNA fragments, transformation of *E. coli* cells, culturing of bacteria, replication of phages and sequence analysis of recombinant DNA are carried out as described in Sambrook et al. (1989) Cold Spring Harbour Laboratory Press; ISBN 0-87969-309-6. The sequencing of recombinant DNA molecules takes place using a laser fluorescence DNA sequencer from the company MWG-Licor by the method of Sanger (Sanger et al. (1977) Proc Natl Acad Sci USA 74:5463-5467).

Example 1

Plants, Pathogens and Inoculation

The barley variety Golden Promise is from Patrick Schweizer, Institut für Pflanzengenetik und Kulturpflanzenforschung Gatersleben. The variety Pallas and the backcrossed line BClngrid-mlo5 was provided by Lisa Munk, Department of Plant Pathology, Royal Veterinary and Agricultural University, Copenhagen, Denmark. Its preparation is described (Kølster P et al. (1986) Crop Sci 26: 903-907).

Unless otherwise described, the seed which has been pregerminated for 12 to 36 hours in the dark on moist filter paper is placed in batches of 5 grains along the edge of a square pot (8×8 cm) in Fruhstorfer soil type P, covered with soil and watered regularly with tapwater. All plants are grown in controlled-environment cabinets or chambers at from 16 to 18° C. for 5 to 8 days, at a relative atmospheric humidity of from 50 to 60% and in a 16/8-hour photo period with 3000 and 5000 lux, respectively (50 and 60 µmols$^{-1}$m$^{-2}$ photon flux density, respectively) and employed in the experiments in the seedling stage. In the case of experiments where primary leaves are treated, the latter are fully developed.

Before the plants are subjected to the transient transfection experiments, they are grown in controlled-environment cabinets or chambers at a daytime temperature of 24° C., nighttime temperature of 20° C., relative atmospheric humidity of 50 to 60% and a 16/8-hour photo period with 30 000 lux.

Powdery mildew of barley *Blumeria graminis* (DC) Speer f.sp. *hordei* Em. Marchal der Rasse A6 (Wiberg A (1974) Hereditas 77: 89-148) (BghA6) is used to inoculate barley plants. The mildew was provided by the Institut für Biometrie, JLU Gießen. The inoculum is maintained in controlled-environment cabinets under conditions which are identical to those which have been described above for the plants by transferring the conidia from infected plant material to 7-day old barley plants cv. Golden Promise which have been raised at regular intervals, at a density of 100 conidia/mm$^2$.

The inoculation with BghA6 is carried out using 7-day-old seedlings by shaking the conidia of infected plants in an inoculation tower at a density of approximately 100 conidia/mm$^2$ (unless otherwise stated).

Example 2

RNA Extraction

Total RNA is extracted from 8 to 10 primary leaf segments (5 cm in length) by means of "RNA extraction buffer" (AGS, Heidelberg, Germany).

To this end, central primary leaf segments 5 cm in length are harvested and homogenized in liquid nitrogen using a pestle and mortar. The homogenate is stored at −70° C. until the RNA is extracted.

Total RNA is extracted from the frozen leaf material with the aid of an RNA extraction kit (AGS, Heidelberg). To this end, 200 mg of the frozen leaf material is covered with 1.7 ml of RNA extraction buffer (AGS) in a microcentrifuge tube (2 ml) and immediately subjected to thorough mixing. After the addition of 200 µl of chloroform, the mixture is again mixed thoroughly and shaken for 45 minutes at room temperature on an orbital shaker at 200 rpm. Thereafter, the mixture is centrifuged for 15 minutes at 20 000 g and 4° C. in order to separate the phases, the aqueous top phase is transferred into a fresh microcentrifuge tube, and the bottom phase is discarded. The aqueous phase is again purified with 900 µl of chloroform by homogenizing 3 times for 10 seconds and recentrifuging (see above) and removing the top phase. To precipitate the RNA, 850 µl of 2-propanol are then added, the mixture is homogenized and placed on ice for 30 to 60 minutes. Thereafter, the mixture is centrifuged for 20 minutes (see above), the supernatant is carefully decanted off, 2 ml of 70% strength ethanol (−20° C.) are added, using a pipette, and the batch is mixed and again centrifuged for 10 minutes. The supernatant is then again decanted off and the pellet is carefully freed from residual fluid, using a pipette, and then dried in a stream of pure air on a sterile workbench. Thereafter, the RNA is dissolved in 50 µl of DEPC water on ice, and the batch is mixed and centrifuged for 5 minutes (see above). 40 µl of the supernatant are transferred into a fresh microcentrifuge tube as RNA solution and stored at −70° C.

The RNA concentration is determined photometrically. To this end, the RNA solution is diluted 1:99 (v/v) with distilled water and the absorbance (Photometer DU 7400, Beckman) is measured at 260 nm ($E_{260\,nm}$=1 at 40 µg RNA/ml). In accordance with the calculated RNA contents, the concentrations of the RNA solutions are subsequently standardized with DEPC water to 1 µg/µl and verified in an agarose gel.

To verify the RNA concentrations in a horizontal agarose gel (1% agarose in 1×MOPS buffer with 0.2 µg/ml ethidium bromide), 1 µl of RNA solution is treated with 1 µl of 10×MOPS, 1 µl of color marker and 7 µl of DEPC water, separated according to size at a voltage of 120 V in the gel in 1×MOPS running buffer in the course of 1.5 hours and photographed under UV light. Any differences in concentration of the RNA extracts are standardized with DEPC water, and the standardization is again verified in the gel.

Example 3

Cloning the Barley Stomatin STM1 cDNA Sequence

A contig for stomatin STM1 was constructed from the publicly available EST sequences HW03O11, HO31J10 (Crop EST Database of IPK Gatersleben) and BM368585 (SCRI). The clone was subcloned into pIPK-TA38 (see below) via restriction cleavage & ligation. The following approach was used for the end-to-end PCR of the full-length clone HvSTM1.

```
Upper primer:
GATATGGCGATGTCGACGGCGACC

Lower primer:
AACTTACTTCTGGTGCGGAAAGG
```

Cycler Program:

| | | |
|---|---|---|
| 94° C. | 5 minutes | |
| 94° C. | 30 seconds | |
| 59.8° C. | 30 seconds | 35 cycles |
| 72° C. | 1 minute 30 seconds | |
| 72° C. | 10 minutes | |
| 4° C. | | |

Mix:
1 µl template (cDNA barley)
5 µl 10× buffer
20 pmol primer 1
20 pmol primer 2
1 µl dNTPs (Invitrogen, 10 mM)
1 µl cloned Pfu DNA polymerase (Stratagene, 2.5 U/µl)
H$_2$O to 50 µl The end-to-end PCR yielded a product of 1086 bp. The PCR product obtained was isolated via a 1% strength agarose gel, extracted from the gel, cloned into pCR4-Topo (Invitrogen Life Technologies) by means of T-overhand ligation and sequenced.

Example 5

Carrying Out the Transient Single-Cell RNAi Analysis

Biological Material

Barley near-isogenic lines (NILs) of the cultivars cv Ingrid (Mlo) and Ingrid BC$_7$ mlo5 or barley cv Golden Promise were grown in controlled-environment chambers in pots filled with potting compost (provenance: IPK Gatersleben) (16 hours light from metal halogen lamps; 8 hours darkness, relative atmospheric humidity of 70%, constant temperature of 18° C.). *Blumeria graminis* DC Speer f.sp. *hordei* (Bgh) (isolate 4.8 comprising AvrMla-9 was grown at 22° C. and 16 hours light by weekly transfer to fresh barley leaves of the cultivar cv. Golden Promise. *Blumeria graminis* DC Speer f.sp. *tritici* Em Marchal (Bgt) of the Swiss isolate FAL (Reckenholz) was propagated at 22° C. and 16 hours light by weekly transfer to fresh leaves of wheat of the cultivar cv. Kanzler.

Plasmid Vectors

The vector pIPKTA38 was used as entry vector for the Gateway™ cloning system (Invitrogen). The vector is a pENTR1a derivative where the ccdB gene had been removed and a novel multiple cloning site had been inserted. The destination vector used was pIPKTA30N, which is based on a pUC18 background and which comprises a constitutive promoter, terminator and two Gateway cassettes comprising attR sites, ccdB gene and a chloramphenicol resistance gene. The two cassettes are arranged in opposite directions and separated from one another by a spacer from the wheat RGA2 gene (accession number AF326781). This vector system permits a one-step transfer of two copies of a PCR fragment via entry vector into the dsRNAi vector by means of Gateway LR clonase reaction (Invitrogen).

PCR and Primer Design

EST sequences of the target gene were amplified via PCR. Purified DNA from the selected cDNA clones was used as template for the PCR reaction. The primers were derived with the aid of the software package "Primer3" in the batch-file mode using the 5'-EST sequences. The EST sequences were typically amplified with a universal forward primer and a reverse EST-specific primer. The amplificates were in the range of from 400-700 bp. The primers were 20-22 bp in length and had a $T_m$ of approx. 65° C. The PCR reactions were carried out in 96-well microtiter plates using a DNA polymerase which produces blunt ends (ThermalAce; Invitrogen). The PCR products were purified with the aid of the MinElute UF Kit (Qiagen, Hilden, Germany) and eluted with 25 µl of water.

Ligation into the Entry Vector

The PCR fragments were cloned into the Swa I cleavage site of this vector pIPKTA38. The ligation was carried out at 25° C. in the presence of the N U T4 DNA ligase (MBI Fermentas) and 5 U of Swa I per reaction. To optimize the reaction conditions for Swa I, the buffer was supplemented with NaCl to a final concentration of 0.05 M. After 1 h, the reaction was terminated by heating for 15 minutes at 65° C. Thereafter, an additional 5 U of Swa I were added in order to suppress a religation of the plasmid. The Swa I buffer was supplemented with additional NaCl to a final concentration of 0.1 M. The reaction mixtures were incubated for a further hour at 25° C.

The resulting recombinant pIPKTA38-EST clones were employed for the transformation of chemically competent *E. coli* DH10B cells in 96-well PCR microtiter plates (5 µl of ligation mixture per 20 µl of competent cells) and plated onto LB agar plates with kanamycin. One colony of each cloning reaction was picked and taken up in 1.2 ml of LB+kanamycin liquid culture and distributed in 96-deep-well plates. The plates were covered with an air-permeable film and incubated for 18 hours at 37° C. on a shaker. Thereupon, the deep-well plates were centrifuged for 10 minutes at 750 g, and the pellets were used for isolating the plasmid by means of the NucleoSpin Robot-96 plasmid kit (Macherey-Nagel). The presence of the pIPKTA38 plasmid was verified via restriction digest with EcoRI. The positive pIPKTA38 clones were employed as donor vector in the LR reaction.

LR Reaction and Preparation of RNAi Constructs

EST fragments in pIPKTA38 were cloned as inverted repeats into the RNAi destination vector pIPKTA30N via a single LR recombination reaction. The reaction volume was reduced to 6 µl and comprised 1 µl of the pIPKTA38 donor clone, 1 µl pIPKTA30N destination vector (150 ng/µl), 0.8 µL clonase enzyme mix and 3.2 µl of H$_2$O. The reaction was incubated overnight at room temperature, and 5 µl of it were transformed into 20 µl of chemically competent *E. coli* cells in 96-well PCR plates. Two 96-deep-well plates with LB+ampicillin were half-filled with half the volume of the transformation mix, sealed with an air-permeable film and incubated for 24 hours at 37° C. on a plate shaker. Thereafter, the deep-well plates were centrifuged for 10 minutes at 750 g, and the pellets of two duplicates of each clone were combined and subjected to the plasmid preparation. The NucleoSpin Robot-96 plasmid kit (Macherey-Nagel) was used for this purpose. The DNA quantity was on average 20-30 µg of DNA per clone.

Particle Bombardment and Inoculation with Fungal Spores

Segments of primary leaves of 7-day-old barley seedlings were placed on 0.5% w/v Phytoagar (Ducheva) in water comprising 20 ppm of benzimidazole and bombarded with gold particles (diameter 1 µm) in a PDS-1000/He system (Bio-Rad, Munich, Germany) using the Hepta adaptor with a helium pressure of 900 psi. Seven leaf segments were employed per bombardment. The particle coating with 0.5 M Ca(NO$_3$)$_2$ was carried out as described by Schweizer et al., 1999, except that the stock solution comprised 25 mg ml$^{-1}$ gold. After the coating, all of the supernatant was removed, and the particles were resuspended in 30 µl of pure ethanol. 2.18 mg of gold microcarrier were employed per bombardment. Four hours after the bombardment, the leaf segments were placed on 1% w/v Phytoagar (Ducheva) in water comprising 20 ppm of benzimidazole in 20×20 cm plates and weighted down at both ends.

The leaf segments were inoculated with spores of Bgt and Bgh 48 hours or 96 hours after the particle bombardment. The plasmid pUbiGUS, which comprises the β-*glucuronidase* (GUS) gene under the control of the maize ubiquitin promoter, was employed as reporter construct for transformed epidermal cells. 40 hours after the inoculation, the leaf segments were stained on GUS activity and destained for 5 minutes with 7.5% w/v trichloroacetic acid and 50% methanol. The GUS staining solution has been described in Schweizer et al. 1999.

To evaluate the interaction of phenotypes, GUS-stained cells were counted under an optical microscope, and the number of haustoria in these transformed cells was determined, whereby the haustorial index is derived. As an alternative, the number of GUS-stained cells which comprised at least one haustorium was determined, and the susceptibility index was calculated thereby.

see FIG. 1: Increasing the host resistance by stomatin STM1 RNAi

We claim:

1. A method of increasing resistance to pathogens in a plant or in a part of a plant, comprising altering cell wall structure by introducing a nucleic acid molecule suitable for forming a double-strand ribonucleic acid molecule (dsRNA), wherein the nucleic acid molecule comprises:
   a) the nucleic acid sequence of SEQ ID NO: 1;
   b) a nucleic acid sequence coding for a polypeptide having the amino acid sequence of SEQ ID NO: 2;
   c) a nucleic acid sequence coding for a polypeptide having at least 90% sequence identity to the amino acid sequence of SEQ ID NO: 2; or
   d) a nucleic acid sequence that is complementary to the nucleic acid sequence of a), b), or c).

2. The method of claim 1, wherein membrane permeability is reduced.

3. A method of increasing resistance to pathogens in a plant or in a part of a plant, comprising reducing activity of a stomatin STM1 protein in a plant or in a part of a plant by introducing a nucleic acid molecule suitable for forming a double-strand ribonucleic acid molecule (dsRNA), wherein the stomatin STM1 protein is encoded by:
   a) the nucleic acid sequence of SEQ ID NO: 1;
   b) a nucleic acid sequence coding for a polypeptide having the amino acid sequence of SEQ ID NO: 2; or
   c) a nucleic acid sequence coding for a polypeptide having at least 90% sequence identity to the amino acid sequence of SEQ ID NO: 2.

4. The method of claim 3, wherein the activity of the stomatin STM1 protein in mesophyll cells and/or epidermal cells is reduced.

5. The method of claim 3, wherein the activity of the stomatin STM1 protein in lemma, palea, and/or glume is reduced.

6. The method of claim 3, wherein an endogenous nucleic acid sequence coding for a stomatin STM1 polypeptide is mutated.

7. The method of claim 3, wherein the pathogens are selected from the group of families consisting of Pucciniaceae, Mycosphaerellaceae and Hypocreaceae.

8. The method of claim 3, wherein
   a) the expression of the stomatin STM1 protein is reduced;
   b) the stability of the stomatin STM1 protein or of the mRNA molecules which correspond to the stomatin STM1 protein is reduced;
   c) the activity of the stomatin STM1 protein is reduced;
   d) the transcription of a gene coding for the stomatin STM1 protein is reduced by the expression of an endogenous or artificial transcription factor; or
   e) an exogenous factor which reduces the activity of the stomatin STM1 protein is added to the food or to the medium.

9. The method of claim 3, wherein the reduction in the activity of the stomatin STM1 protein is achieved by introducing a nucleic acid molecule coding for a double-strand ribonucleic acid molecule (dsRNA) comprising a sense strand and an antisense strand, wherein the sense strand comprises:
   a) the nucleic acid sequence of SEQ ID NO: 1;
   b) a nucleic acid sequence coding for a polypeptide having the amino acid sequence of SEQ ID NO: 2;
   c) a nucleic acid sequence coding for a polypeptide having at least 90% sequence identity to the amino acid sequence of SEQ ID NO: 2; or
   d) a nucleic acid sequence that is complementary to the nucleic acid sequence of a), b), or c).

10. The method of claim 9, comprising:
    a) introducing, into a plant cell, a recombinant expression cassette comprising, in operable linkage with a promoter which is active in plants, said nucleic acid molecule;
    b) regenerating a plant from the plant cell, and
    c) expressing said nucleic acid sequence in a sufficient amount and over a sufficient period of time to generate, or to increase, a pathogen resistance in said plant.

11. The method of claim 10, wherein the promoter which is active in plants is selected from the group consisting of: pathogen-inducible promoter; epidermis-specific promoter; mesophyll-specific promoter; lemma-specific promoter; palea-specific promoter; and gluma-specific promoter.

12. The method of claim 3, wherein activity of a polypeptide coding for Bax inhibitor 1, ROR2, SnAP34 and/or Lumenal Binding protein BiP is increased in the plant, the plant organ, the plant tissue or the plant cell.

13. The method of claim 3, wherein activity of a polypeptide coding for ARM1, RacB, CSL1, HvNaOX and/or MLO is decreased in the plant, the plant organ, the plant tissue or the plant cell.

14. The method of claim 3, wherein the pathogen is selected from the group of species consisting of *Puccinia triticina, Puccinia striiformis, Mycosphaerella graminicola, Stagonospora nodorum, Fusarium graminearum, Fusarium culmorum, Fusarium avenaceum, Fusarium poae* and *Microdochium nivale*.

15. The method of claim 3, wherein the plant is selected from the group of plant genera consisting of *Hordeum, Avena, Secale, Triticum, Sorghum, Zea, Saccharum* and *Oryza*.

16. An isolated nucleic acid molecule coding for a stomatin STM1 protein, comprising: a) the nucleic acid sequence of SEQ ID NO: 1; b) a nucleic acid sequence coding for a polypeptide having the amino acid sequence of SEQ ID NO: 2; or c) a nucleic acid sequence coding for a polypeptide having at least 90% sequence identity to the amino acid sequence of SEQ ID NO: 2.

17. A nucleic acid construct comprising the nucleic acid molecule of claim 16 in antisense or sense orientation operably linked with a promoter selected from the group consisting of barley promoter, maize promoter, rice promoter, pathogen- inducible promoter, epidermis-specific promoter, mesophyll-specific promoter, lemma-specific promoter, palea-specific promoter, and glume-specific promoter.

18. A double-stranded RNA nucleic acid molecule (dsRNA molecule) comprising a sense strand and an antisense strand, wherein the sense strand comprises the nucleic acid molecule of claim 16.

19. The dsRNA molecule of claim 18, wherein the sense strand and the antisense strand are bonded covalently with one another.

20. A DNA expression cassette comprising the nucleic acid molecule of claim 16, wherein said nucleic acid molecule is in sense orientation relative to a promoter.

21. A DNA expression cassette comprising the nucleic acid molecule of claim 16, wherein said nucleic acid molecule is in antisense orientation relative to a promoter.

22. A DNA expression cassette comprising a nucleic acid sequence coding for the dsRNA molecule of claim 18, wherein said nucleic acid sequence is linked with a promoter.

23. The DNA expression cassette of claim 20, wherein the nucleic acid molecule is linked with a promoter which is functional in plants.

24. The DNA expression cassette of claim 23, wherein the promoter which is functional in plants is selected from the group consisting of: barley promoter, maize promoter, rice promoter, pathogen-inducible promoter, epidermis-specific promoter, mesophyll-specific promoter, lemma-specific promoter, palea-specific promoter, and glume-specific promoter.

25. A vector comprising the DNA expression cassette of claim 20.

26. A cell comprising the nucleic acid molecule of claim 16, a dsRNA molecule comprising said nucleic acid molecule as sense strand, a DNA expression cassette comprising said nucleic acid molecule, or a vector comprising said nucleic acid molecule or said DNA expression cassette, wherein endogenous activity of a polypeptide encoded by said nucleic acid molecule is reduced.

27. A transgenic nonhuman organism comprising the nucleic acid molecule of claim 16, a dsRNA molecule comprising said nucleic acid molecule as sense strand, a DNA expression cassette comprising said nucleic acid molecule, a cell comprising said nucleic acid molecule, said DNA expression cassette, or said dsRNA molecule, or a vector comprising said nucleic acid molecule or said DNA expression cassette.

28. The transgenic nonhuman organism of claim 27, which is a monocotyledonous organism.

29. The transgenic nonhuman organism of claim 27, wherein the organism has an increased Bax inhibitor 1 protein activity, an increased ROR2 and/or SnAP34 activity and/or a reduced RacB, CSL1 and/or HvRBOHF activity.

30. The nonhuman organism of claim 27, wherein the organism has an increased Bax inhibitor 1 activity, an increased ROR2 and/or SnAP34 activity and/or a reduced RacB, CSL1 and/or HvRBOHF activity in mesophyll cells and/or root cells.

31. The organism of claim 27, wherein the organism is selected from the group of the species consisting of *Hordeum vulgare* (barley), *Triticum aestivum* (wheat), *Triticum aestivum subsp.spelta* (spelt), *Triticale, Avena sativa* (oats), *Secale cereale* (rye), *sorghum bicolor* (millet), *Zea mays* (maize), *Saccharum officinarum* (sugar cane) and *Oryza sativa* (rice).

32. A method for generating a plant which is resistant to mesophyll-cell-penetrating pathogens comprising introducing the nucleic acid molecule of claim 16, a dsRNA molecule comprising said nucleic acid molecule as sense strand, a DNA expression cassette comprising said nucleic acid molecule, or a vector comprising said nucleic acid molecule or said DNA expression cassette into a plant cell and regenerating a plant from the plant cell.

33. A method for generating a plant which is resistant to epidermis-penetrating pathogens comprising introducing the nucleic acid molecule of claim 16, a dsRNA molecule comprising said nucleic acid molecule as sense strand, a DNA expression cassette comprising said nucleic acid molecule, or a vector comprising said nucleic acid molecule or said DNA expression cassette into a plant cell and regenerating a plant from the plant cell.

34. The method of claim 32, wherein the mesophyll-cell-penetrating pathogen is Septoria or rusts.

35. A transformed harvest, propagation material or composition comprising the nucleic acid molecule of claim 16, a dsRNA molecule comprising said nucleic acid molecule as sense strand, a DNA expression cassette comprising said nucleic acid molecule, a cell comprising said nucleic acid molecule, said DNA expression cassette, or said dsRNA molecule, or a vector comprising said nucleic acid molecule or said DNA expression cassette.

36. The method of claim 33, wherein the epidermis-penetrating pathogen is mildew.

37. A method of increasing resistance to pathogens in a plant or in a part of a plant, comprising reducing activity of a stomatin STM1 protein in a plant or in a part of a plant by introducing a nucleic acid molecule suitable for forming a double-strand ribonucleic acid molecule (dsRNA) comprising a sense strand and an antisense strand, wherein the sense strand comprises a fragment of at least 300 nucleotides of the nucleic acid sequence of SEQ ID NO: 1, and wherein said nucleic acid molecule, when introduced and expressed in a plant or in a part of a plant, confers reduction of said stomatin STM1 protein in said plant or in said part of the plant.

* * * * *